US012708655B2

(12) United States Patent
Feldman et al.

(10) Patent No.: US 12,708,655 B2
(45) Date of Patent: Aug. 18, 2026

(54) BOTANICALS AS WNT/BETA-CATENIN ACTIVATORS, MOLECULAR PATHWAY REGULATORS, TISSUE REGENERATORS AND HEALTH BIOMARKER REGULATORS

(71) Applicant: Arbor Life Holdings, Ltd., Thornhill (CA)

(72) Inventors: Peter R. Feldman, Thornhill (CA); Luciano E. Marra, Toronto (CA); Dennis M. Brown, Menlo Park, CA (US); Deborah J. Cahan, Thornhill (CA)

(73) Assignee: Arbor Life Holdings, Ltd., Thornhill (CA)

( * ) Notice: Subject to any disclaimer, the term of this patent is extended or adjusted under 35 U.S.C. 154(b) by 395 days.

(21) Appl. No.: 18/260,195

(22) PCT Filed: Dec. 30, 2020

(86) PCT No.: PCT/US2020/067585
§ 371 (c)(1),
(2) Date: Jun. 30, 2023

(87) PCT Pub. No.: WO2022/146435
PCT Pub. Date: Jul. 7, 2022

(65) Prior Publication Data

US 2024/0075089 A1 Mar. 7, 2024

(51) Int. Cl.

| | |
|---|---|
| ***A61P 17/14*** | (2006.01) |
| ***A61K 31/10*** | (2006.01) |
| ***A61K 31/355*** | (2006.01) |
| ***A61K 31/4188*** | (2006.01) |
| ***A61K 31/522*** | (2006.01) |
| ***A61K 36/03*** | (2006.01) |
| ***A61K 36/074*** | (2006.01) |
| ***A61K 36/21*** | (2006.01) |
| ***A61K 36/232*** | (2006.01) |
| ***A61K 36/28*** | (2006.01) |
| ***A61K 36/31*** | (2006.01) |
| ***A61K 36/42*** | (2006.01) |
| ***A61K 36/48*** | (2006.01) |
| ***A61K 36/537*** | (2006.01) |
| ***A61K 36/539*** | (2006.01) |
| ***A61K 36/704*** | (2006.01) |
| ***A61K 36/73*** | (2006.01) |
| ***A61K 45/06*** | (2006.01) |
| ***A61K 47/46*** | (2006.01) |
| ***A61P 17/00*** | (2006.01) |

(52) U.S. Cl.

CPC .............. *A61K 36/28* (2013.01); *A61K 31/10* (2013.01); *A61K 31/355* (2013.01); *A61K 31/4188* (2013.01); *A61K 31/522* (2013.01); *A61K 36/03* (2013.01); *A61K 36/074* (2013.01); *A61K 36/21* (2013.01); *A61K 36/232* (2013.01); *A61K 36/31* (2013.01); *A61K 36/42* (2013.01); *A61K 36/48* (2013.01); *A61K 36/537* (2013.01); *A61K 36/539* (2013.01); *A61K 36/704* (2013.01); *A61K 36/73* (2013.01); *A61K 45/06* (2013.01); *A61K 47/46* (2013.01); *A61P 17/00* (2018.01); *A61P 17/14* (2018.01)

(58) Field of Classification Search

None

See application file for complete search history.

(56) References Cited

U.S. PATENT DOCUMENTS

| | | | |
|---|---|---|---|
| 8,025,908 | B2 | 9/2011 | Anderson |
| 10,507,177 | B1 | 12/2019 | Kawa |
| 2008/0292607 | A1 | 11/2008 | Mazzio et al. |
| 2009/0004168 | A1 | 1/2009 | Schakel |
| 2014/0038922 | A1 | 2/2014 | Lum et al. |
| 2015/0216918 | A1 | 8/2015 | Nair |
| 2016/0004298 | A1 | 1/2016 | Mazed et al. |

FOREIGN PATENT DOCUMENTS

| | | | | | |
|---|---|---|---|---|---|
| DE | 202018101021 | U * | 3/2018 | | |
| KR | 100966902 | B1 * | 6/2010 | .............. | A61K 8/97 |
| KR | 20170004632 | B1 | 1/2017 | | |

OTHER PUBLICATIONS

Tomoya Takahashi et. al. (Proanthocyanidins from Grape Seeds Promote Proliferation of Mouse Hair Follicle Cells In vitro and Convert Hair Cycle In vivo, Acta Derm Venerol (Stockh), 1998; 78: 428-432) (Year: 1998).*

(Continued)

*Primary Examiner* — Anand U Desai

*Assistant Examiner* — Jacob A Boeckelman

(74) *Attorney, Agent, or Firm* — Christensen O'connor Johnson Kindness PLLC

(57) ABSTRACT

The present disclosure provides botanicals and/or biotin or analogs thereof, that proliferate or reduce stem cell populations and activate or attenuate Wat/β-Catenin signaling and thus treat or prevent diseases related to signal transduction. In particular, the disclosure provides Botanicals and Biotin or analogs thereof, that proliferate or reduce stem cell populations and activate or attenuate Wnt/β-Catenin signaling in tissues expressing WntlOB including, adipose, adrenal, artery, blood, bone marrow, brain, breast, cervix, colon, esophagus, heart, intestine, kidney, liver, lung, muscle, ovary, pituitary, prostate, skin, spleen, testis, thyroid, uterus and vagina. The present compositions and methods are particularly suited to growing and melanizing hair.

5 Claims, 30 Drawing Sheets

(56) References Cited

OTHER PUBLICATIONS

International Preliminary Report on Patentability mailed Jul. 13, 2023, issued in International Application No. PCT/US2020/067585, filed Dec. 30, 2020, 7 pages.
"A Story of Hair Regeneration," LUX International Magazine, London, England, <https://lux-life.digital/issues/november-2017/>, Nov. 2017, 4 pages.
"Hair Leaflet," Replenology Inc., Richmond, VA, <https://www.replenology.com/wp-content/uploads/2020/09/Replenology-Leaflet.pdf> [retrieved Dec. 18, 2024], Feb. 2018, 12 pages.
"21 to Grow: 21 Natural Scientific Pathways Shown to Stimulate Hair Growth and Prevent Hair Loss," Replenology Inc., Richmond, VA, <https://www.replenology.com/wp-content/uploads/2020/08/ALL17-10-21-to-Grow-Brochure_011718.pdf> [retrieved Dec. 18, 2024], Jan. 2018, 36 pages.
Han. L. and H. Wei, Database WPI, Week 201143, Thomson Scientific, London AN 2011-F22058 and CN 102 000 164, Apr. 6, 2011.
Li, X., et al., Database WPI, Week 201153, Thomson Scientific, London AN 2011-H91083 and CN 102 078 569, Jun. 1, 2011.
Nantong Snakes Treating Inst, Database WPI, Week 201153, Thomson Scientific, London AN 2014-W63482 and CN 104 055 709, Sep. 24, 2014.
Rhilos Cosmetics Co Ltd, Database WPI, Week 2020072, Thomson Scientific, London AN 2020-824355, Aug. 20, 2020.
Shao, H., et al., Database WPI, Week 201144, Week 201144, Thomson Scientific, London AN 2011-G03056 and CN 102 018 886, Apr. 20, 2011.
Extended European Search Report mailed Oct. 28, 2024, issued in related EP Application No. 20968167.5, filed Dec. 30, 2020, 11 pages.
International Search Report mailed May 3, 2021, issued in International Publication No. PCT/US2020/067585, filed Dec. 20, 2020, 4 pages.
Written Opinion mailed May 3, 2021, issued in International Publication No. PCT/US2020/067585, filed Dec. 20, 2020, 5 pages.

* cited by examiner

BOTANICALS AS WNT/BETA-CATENIN ACTIVATORS, MOLECULAR PATHWAY REGULATORS, TISSUE REGENERATORS AND HEALTH BIOMARKER REGULATORS

CROSS-REFERENCES TO RELATED APPLICATIONS

This application is a National Stage of International Application No. PCT/US2020/067585, filed Dec. 30, 2020, the contents of which is expressly incorporated herein. All references cited are expressly incorporated herein, including U.S. Provisional Application No. 62/810,527.

BACKGROUND OF THE INVENTION

This application relates to regulation of stem cells and hair growth. Stem cells are mainly characterized by the properties of self-renewal and the potency to differentiate into diverse cell types. Studies have demonstrated that these properties are regulated by different growth factors including members of the Wnt/β-catenin protein family. In hair follicles, stem cells are "quiescent," meaning they are normally inactive, but they quickly activate during a new hair cycle driving new hair growth. Hair follicle stem cells remain dormant during telogen for a few weeks, before proliferating during anagen.[1] Therefore, the stem cells give the follicle its regenerative capacity, allowing it to cycle through its growth phases. The quiescence of hair follicle stem cells is regulated by many factors. In certain cases they fail to activate, which is what causes hair loss. Wnt proteins are secreted glycoproteins that can activate different intracellular signaling pathways. Recent studies have suggested that hair loss occurs when the supply or the activity of hair follicle stem cells is exhausted. How they retain their stemness, or ability to self-renew and differentiate appears to be intimately related to Wnt/β-catenin activity.[2]

In mammals, Wnt/β-catenin signaling features prominently in stem cells. The interactions between Wnt ligands and their receptors result in the activation of various intracellular signaling cascades that can be cross-connected or act independently. Depending on the pathway activated, Wnt signaling can regulate a variety of diverse processes, including cell proliferation, differentiation, migration, polarity and asymmetric cell division.[3] Not surprisingly, the disruption of Wnt signaling has been linked to a number of human diseases and also hair loss.[4] Wnt pathways fall into two general categories: canonical and non-canonical Wnt signaling. Canonical Wnt signaling is often referred to as the Wnt/β-catenin pathway, as it happens when Wnt-stimulated signals trigger β-catenin-dependent transcriptional activation, whereas the non-canonical is referred to as the β-catenin-independent pathway. In the absence of Wnt, β-catenin is targeted by a destructive complex of proteins. Binding of Wnt to receptors activates cytosolic proteins, leading to the inhibition of the destructive protein complex and the stabilization of β-catenin. Accumulation of stabilized β-catenin in the presence of transcription factors results in their translocation into the nucleus to activate Wnt-responsive genes.[5]

Stem cells have the potential to treat an enormous range of diseases and conditions. Recent advances in the understanding of hair biology has led to the development of treatments that target angiogenesis,[6] androgen antagonism,[7] vasodilation through potassium channel opening,[8] 5-alpha reductase[9] inhibition and modulation of hair cycle[10] as non-surgical therapeutic strategies for hair growth promotion. Two of the most commonly used and accepted compounds for preventing hair loss are minoxidil and the 5a-reductase inhibitor, finasteride.[11] [12] However, as with the development of many nascent pharmacological strategies, the occurrence of adverse events generates barriers to successful therapeutic applications. The application of biological response modifiers and anti-androgens currently available for the management of hair loss have low success rates and are associated with adverse effects.[13] [14] Further, most available hair loss treatments focus on preventing or decreasing hair loss, with no existing treatment clinically proven to stimulate hair regrowth. Given the limited efficacy and related side effects of the available pharmaceutical based therapies there is a steadily growing demand for plant-based medicines and cosmetics. There are various plants and plant extracts used world-wide for hair care that are acclaimed to have hair growth promoting activity. Further, many of these botanical treatments use formulation strategies consisting of mixtures of herbal extracts designed to simultaneously target more than one of the proposed causes of hair loss.[15]

Over time the direct biological importance of hair for thermoregulation and protection has been largely lost in humans, but its effects on well-being remain significant. Hair loss can result either from a failure to regrow hair fibers from existing hair follicles, from factors within the milieu of the stem cell that impact follicular activity, or from the loss of hair follicles themselves. Hair loss is most frequently caused by a failure to activate existing hair stem cells during hair cycling and may be associated with aging in both males and females.[117] [16] This condition may be reversed if the stem cell activity is preserved and the causative factor impeding normal stem cell function is removed. Skin is a highly structured organ in which stem cell self-renewal, cell proliferation and differentiation are coordinated to maintain homeostasis. As an appendage of the skin the hair follicle sequentially and repeatedly cycles through phases of active fiber production (anagen), rapid phases of tissue regression (catagen) and regeneration (neogen) to a resting phase (telogen). Importantly, hair growth and hair follicle regeneration relies on the cyclical activation of stem cells.[17] The fact that the hair follicle undergoes periodic regeneration in the adult from a dedicated stem cell pool makes it an important model to study stem cell biology and consequently cell, tissue and organ regeneration.

Normally, hair follicles cycle between a growth stage (anagen), a degenerative stage (catagen), and a resting stage (telogen).[18] Scalp hairs have a relatively long life cycle: the anagen stage ranges from 2 to 6 years, the catagen stage ranges from a few days to a few weeks, and the telogen stage is approximately three months. Once the cycle is complete, it restarts and a new strand of hair begins to form. Hair growth is the cumulative, physical consequence of coordinated process of cellular proliferation and differentiation within a hair follicle.[19] During anagen, the hair follicle is highly active metabolically. The stem cells, which commit to the fate of a hair follicle, enter a period of massive proliferation that results in the formation of mature hair follicle.[20] The follicle comprises a dermal papilla at the base of the follicle with stem cells; and epidermal matrix cells surrounding the dermal papilla form the base of the hair shaft, which extends upwards from the papilla through the hair canal.[21] The matrix cells are the actively growing portion of the hair. At catagen, the matrix cells retract from the papilla, and other degenerative changes occur.[22] For example, the vessels and capillaries supplying blood and nutrients to the hair follicle shrivel and stop functioning. A column of epithelial cells pushes the keratinized proximal shaft of the hair upwards, and cell death occurs within the follicle.[21] The hair shaft is then shed from the scalp or other part of the body and the hair follicle enters telogen, the resting stage of the hair growth cycle.[24] The source of new cells necessarily required for a new cycle of a growing phase is generated from a pool of adult stem cells localized in each follicle.[5] It is suggested that hair follicles are formed only in the early stages of development, are finite in number and are not replaced. Thus, an increase in damaged or non-functioning hair follicles is generally associated with hair loss.[26] The rate of hair loss in both men and women is affected by advancing age, inherited genes, and an over-abundance of molecules that inhibit the hair cycle, a scarcity of molecules that promote the hair cycle or those that prevent the inhibition of the hair cycle. It has been found that hair follicle development and regeneration are regulated by the canonical Wnt/β-catenin signaling pathway where hair stem cells play a key role.[27]

During the active steady state, hair fiber production results from a finely, timely, and spatially tuned choreography of gene expression, which is highly sensitive to stimulatory and inhibitory signals. A number of signaling pathways,[28] cytokines,[29] hormones,[30 31] prostaglandins,[32] and growth factors are known to modulate the duration of the active steady state of the hair follicle.[33]

During the telogen phase, the follicle is under the influence of factors that would repress the onset of the neogen phase and factors that would trigger it. Specifically, a strong expression of bone morphogenetic protein (BMP) and fibroblast growth factor (FGF)-18 defines the refractory period, during which the neogen onset is prevented. The progressive increase in the production of the BMP antagonist noggin, Wnt/β-catenin pathway activators, and transforming growth factor (TGF)-β2 then reach a critical threshold that shifts the telogen follicle to a competency status, receptive to FGF-7, secreted by the nearby dermal papilla, and, ultimately, triggering the onset of the neogen phase.[34]

There remains a need in the art for safe and effective means of modulating stem cells and improving hair growth.

BRIEF SUMMARY OF THE INVENTION

This application relates to modulators of stem cells and one or more proteins in the Wnt pathway. This includes proliferators or reducers and activators or attenuators/inhibitors of stem cells and of one or more proteins in the Wnt pathway, including activators of one or more Wnt proteins, and compositions comprising the same. More particularly, it concerns the use of individual or combinations of botanical extracts from grapeseed (such as proanthocyanidins), skullcap, eclipta, Biotin or any combination thereof with or without Biotin or any analog thereof as either by topical, oral, injectable, intravenous, buccal, suppository, inhalable administration in humans, mammals and vertebrates or in nitro administration in tissue or cells and thus treat or prevent diseases related to signal transduction, such as osteoporosis and osteoarthropathy; osteogenesis imperfecta, bone defects, bone fractures, periodontal disease, otosclerosis, wound healing, craniofacial defects, oncolytic bone disease, traumatic brain injuries or spine injuries, brain atrophy/neurological disorders related to the differentiation and development of the central nervous system, including Parkinson's disease, strokes, ischemic cerebral disease, epilepsy, Alzheimer's disease, depression, bipolar disorder, schizophrenia; otic disorders like cochlear hair cell loss; eye diseases such as age related macular degeneration, diabetic macular edema or retinitis pigmentosa, cancer, aging and diseases related to differentiation and growth of stem cells, such as hair loss or alopecia, scalp disorders, vitiligo, canities and pigment disorders, hematopoiesis related diseases and tissue regeneration related diseases including psoriasis, eczema and rosacea. In particular, the disclosure provides Botanicals and Biotin or analogs thereof, that proliferate or reduce stem cell populations and activate or attenuate Wnt/beta-Catenin signaling in tissues expressing Wnt including amongst others, adipose, adrenal, artery, blood, bone marrow, bone, brain, breast, cervix, colon, esophagus, heart, intestine, kidney, liver, lung, muscle, ovary, pituitary, prostate, skin, spleen, testis, thyroid, uterus, thymus, and vagina.

The invention improves the function of the integumentary system with respect to skin formation, prevention of alopecia, promoting hair growth and regrowth in dormant hair follicles as well as improving the quality of nail growth. The invention also prevents demelanizing of hair (or canities) and promotes remelanization of hair. The invention also provides normal skin and hair growth under chronic inflammatory conditions that typically disrupt normal tissue growth. The invention by oral administration maintains normal or normalizes and reduces systemic health risk factors identified by Thyroid Stimulating Hormone, C-Reactive Protein, Blood Pressure, Cholesterol Profiles, Insulin, Glucose, serum creatinine, Hemoglobin, Glomuler Filtration Rates (GFR) in kidney and Low Density Lipoprotein (LDL), High Density Lipoprotein (HDL), Liver enzymes and red and white blood cells. The invention improves the aesthetic effect, appearance, overall wellness, depression and quality of life of humans.

DETAILED DESCRIPTION OF THE INVENTION

Definitions

Figure 1:
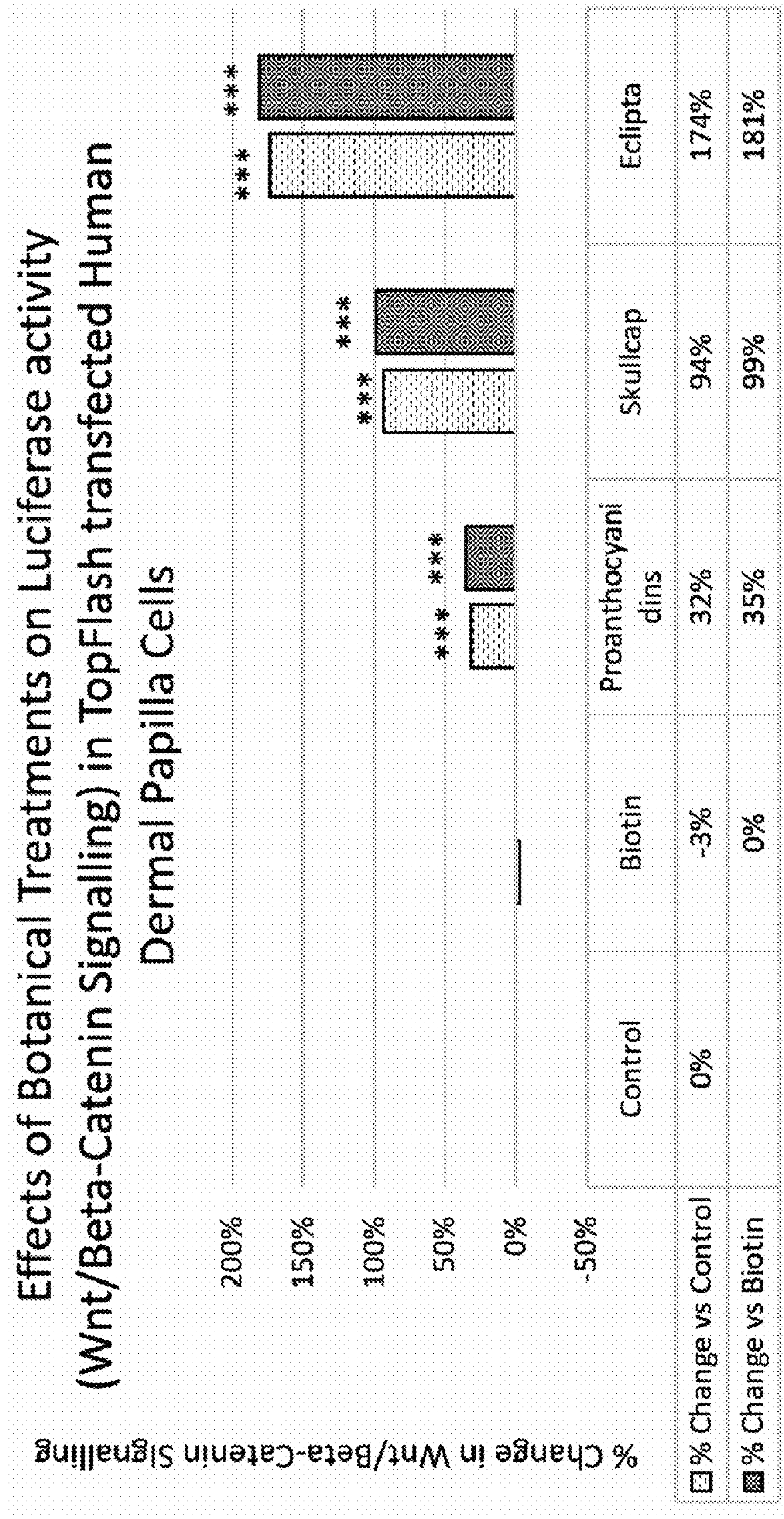
FIG. 1 is a bar graph showing the effects of Botanical Treatments on Wnt/beta-Catenin Signaling.

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. Furthermore, the phrases "less than about (a value)" or "greater than about (a value)" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc. Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a botanical extract" refers to one or more botanical extracts or at least one botanical extract. As such, the terms "a" (or "an"), "one or more" and "at least one" are used interchangeably herein. In addition, reference to "an extract" by the indefinite article "a" or "an" does not exclude the possibility that more than one of the extracts is present, unless the context clearly requires that there is one and only one of the extracts.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "treating" means one or more of relieving, alleviating, delaying, reducing, improving, or managing at least one symptom of a condition in a subject. The term "treating" may also mean one or more of arresting, retarding progression, delaying the onset (i.e., the period prior to clinical manifestation of the condition) or reducing the risk of developing or worsening a condition.

The term "regeneration" refers to the natural biological processes within a eukaryotic organism whereby cells, tissue or organs are replaced or regenerated, to restore or establish normal function.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or a formulation n that is sufficient to result in a desired clinical benefit after administration to a patient in need thereof.

As used herein, a "subject" can be a human, non-human primate, mammal, rat, mouse, cow, horse, pig, sheep, goat, dog, cat, and the like. The subject can be suspected of having or at risk for having a disease related to signal transduction, such as osteoporosis and osteoarthropathy; osteogenesis imperfecta, bone defects, bone fractures, periodontal disease, otosclerosis, wound healing, craniofacial defects, oncolytic bone disease, traumatic brain injuries or spine injuries, brain atrophy/neurological disorders related to the differentiation and development of the central nervous system, including Parkinson's disease, strokes, ischemic cerebral disease, epilepsy, Alzheimer's disease, depression, bipolar disorder, schizophrenia; otic disorders like cochlear hair cell loss; eye diseases such as age related macular degeneration, diabetic macular edema or retinitis pigmentosa, cancer, aging and diseases related to; dysregulation of Wnt/beta-Catenin or differentiation and growth of stem cells, such as hair loss or alopecia, scalp disorders, vitiligo, canities and pigment disorders, hematopoiesis related diseases and tissue regeneration related diseases including psoriasis, eczema and rosacea amongst others, are known to those of ordinary skill in the art.

"Mammal" includes humans and both domestic animals such as laboratory animals (e.g., mice, rats, monkeys, dogs, etc.) and household pets (e.g., cats, dogs, swine, cattle, sheep, goats, horses, rabbits), and non-domestic animals such as wildlife and the like.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially"

enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

"Proanthocyanidin or Proanthocyanidins" include procyanidin, procyanadin, anthocyanidin, anthocyanadin, anthocyanin, celphinidin, cyanidin, delphinidin, malvidin, pelargonidin, peonidin, petunidin. Proanthocyanidins are in a group of compounds called polyphenols and belong to a subclass of compounds called flavonoids that can be found in many plants, including; apples, pine bark, cinnamon, *aronia* fruit, cocoa beans, grape seed, grape skin, bilberry, cranberry, black currant, green tea, black tea, cocoa beans, *Quercus petraea* and *Q. robur* heartwood, agaf palm, field beans (*Vicia faba*), gallipoli rose, lingonberry, cranberry, black elderberry, chokeberry, black currant, blueberry, strawberry, persimmon, banana, carob bean, Chinese quince, chokeberries, rose hips, medlar, mulberry, plum, apricot, walnut, silverberry, pomegranate, triticale, sorghum, red cabbage, birch and *Ginkgo biloba.*

Any reference herein to the terms "grape seed", "grapeseed", "grape seed extract", "*Vitis vinifera*", "vitis", "Grapeseed proanthocyanidin extract" or "GSPE" means an extract or the component "Proanthocyanidin" in the singular or plural, its alternative names and sources.

Any reference to the term "extract", "plant extract" or "botanical extract" means the dry herb equivalent ("DHE") unless the quantity of the extract ratio or the extract standardization method is specified. When an extract standardization is used together with an extract ratio, the extract ratio is an approximation and the standardization takes priority in the extract specification. When there is an absence of a standardization in the practice of the art, the extract ratio of DHE is an acceptable approximation of dosage range.

The term "Botanicals" also includes Biotin in addition to normal reference of all plants and extracts in this disclosure.

Biology of Hair Loss

The hair follicle, as a mini-organ, has frequently been described in the scientific literature as the perfect organ to study and develop models for regenerative medicine in humans and mammals. Hair follicle stem cells are required to generate, maintain and renew the continuously cycling hair follicle, therefore making their study biologically and clinically important, from alopecia to carcinogenesis and regenerative medicine.[35, 36] The disclosures of this invention focus on the biology of the hair follicle and demonstrates direct beneficial application and effect to a range of cells, tissues and organs including hair.

Hair loss (alopecia) can significantly impact the quality of life of affected men and women,[37-38] especially when it affects the scalp.[39]

Alopecia is thought to affect about one-third of women at some time in their lives; among postmenopausal women, as many as two-thirds suffer hair thinning or bald spots.[40] The pattern of hair loss in women differs from male-pattern baldness. In women, the hair becomes thinner all over the head, followed by increasing diffuse hair loss, radiating from the top of the head.[40,41] A woman's hairline rarely recedes and women rarely become bald.[40,41]

Common alopecia types, like androgenetic alopecia (the most common type of hair loss in men and women), alopecia areata, and telogen effluvium have different clinical features and prognosis, but all are associated with psychological distress, potentially affecting self-esteem and personal relationships, especially in women.[37-42, 43] The hair loss caused by androgenetic alopecia usually begins between the ages of 12 and 40 years and is frequently insufficient to be noticed.[44] However, visible hair loss occurs in approximately one half of all persons by the age of 50 years.[44]

Hair loss can be related to one or more of the following factors: family history, hormonal changes and medial conditions, medications, radiation therapy to the head, and stressful events.[45]

The hair follicle is considered a unique structure that modulates its growth, in addition to extrafollicular signals, through the local production and signaling of hormones, neurotransmitters, neuropeptides and growth factors.[46]

Vitamins (e.g., vitamin B3), minerals, essential fatty acids (e.g., linoleic acid or α-linolenic acid deficiencies), and biotin can play a role in hair growth and hair loss, including alopecia. Deficiencies in iron, zinc, selenium, and vitamin D have been associated with hair loss or hair disorders, as reported in clinical and pre-clinical in vitro or in vivo studies.[47] While there is little research to show a benefit to supplementation in the absence of deficiency, a study showed that topically administered (vitamin B3 (niacin) derivatives increased hair fullness in females with androgen-dependent alopecia.[48]

Plants have been widely used for hair growth promotion since ancient times as reported in Ayurveda, Chinese and Unani systems of medicine.[49] Mechanistically, these phytochemicals appear to work by antagonizing androgen-mediated signaling, or by acting through non-androgen signaling pathways to promote anagen in hair follicles.[50] Examples of candidate herbs include extracts from the dried root of Sophoraflavescen,[51] *Ganoderma lucidum,*[52] and *Vitis vinifera.*[53] Additional herbs that are believed to reduce the rate of hair loss and at the same time stimulate new hair growth were discussed in Patel's et al. review.[49] However, Patel et al. concluded that more scientific evidences and documentation is desirable for promotion of herbal treatment to hair loss.[49] Evidence must be substantiated by reliable clinical trials with standardised material and formulation.[49]

Hair Follicles

Over time the direct biological importance of hair for thermoregulation and protection has been largely lost in humans, but its effects on well-being remain significant. Hair loss can result either from a failure to regrow hair fibers from existing hair follicles, from factors within the milieu of the stem cell that impact follicular activity, or from the loss of hair follicles themselves. Hair loss is most frequently caused by a failure to activate existing hair stem cells during hair cycling and may be associated with aging in both males and females.[117,54] This condition may be reversed if the stem cell activity is preserved and the causative factor impeding normal stem cell function is removed. Skin is a highly structured organ in which stem cell self-renewal, cell proliferation and differentiation are coordinated to maintain homeostasis. As an appendage of the skin the hair follicle sequentially and repeatedly cycles through phases of active fiber production (anagen), rapid phases of tissue regression (catagen) and regeneration (neogen) to a resting phase (telogen). Importantly, hair growth and hair follicle regeneration relies on the cyclical activation of stem cells.[55] The fact that the hair follicle undergoes periodic regeneration in the adult from a dedicated stem cell pool makes it an important model to study stem cell biology and consequently cell, tissue and organ regeneration.

Normally, hair follicles cycle between a growth stage (anagen), a degenerative stage (catagen), and a resting stage (telogen).[56] Scalp hairs have a relatively long life cycle: the anagen stage ranges from 2 to 6 years, the catagen stage ranges from a few days to a few weeks, and the telogen stage is approximately three months. Once the cycle is complete, it restarts and a new strand of hair begins to form. Hair growth is the cumulative, physical consequence of the coordinated process of cellular proliferation and differentiation within a hair follicle.[57] During anagen, the hair follicle is highly active metabolically. The stem cells, which commit to the fate of a hair follicle, enter a period of massive proliferation that results in the formation of mature hair follicle.[58] The follicle comprises a dermal papilla at the base of the follicle with stem cells; and epidermal matrix cells surrounding the dermal papilla form the base of the hair shaft, which extends upwards from the papilla through the hair canal.[59] The matrix cells are the actively growing portion of the hair. At catagen, the matrix cells retract from the papilla, and other degenerative changes occur.[60] For example, the vessels and capillaries supplying blood and nutrients to the hair follicle shrivel and stop functioning. A column of epithelial cells pushes the keratinized proximal shaft of the hair upwards, and cell death occurs within the follicle.[61] The hair shaft is then shed from the scalp or other part of the body and the hair follicle enters telogen, the resting stage of the hair growth cycle.[62] The source of new cells necessarily required for a new cycle of a growing phase is generated from a pool of adult stem cells localized in each follicle.[63] It is suggested that hair follicles are formed only in the early stages of development, are finite in number and are not replaced. Thus, an increase in damaged or non-functioning hair follicles is generally associated with hair loss.[64] The rate of hair loss in both men and women is affected by advancing age, inherited genes, and an over-abundance of molecules that inhibit the hair cycle, a scarcity of molecules that promote the hair cycle or those that prevent the inhibition of the hair cycle. It has been found that hair follicle development and regeneration are regulated by the canonical Wnt/β-catenin signaling pathway where hair stem cells play a key role.[65]

During the active steady state, hair fiber production results from a finely, timely, and spatially tuned choreography of gene expression, which is highly sensitive to stimulatory and inhibitory signals. A number of signaling pathways,[66] cytokines,[67] hormones,[68, 69] prostaglandins,[70] and growth factors are known to modulate the duration of the active steady state of the hair follicle.[71]

During the telogen phase, the follicle is under the influence of factors that would repress the onset of the neogen phase and factors that would trigger it. Specifically, a strong expression of bone morphogenetic protein (BMP) and fibroblast growth factor (FGF)-18 defines the refractory period, during which the neogen onset is prevented. The progressive increase in the production of the BMP antagonist noggin, Wnt/β-catenin pathway activators, and transforming growth factor (TGF)-β2 then reach a critical threshold that shifts the telogen follicle to a competency status, receptive to FGF-7, secreted by the nearby dermal papilla, and, ultimately, triggering the onset of the neogen phase.[72]

Wnt/β-Catenin Pathway

It is clear from the above that the complex and rhythmic behavior of the human hair follicle is under the control of multiple, intricate pathways with many opposing influences.

Stem cells are mainly characterized by the properties of self-renewal and the potency to differentiate into diverse cell types. Studies have demonstrated that these properties are regulated by different growth factors including members of the Wnt/β-catenin protein family. In hair follicles, stem cells are "quiescent," meaning they are normally inactive, but they quickly activate during a new hair cycle driving new hair growth. Hair follicle stem cells remain dormant during telogen for a few weeks, before proliferating during anagen.[73] Therefore, the stem cells give the follicle its regenerative capacity, allowing it to cycle through its growth phases. The quiescence of hair follicle stem cells is regulated by many factors. In certain cases they fail to activate, which is what causes hair loss. Wnt proteins are secreted glycoproteins that can activate different intracellular signaling pathways. Recent studies have suggested that hair loss occurs when the supply or the activity of hair follicle stem cells is exhausted. How they retain their stemness, or ability to self-renew and differentiate appears to be intimately related to Wnt/β-catenin activity.[74]

In mammals, Wnt/β-catenin signaling features prominently in stem cells. The interactions between Wnt ligands and their receptors result in the activation of various intracellular signaling cascades that can be cross-connected or act independently. Depending on the pathway activated, Wnt signaling can regulate a variety of diverse processes, including cell proliferation, differentiation, migration, polarity and asymmetric cell division.[75] Not surprisingly, the disruption of Wnt signaling has been linked to a number of human diseases and also hair loss.[76] Wnt pathways fall into two general categories: canonical and non-canonical Wnt signaling. Canonical Wnt signaling is often referred to as the Wnt/β-catenin pathway, as it happens when Wnt-stimulated signals trigger β-catenin-dependent transcriptional activation, whereas the non-canonical is referred to as the β-catenin-independent pathway. In the absence of Wnt, β-catenin is targeted by a destructive complex of proteins. Binding of Wnt to receptors activates cytosolic proteins, leading to the inhibition of the destructive protein complex and the stabilization of β-catenin. Accumulation of stabilized β-catenin in the presence of transcription factors results in their translocation into the nucleus to activate Wnt-responsive genes.[77]

Stem cells have the potential to treat an enormous range of diseases and conditions. Recent advances in the understanding of hair biology has led to the development of treatments that target angiogenesis,[78] androgen antagonism,[79] vasodilation through potassium channel opening,[80] 5-alpha reductase[81] inhibition and modulation of hair cycle[82] as non-surgical therapeutic strategies for hair growth promotion. Two of the most commonly used and accepted compounds for preventing hair loss are minoxidil and the 5a-reductase inhibitor, finasteride.[83 84] However, as with the development of many nascent pharmacological strategies, the occurrence of adverse events generates barriers to successful therapeutic applications. The application of biological response modifiers and anti-androgens currently available for the management of hair loss have low success rates and are associated with adverse effects.[85 86] Further, most available hair loss treatments focus on preventing or decreasing hair loss, with no existing treatment clinically proven to stimulate hair regrowth. Given the limited efficacy and related side effects of the available pharmaceutical based therapies there is a steadily growing demand for plant-based medicines and cosmetics. There are various plants and plant extracts used world-wide for hair care that are acclaimed to have hair growth promoting activity. Further, many of these botanical treatments use formulation strategies consisting of mixtures of herbal extracts designed to simultaneously target more than one of the proposed causes of hair loss.[87]

Botanicals of the Present Disclosure

The botanical compositions or combinations of the present disclosure can be useful for activating the Wnt/beta-Catenin pathway. Further, the botanical compositions or combinations of the present disclosure can be useful for treating various diseases and conditions including, but not limited to, hair loss.

In one embodiment of the present disclosure, the compositions or combinations comprise one or more botanical extracts.

The botanical extracts of the present disclosure can, alone, be useful for treating various diseases and conditions including, but not limited to, hair loss. In some embodiments, the condition is male or female hair loss.

In one embodiment the present disclosure provides the botanicals selected from:

Biotin is a water-soluble B-vitamin,[88] also called vitamin $B_7$ and formerly known as vitamin H or coenzyme R.[89]

Biotin serves as a coenzyme for carboxylase enzymes, involved in the synthesis of fatty acids, isoleucine, and valine, and in gluconeogenesis.[90] Biotin cannot be synthesized by mammalian cells and must be obtained from exogenous sources. Biotin is widely found in food, and good dietary sources include egg yolk, liver, whole-grain cereal, and some vegetables.

Biotin deficiency can be caused by inadequate dietary intake or inheritance of one or more inborn genetic disorders that affect biotin metabolism.[91 92] Subclinical deficiency can cause mild symptoms, such as hair thinning or skin rash typically on the face.[93] Signs of overt biotin deficiency include hair loss (alopecia) and a scaly red rash around the eyes, nose, mouth, and genital area. Neurologic symptoms in adults have included depression, lethargy, hallucinations, numbness and tingling of the extremities, ataxia, and seizures.[94]

Water-soluble biotin is an essential cofactor to enzymes in intermediary metabolism and a key regulator of gene expression. Biotin functions as a cofactor required for the biological activity of five known mammalian biotin-dependent carboxylases. The covalent attachment of biotin to the apocarboxylase is catalyzed by the enzyme, holocarboxylase synthetase (HCS). HCS catalyzes the post-translational biotinylation of histones, significant for DNA packaging in eukaryotic nuclei.[95] Both acetyl-Coenzyme A (CoA) carboxylase 1 (ACC1) and acetyl-CoA carboxylase 2 (ACC2) catalyze the conversion of acetyl-CoA to malonyl-CoA using bicarbonate and adenosine triphosphate (ATP); malonyl CoA generated via ACC1 is a rate-limiting substrate for the synthesis of fatty acids in the cytosol, and malonyl CoA generated via ACC2 inhibits Carnitine palmitoyltransferase 1 (CPT1), an outer mitochondrial membrane enzyme important in fatty acid oxidation.[96] Pyruvate carboxylase is a critical enzyme in gluconeogenesis.[97] Methylcrotonyl-CoA carboxylase catalyzes an essential step in the catabolism of leucine, an essential branched-chain amino acid[98] Propionyl-CoA carboxylase produces D-malonylmalonyl-CoA from propionyl-CoA, a by-product in the β-oxidation of fatty acids with an odd number of carbon atoms. The conversion of propionyl-CoA to D-malonylmalonyl-CoA is also required in the catabolic pathways of two branched-chain amino acids (isoleucine and valine), methionine, threonine, and the side chain of cholesterol[99] All are biotin-containing enzymes required for these metabolic actions. To date no studies have demonstrated a direct impact of biotin on stem cells.

*Scutellaria baicalensis* (Chinese skullcap) is a species of flowering plant belonging to Lamiaceae family. *Sc. baicalensis* has been shown to have many pharmacological effects including antipyretic, hepatoprotective, antihypertensive, diuretic, and antibiotic activities. It is mildly sedating and also used to treat dysentery and chronic hepatitis.[100 101 102 103] *Sc. baicalensis* has distinct effects in the treatment of inflammatory diseases; it alleviates inflammation by decreasing the expression of interleukin (IL)-1b, IL-6, and IL-12, and the production of tumor necrosis factor (TNF)-α and soluble intercellular adhesion molecule-1 (ICAM-1).[104 105] Skullcap is frequently used in traditional medicine in China. Skullcap contains many identified constituents.[106] Studies on its active ingredients revealed that the total flavonoids extracted from the stem and leaf, mainly including scutellarin, baicalin, baicalein, wogonin and chrysin, exhibited a series of pharmacological effects such as anti-inflammation, prevention from myocardial damage induced by ischemia-reperfusion, and improved cerebral ischemia.[107] Skullcap also prevented apoptosis by increasing the anti-apoptotic protein activity, demonstrating indirect antioxidant effects.[108] Flavones from skullcap attenuated oxidant stress and protected neuronal cells from lethal oxidant damage.[109] Skullcap also prevented apoptosis by increasing the Bcl-2/Bax (B-cell lymphoma 2/Bcl-2 associated X protein) ratio and phosphorylating Bcl-2.[110] It was suggested that baicalin could be a key template for the development of therapeutic agents to selectively modulate inflammatory responses and cellular apoptosis in the central nervous system (CNS). It has been reported that skullcap flavonoids also inhibit nitric oxide (NO) production.[111] A recent study demonstrated that extracts of *Sc. baicalensis* and its identified active constituent baicalin, inhibited nuclear translocation of the androgen receptor stimulated by dihydrotestosterone in human dermal papilla cells. Both the extract and baicalin enhanced proliferation of human dermal papilla cells in vitro, inhibited androgen activation signaling and promoted dermal papilla cell proliferation, suggesting that they could be used as active ingredients for treating androgen-associated disorders, such as androgenetic alopecia.[112] The flavonoid wogonin, one of the major bioactive compound of *Sc. baicalensis* has been reported to have a variety of bioactive effects including antioxidant, anti-inflammatory, and anticancer activities.[113 114 115] Moreover, neuroprotective effects have also been ascribed to wogonin in different nerve injury models.[116 117] In a study investigating the ability of wogonin to promote retinal neuron-like differentiation of bone marrow stem cells, wogonin decreased the expression of Notch-I signaling proteins, reduced the expression of stem cell markers, and increased markers of mature retinal neurons, bipolar cells and photoreceptors in treated bone marrow stem cells.[118] In a study, it was demonstrated that wogonin downregulates OVA-induced Th2 immune responses, especially IgE and IL-5 production suggesting that it may be applied as a preventive and therapeutic agent for IgE- and IL-5-mediated allergic disorders such as food allergy, atopic dermatitis, and asthma.[119]

*Eclipta alba* (L.) Hassk. (also known as *Eclipta prostrata* Roxb.)

*Eclipta* belongs to the Asteraceae family and is commonly known as false daisy, is a species of plan in the sunflower family.[120] The plant has traditional uses in Ayurveda. *E. alba* contains coumestans (wedelolactone and demethylwedelolactone), polypeptides, polyacetylenes, thiophene derivatives, steroids, sterols, triterpenes, and flavonoids.[121] Ethnomedicinal uses of the plant and plant parts have been reported from the Indian subcontinent. Reports indicate that although there are a variety of diseases treated with the plant or plant parts, the major uses are limited to treatment of gastrointestinal disorders, respiratory tract disorders, fever, hair loss and graying of hair, liver disorders and skin disorders.

Antihepatotoxic activity of the plant has been reported implicating the coumestans constituents as the possible components behind the protective effect.[122] Studies have also shown a significant stimulatory effect on liver cell regeneration.[123] Further, Hepatitis C virus (HCV) inhibitory activity has been reported for *E. alba* extract. Phytochemical analysis of the extract revealed the presence of three compounds, namely, wedelolactone, luteolin, and apigenin. These compounds exhibited dose-dependent inhibition of HCV in vitro, and in a cell culture system.[124] Additional compounds of *Eclipta alba* extract have been found and many have shown to have anti-oxidant and anti-cancer activity as identified in Table 1[125]

TABLE 1

Compounds found in Eclipta. Anti-cancer and anti-oxidant activities.

| Compounds | Anticancer activity (AC) | Antioxidant activity (AO) |
|---|---|---|
| 2-methylbutanal oxime | NA | NA |
| Catechol | YES | YES |
| Uracil | YES | YES |
| Phenyl ethylamine | NA | NA |
| Nicotinic acid | YES | YES |
| 4-hydroxybenzoic acid | YES | YES |
| 3,4-dihydroxybenzoic acid | YES | YES |
| Dihydrocarveol | NA | NA |
| L-nicotene | NA | NA |
| Gallic acid | YES | YES |
| Catechol derivative | YES | YES |
| Caryophyllene oxide | NA | NA |
| Coumestan | YES | YES |
| Apigenin | YES | YES |
| Butein | YES | YES |
| α-terthienyl methanol | YES | NA |
| Indolylmethyl glucosinolate | NA | NA |
| Luteolin | YES | YES |
| Testoterone | NA | NA |
| 2-Terthiophene-5-carboxylic acid | NA | NA |
| Demethylwedelolactone | YES | YES |
| Wedelolactone | YES | YES |
| Tyramine β xantine | NA | NA |
| Gallic acid hexoxide | NA | NA |
| Quercetin derivative | YES | YES |
| Catechin derivative | YES | YES |
| 16-methoxytabersonine | NA | NA |
| Stigmasterol | YES | YES |
| β-sitosterol | YES | YES |
| β-amyrin | NA | YES |
| Hypophyllanthin | YES | YES |
| Apigenin-7-O-glucoside | YES | YES |
| Epicatechin | YES | YES |
| Quercetin-3-rhamnoside | YES | YES |
| Cynaroside | YES | YES |
| Demethylwedelolactone 7-glucoside | YES | YES |
| Galloyl-isorhamnetin | NA | NA |
| Echinocystic acid | YES | NA |
| Caulophyllogenin | NA | NA |
| Myoinositol | YES | YES |

NA = Not Applicable.[126]

Transaminase (AST), alkaline phosphatase (ALP), lactate dehydrogenase (LDH), and gamma-glutamyl transferase (GGT) as well as changes in serum proteins, bilirubin, cholesterol, and triglycerides were restored to normal levels with the leaf powder.[127] The beneficial effects of the plant in diabetes have been reported. In alloxan-diabetic rats, oral administration of a leaf suspension of *E. alba* resulted in significant reductions in blood glucose, glycosylated hemoglobin HbA1c, a decrease in the activities of glucose-6 phosphatase and fructose 1,6-bisphosphatase, and an increase in the activity of liver hexokinase, all of these being beneficial for amelioration of hyperglycemia and other diabetes-related complications.[128] Further, the antioxidant and protective effect of a water extract of *E. alba* against ultraviolet irradiation-induced damage has been investigated. The extract had a potent effect in scavenging superoxide radicals and chelating ferrous ion ($Fe^{2+}$). The protective effect against skin cell damage was attributed to a synergistic effect between chlorogenic acid and other active components present in the extract.[129] The anti-inflammatory effect of the plant was evaluated using histamine and serotonin induced paw edema in rats. The results indicated potent anti-inflammatory activity.[130] The aqueous extract of leaves of *E. alba* has been examined for its memory enhancing quality in rats to evaluate transfer latency (TL) on an elevated plus maze. The extract produced a significant decrease in TL in rats indicating an extract-induced improvement in cognitive functions, attributable to the presence of luteolins in the extract.[131] Extracts of *E. alba* have been tested in animal models for promoting hair growth activity. Topically applied extracts significantly reduced hair growth time and promoted a greater number of hair follicles in anagenic phase compared to non-treated control animals.[132] Further, a dose-dependent transition of telogen to anagen phase of hair growth was observed following *E. alba* extract treatment in a rodent model of hair growth.[133] One study demonstrated the protective effects of wedelolactone against the ROS-induced damage of mesenchymal stem cells treated in a 3-(4,5-dimethylthiazol-2-yl)-2,5-diphenyl (MTT) assay.[134]

*Vitis vinifer* (Grapeseed). Grapevines are classified into the genus *Vitis*. A single *Vitis* species, *V. vinifera*, originated in Europe and has been thoroughly studied. Approximately 34 species have been characterized in North America and Central America, whereas more than 30 species are native to China.[135] Grapeseed proanthocyanidin extract (GSPE) possesses a broad spectrum of therapeutic properties,[136] and is a popular herbal supplement with patients suffering from cardiovascular disease. Interest in grapeseed as a possible cardioprotective agent peaked following demonstration of the "French paradox," a positive correlation between the high intake of saturated fat and increased wine consumption, but a reduced risk of ischemic heart disease (IHD).[137] In GSPE, the main polyphenolic oligomeric and polymeric proanthocyanidins are catechin, epicatechin, epicatechin gallate and procyanidin B2.[138] Among these proanthocyanidins, procyanidin B2 has been shown to be the most effective compound in trapping oxygen free radicals.[139] A more recent study examining the delivery of natural polyphenols by polymeric nanoparticles demonstrated an improvement in the resistance of endothelial progenitor cells to oxidative stress.[140]

To date, studies have been conducted to examine the effect of botanicals on Wnt signaling in cancer.[141] Further, the effect of various botanical extracts on stem cell activity has been elucidated.[142] However, to date, no studies have described the mechanism of action of how botanical extracts stimulate stem cell activation. In addition, no studies have described how botanicals known to stimulate hair growth impart their growth-promoting effect on hair follicle cells. Therefore, a more clear understanding of the mechanisms by which these natural therapies carry out their actions may lead to improved treatments for hair loss but may also uncover novel uses and functions in other stem cell populations implicated in other disease states.

To this end, we examined the effect of various botanical extracts, and the synergistic effect of various combinations of botanical extracts, on the stimulation of dermal papilla stem cells and attempted to elucidate the mechanism of action by which they carried out their effect.

The disclosure provides for botanical extracts that proliferate or reduce stem cell populations and activate or attenuate Wnt/beta-Catenin signaling in tissues expressing Wnt including amongst others, adipose, adrenal, artery, blood, bone marrow, bone, usbrain, breast, cervix, colon, esophagus, heart, intestine, kidney, liver, lung, muscle, ovary, pituitary, prostate, skin, spleen, testis, thyroid, uterus, thymus, and vagina.

Tissue Regeneration

The invention comprises a method of regenerating healthy tissues. The invention proliferates stem cells and activates stem cells by upregulating the Wnt/β-catenin pathway to proliferate and differentiate into tissue cells by also regulating pathways including; BMP, mTORC1, PKC, PPARγ, Shh. The invention further regulates multiple molecular pathways within the tissues and cells to improve the environment for normal development and function of the cells, tissues and organs. One example of improving the cell and tissue environment is by regulating immune and inflammatory molecular pathways elevated by the disease such as; COX, INF-α, ING-γ, Interleukins, NF-κB, Prostaglandins, TNF-α and TGF-β. The invention also regulates a variety of growth factors including; FGF-7, FGF-18, HGF, IGF, KGF. Regulating VEGF ensures adequate angiogenesis for blood flow. The invention also primes the cells and tissues with nutrients to support metabolic function and neutralizing effects of free radicals by regulating SOD and peroxidase. In particular, the invention has demonstrated regeneration of the integumentary system and its appendages in diseased and non-diseased tissues in human subjects. The invention has also demonstrated maintenance or improvement of principal health markers and risk factors in humans experiencing chronic and degenerative aging conditions using various compositions of the invention, which include Botanicals, Vitamins, Minerals, Amino-acids and various cofactors for oral and/or topical administration.

The invention improves the function of the integumentary system with respect to skin formation, prevention of alopecia, promoting hair growth and regrowth in dormant hair follicles as well as improving the quality of nail growth. The invention also prevents demelanizing of hair (or canities) and promotes remelanization of hair. The invention also provides normal skin and hair growth under chronic inflammatory conditions that typically disrupt normal tissue growth. The invention by oral administration maintains normal or normalizes and reduces systemic health risk factors identified by Thyroid Stimulating Hormone, C-Reactive Protein, Blood Pressure, Cholesterol Profiles, Insulin, Glucose, serum creatinine, Hemoglobin, Glomuler Filtration Rates (GFR) in kidney and Low Density Lipoprotein (LDL), High Density Lipoprotein HDL, Liver enzymes and red and white blood cells. The invention improves the aesthetic effect, appearance, overall wellness, depression and quality of life of humans.

Hair Proliferation

The hair follicle, as a mini-organ, has frequently been described in the scientific literature as the perfect organ to study and develop models for regenerative medicine in humans and mammals. Hair follicle stem cells are required to generate, maintain and renew the continuously cycling hair follicle, therefore making their study biologically and clinically important, from alopecia to carcinogenesis and regenerative medicine.[143] [144] The disclosure of this invention focuses on the biology of the hair follicle and demonstrates direct beneficial application and effect to a range of cells, tissues and organs other than hair.

Often taken for granted, hair is a far more complex appendage of the integumentary system than it appears. Culturally, hair plays a vital role in the appearance of both men and women, creates gender identity, supports thermoregulation, and helps to transmit sensory information. By the second trimester of in-utero development, all of the hair follicles a human will ever have during the course of their lives will have been developed and they do not generate new ones.[145] In general, the human body will have a total of 5 million hair follicles, one million on the head, with one hundred thousand of those follicles residing on the scalp.[145]

Anatomically, hair has two distinct structures—the follicle which resides in the epidermis and dermis of the skin, and the shaft which is what is visible above the scalp.[146] The follicle contains several distinct cellular layers that have separate functions. At the base of the follicle is the papilla, which contains capillaries that nourish the cells. The hair bulb, the distal portion of the follicle, surrounds the papilla and is the living part of the hair.[146] The cells of the bulb regenerate remarkably faster than any other cell in the body and divide every 24 to 72 hours, permitting hair on the scalp to grow about 0.3 to 0.4 mm/day or about 6 inches per year.[146] The hair shaft that is visible above the scalp is not a living structure but is a layered structure made of a hard protein called keratin.[146] The development of the hair shaft is dependent upon the normal biological activity of the cells of the follicle. As part of the integumentary system, hair, its appearance and growth, is affected by a myriad of chemical messengers circulating within the body, the proper functioning of other systems in the body, and has demanding nutrient and energy requirements.

Hair growth involves a life-long cyclic transformation of the cells of the follicle from a resting (telogen) phase to a growth (anagen) phase in which a rapid proliferation of follicular cells leads to an elongation and thickening of the hair shaft, followed by a regression (catagen) phase.[147] At any given time, a random number of hairs will be in one of these three stages of growth and shedding. Anagen is the active phase of the hair when the cells in the root of the hair are dividing rapidly. During this phase the hair grows about 1 cm every 28 days. Scalp hair stays in this active phase of growth for two to six years. The catagen phase is a transitional stage, and about 3% of all hairs are in this phase at any time. This phase lasts for about two to three weeks. Telogen is the resting phase and usually accounts for 6% to 8% of all hairs. This phase lasts for about 100 days when the hair follicle is completely at rest and the hair shaft is completely formed.[147]

Biomarkers Influencing Hair Growth

The cycles of growth of each follicle (and thus each hair shaft) therefore, consist of creation followed by self-destruction. During each new cycle the follicle is built anew from raw materials. Similar to other tissues, hair follicle regeneration relies on the cyclical activation of stem cells.[148] Ultimately, the production of the hair shaft results from a tightly choreographed expression of genes that are highly sensitive to stimulatory and inhibitory signals. The recent proliferation of research into the functioning of hair follicles has demonstrated that hair growth can be affected by a number of signalling pathways[149], cytokines[150], hormones[151,152], prostaglandins[153], and growth factors[154].

Figure 3:
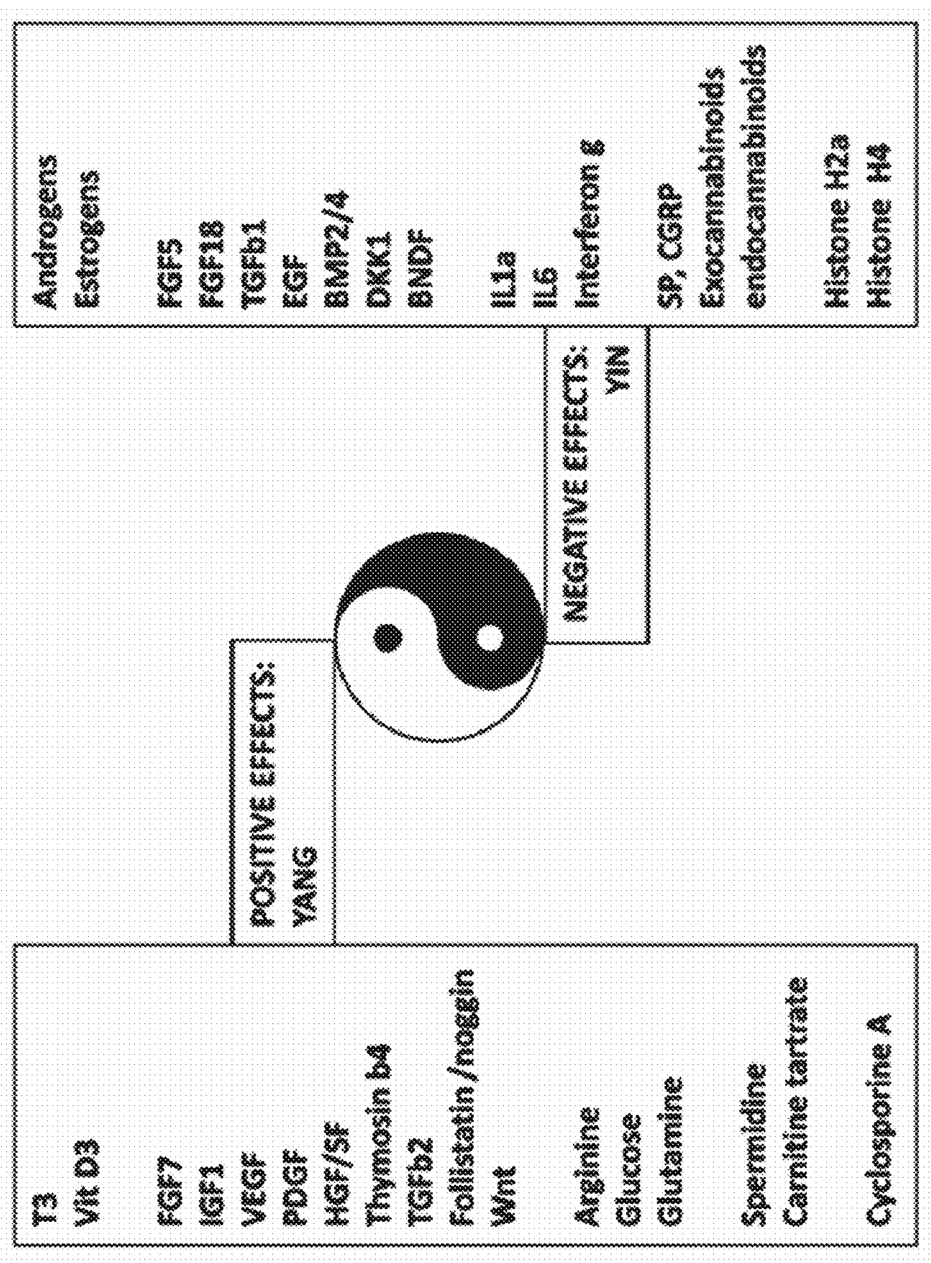
FIG. 3 shows stimulatory and inhibitory factors having positive or negative effects on hair growth and cycling.

FIG. 3 shows stimulatory and inhibitory factors having positive or negative effects on hair growth and cycling.[155]

Scientific evidence has shown that dihydrotestosterone (DHT) can shrink hair follicles which leads to hair loss.[156] Therefore, therapeutic approaches that inhibit the formation of DHT, by targeting those enzymes that convert testosterone to DHT, should prevent hair loss, or at least slow it down. Research has demonstrated that during hair cycling in animal models, there occurs a change in the number, location, and activation of various types of immune system cells suggesting a relationship between the immune system and hair growth cycle.[157] Further, observations have demonstrated that when the hair follicle bulb is attacked by immune cell infiltration, severe forms of hair loss can occur.[157] The cells of the immune system are under the influence, and respond to the presence of chemical messengers known as hormones and cytokines—which can be produced by other cells of the body or the immune system cells themselves. For example, prostaglandins are a diverse group of fatty acids that regulate a variety of functions, including inflammation, can dramatically influence hair growth. The hair follicle is endowed with a full prostaglandin metabolism and a complex network of prostaglandin receptors.[158] Recent data suggest that PGD2 can trigger anagen to catagen transition.[159] Hair follicle morphogenesis depends on signaling pathways interplay between different hair follicle cells. Pathways such as Wnt, Shh, Notch, BMP (and others) play an essential role in follicular induction and differentiation.[160] The Wnt pathway plays an essential role during hair follicle induction, Shh is involved in morphogenesis and late stage differentiation, Notch signaling determines stem cell fate while BMP is involved in cellular differentiation.[160] Recent investigations have demonstrated that the up-regulation of chemical messengers such as β-catenin, Wnts, FGF-7 (fibroblast growth factor) and the down-regulation of FGF-18 can dramatically influence hair growth.[160, 145]

Figure 4:
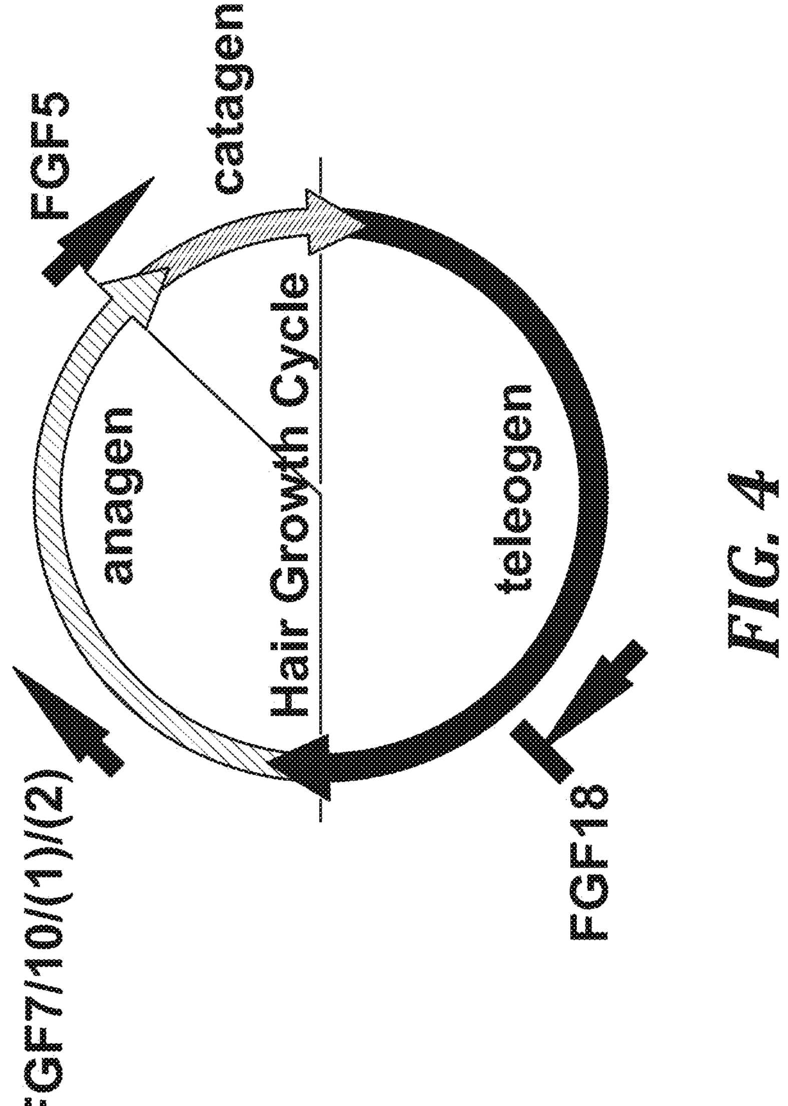
FIG. 4 shows a proposed model of FGF signaling in the regulation of the hair growth cycle.

FIG. 4 shows a proposed model of FGF signaling in the regulation of the hair growth cycle in which FGF18 signaling maintains telogen and prevents transition to the anagen phase. FGF5 signaling induces transition to catagen and FGF7, FGF10 and perhaps FGF1 and FGF2 promote anagen.[161]

In this paradigm, during the telogen phase, the follicle is under the influence of factors that would repress the onset of a new growth phase. As an example, a strong expression of bone morphogenetic protein (BMP) and FGF-18, which characterizes the refractory period, onset of hair growth is prevented. The progressive increase in the production of the BMP antagonist noggin, Wnt/beta-Catenin pathway activators, and various growth factors reaches a critical threshold that shifts the telogen follicle to a status receptive to FGF-7, secreted by the nearby dermal papilla, that ultimately, triggers the onset of a new growth phase[161].

Hair growth among individuals is therefore dependent, not only upon gender and age, as we are aware, but also upon genetics, hormones, an intricate play between signaling molecules, growth factors and normal biology. It has become clear that the complex and rhythmic behaviour of the human hair follicle is under the control of multiple intricate pathways with opposing influences and not upon a single target molecule. From a pathological perspective this implies that there is no single cause of thinning hair. As mentioned, hair cells are one of the fastest reproducing cells in the body, which means they are also very sensitive to even the smallest changes in health or their immediate environment. The activity of the hair follicle is, therefore, impacted by both intrinsic and extrinsic factors. As a result, proper nutrition, general health, hormone balance, appropriate blood flow, the proper health and functioning of bodily systems such as the immune, circulatory, and integumentary systems, and the appropriate balance of various endogenous substances play an important role in maintaining and restoring health to hair.

It therefore, makes little sense to develop a hair therapy with a focus on a single target or pathway and expect superior efficacy. Current hair treatment strategies are symptomatic and nonspecific. Most commonly available pharmaceutical-based and botanical-based formulations, target a single pathway (or a limited number of pathways) using high-dose active ingredients leading to limited effectiveness and unwanted side effects, minoxidil, finasteride are commercially available to slow hair loss and to facilitate hair regrowth. Minoxidil, which functions as a vasodilator facilitates hair growth due to its nutrient-supplying and potassium channel-opening activities.[162] Minoxidil effectiveness disappears within months after discontinuation of treatment.[162] By comparison, finasteride, are synthetic anti-androgens, inhibiting type II 5-α reductase, an enzyme that converts testosterone to dihydrotestosterone (DHT) in the papilla cells, have both being known to have significant side-effect profiles.[163]

Furthermore, it is important to realize that despite all efforts to correct an inherent deficiency affecting normal hair growth, no therapy will be effective if the metabolic requirements of follicle cells for optimal hair growth are not satisfied. Proper nutrition is important for all aspects of health care. Trials have indicated that correct nutrition is instrumental in healthy hair growth, and conversely, many deficiencies correlate with hair loss.[164] Despite having optimal health, if the "building blocks" for proper growth and development of hair are not available the structure is most likely to be affected. The necessary "building blocks" include vitamins, minerals (trace elements), amino acids, fatty acids and molecules such as antioxidants that impact the presence of damaging free radicals.[165]

The living part of hair is under the scalp's skin where its root is housed within its follicle. The follicle's sole purpose is to produce the hair shaft made predominantly of the protein keratin. The vitamins, minerals and amino acids crucial to the metabolic pathways involved in keratin protein production requires adequate blood flow delivering the necessary nutrients and oxygen to the hair cells. In fact, hair loss is exacerbated by a deficient blood supply.[165] This optimal environment can be achieved with formulations that deliver the necessary nutrients for hair growth, and that can stimulate angiogenesis (the generation of new blood vessels). Numerous studies demonstrate that the up-regulation of a molecule known as VEGF (vascular endothelial growth factor) improves blood flow by stimulating angiogenesis.[166] Interestingly, studies in normal hair biology demonstrate that when hair follicles leave telogen and enter anagen, angiogenesis is stimulated.[166]

With this vast body of knowledge in the scientific literature describing the biology of the hair follicle, the paradigm for exogenous treatments of hair loss are typically focused around single molecule or single target action pharmaceutical formulations, light emitting devices or nutrition applied topically or orally. Furthermore, the arts of traditional medicines have provided various botanical formulations for many diseases and disorders including those of skin, scalp and hair. These botanical extracts used in traditional medicines are a growing body of literature describing the biological mechanisms of action and regulation of molecular activity in human cells, tissues and organs. Notwithstanding this knowledge in the literature, there has not been a disclosure that describes an embodiment of either a comprehensive biomolecular strategy, nor a formulation that targets a comprehensive biomolecular targeting strategy of regenerating tissues or organs or more specifically the regeneration of the hair follicle, as a mini-organ along with hair regrowth, and therefore, provides a regenerative medicine embodiment in humans, mammals and vertebrates.

Biomolecular Strategy for Regenerating the Hair Follicle as a Mini-Organ and Hair Regrowth The formulations in this disclosure have been developed positively influence dermal papillary cells and stem cells by modulating what the most recent research in hair biology suggest are the important players in hair health such as the Wnts/β-catenin and BMP pathways, cell death pathways, androgenic mediators such as DHT and 5α-reductase, growth factors such as FGF (7 and 18), HGF, IGF and KGF, immune mediators such as prostaglandin D2, INF, TNF, interleukins, and factors that improve microcirculation of the follicle environment such as VEGF. Further, the designed formulations provide the proper nutrition required as a foundation for healthy hair growth (scalp and follicular health) —amino acids, vitamins and trace minerals for proper protein production and tissue development and anti-oxidation necessary to scavenge the damage caused by free radical production.

For example, Astragaloside IV, a major component of *Astragalus membranaceus*, is a cycloartane triterpene saponin known to have an anti-apoptotic (cell death) effect was examined for its effects against hair loss in a mouse model.[167]

Figure 5A:
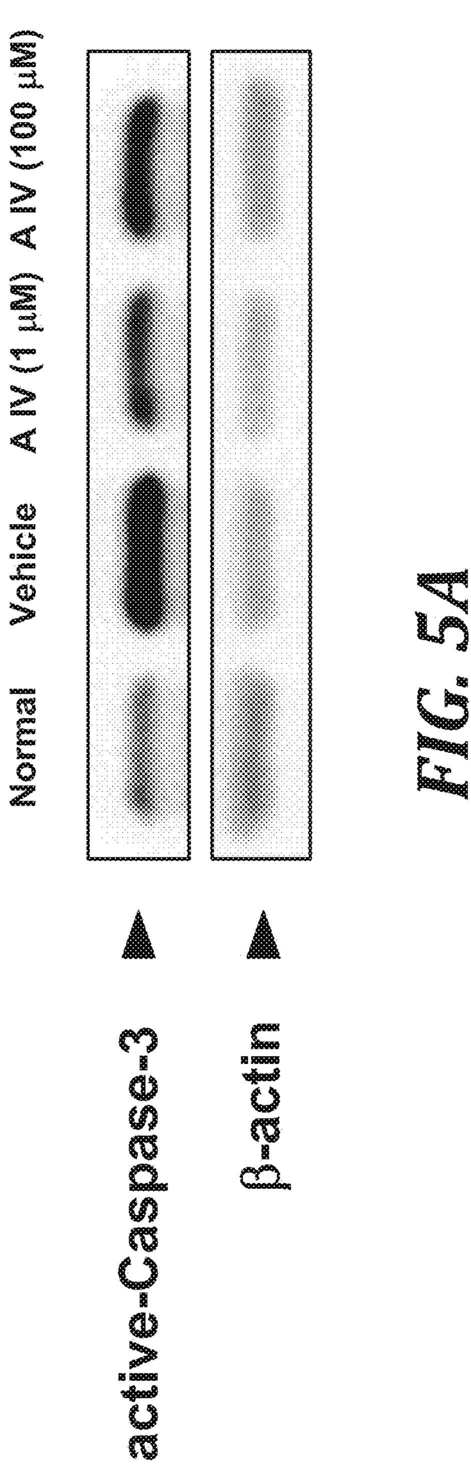
FIG. 5A is an electrophoretic gel showing effects on Caspase 3 and Beta-Actin.
Figure 5B:
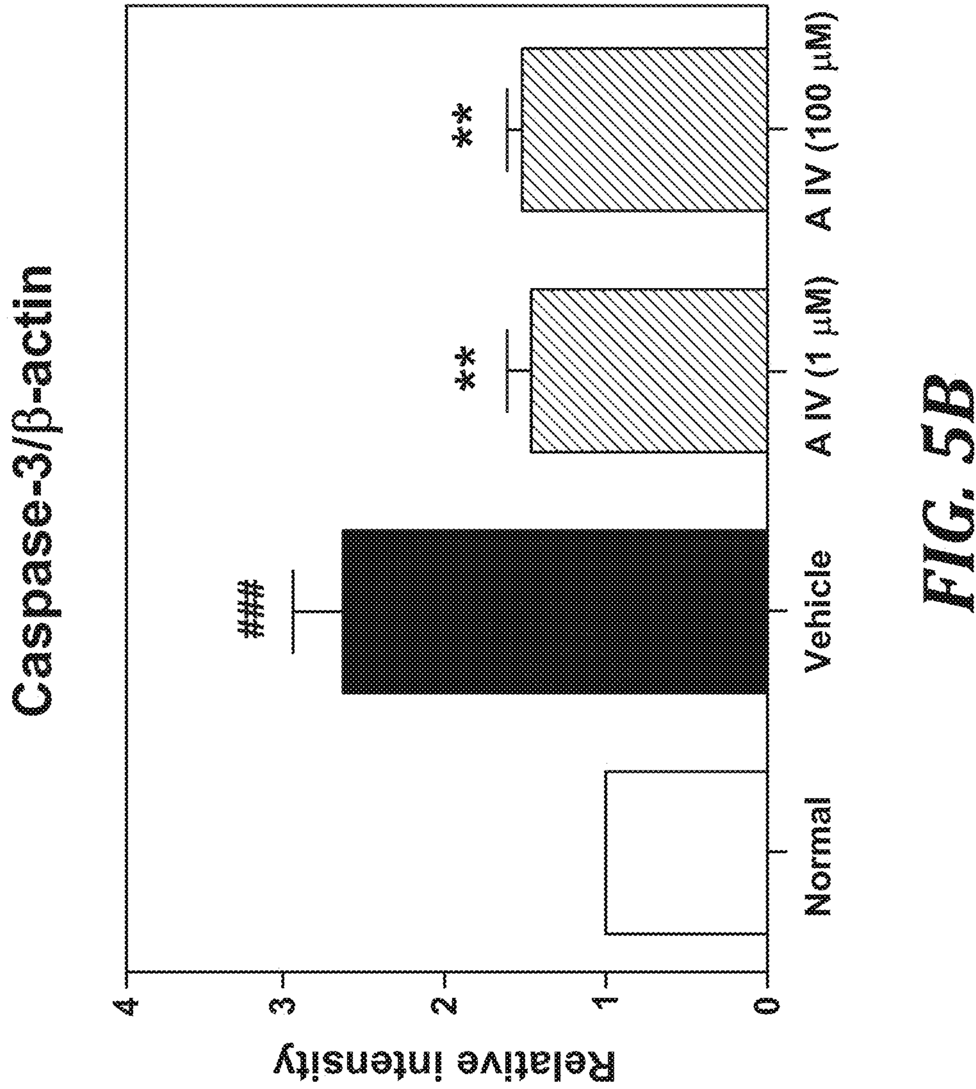
FIG. 5B is a bar graph showing the effects on Caspase 3 and Beta-Actin.
Figure 6A:
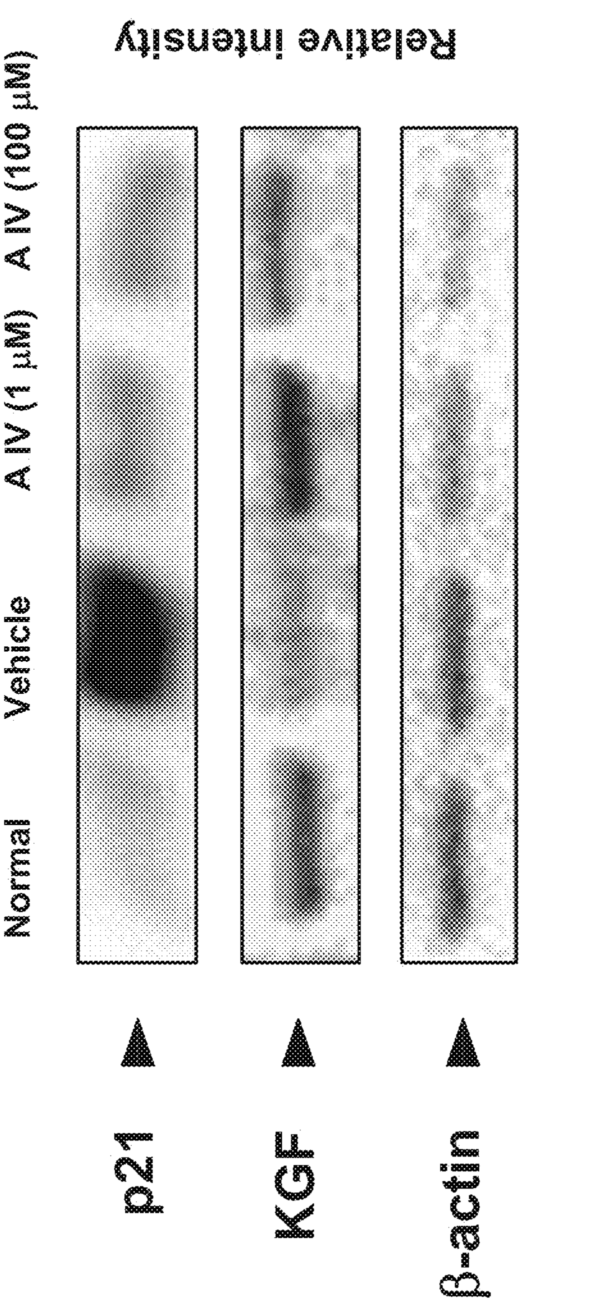
FIG. 6A is an electrophoretic gel showing activity on p21m KGF and Beta-Actin.
Figure 6B:
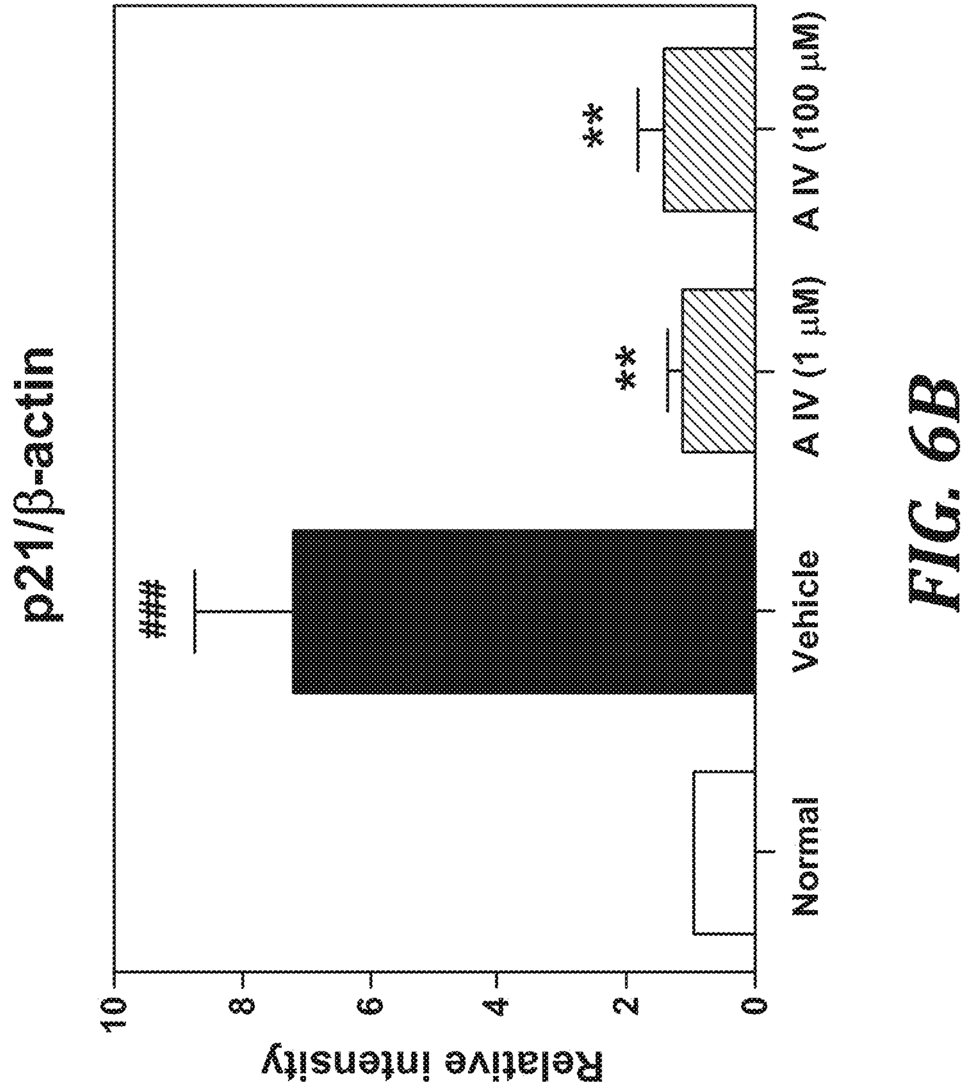
FIG. 6B is a bar graph showing activity in P21 and Beta-Actin.
Figure 6C:
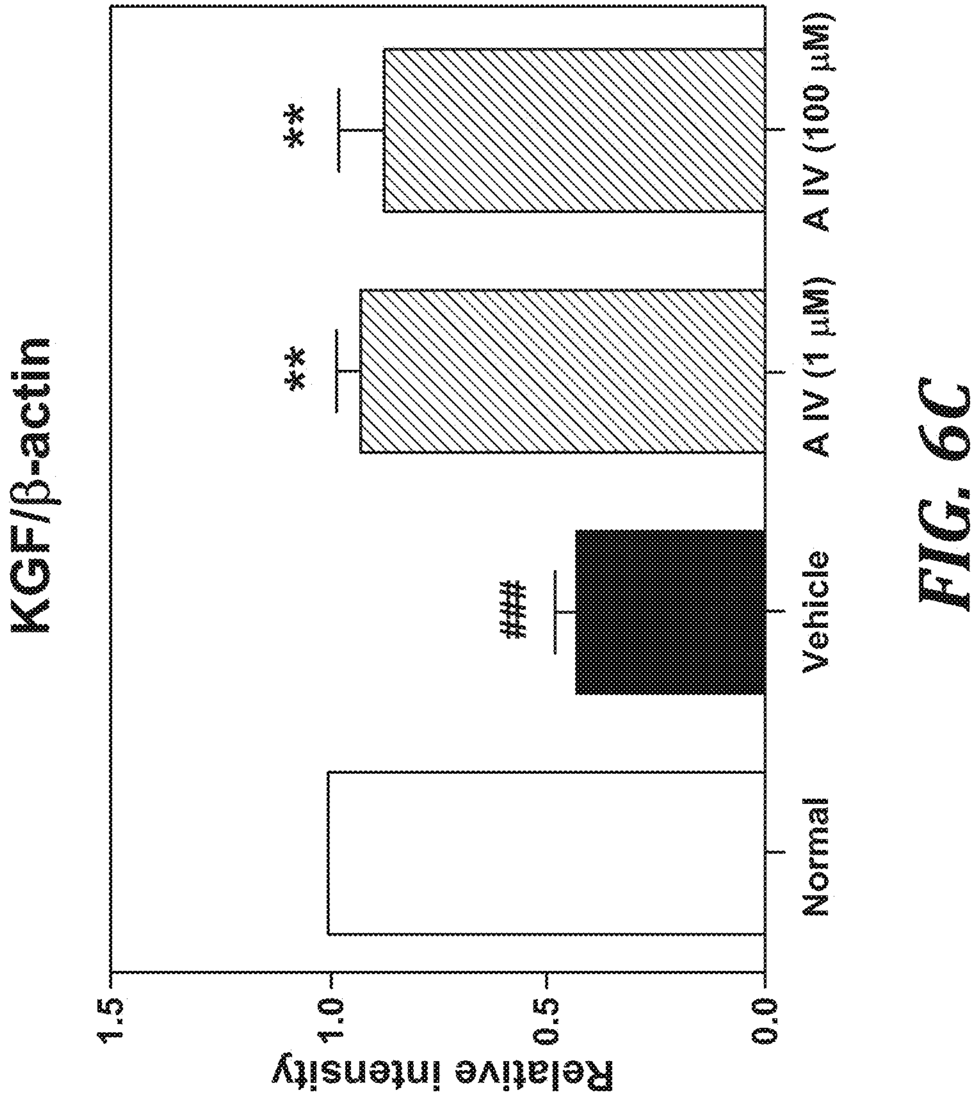
FIG. 6C is a bar graph showing activity of the activity in KGF and Beta-Actin.
Figure 7A:
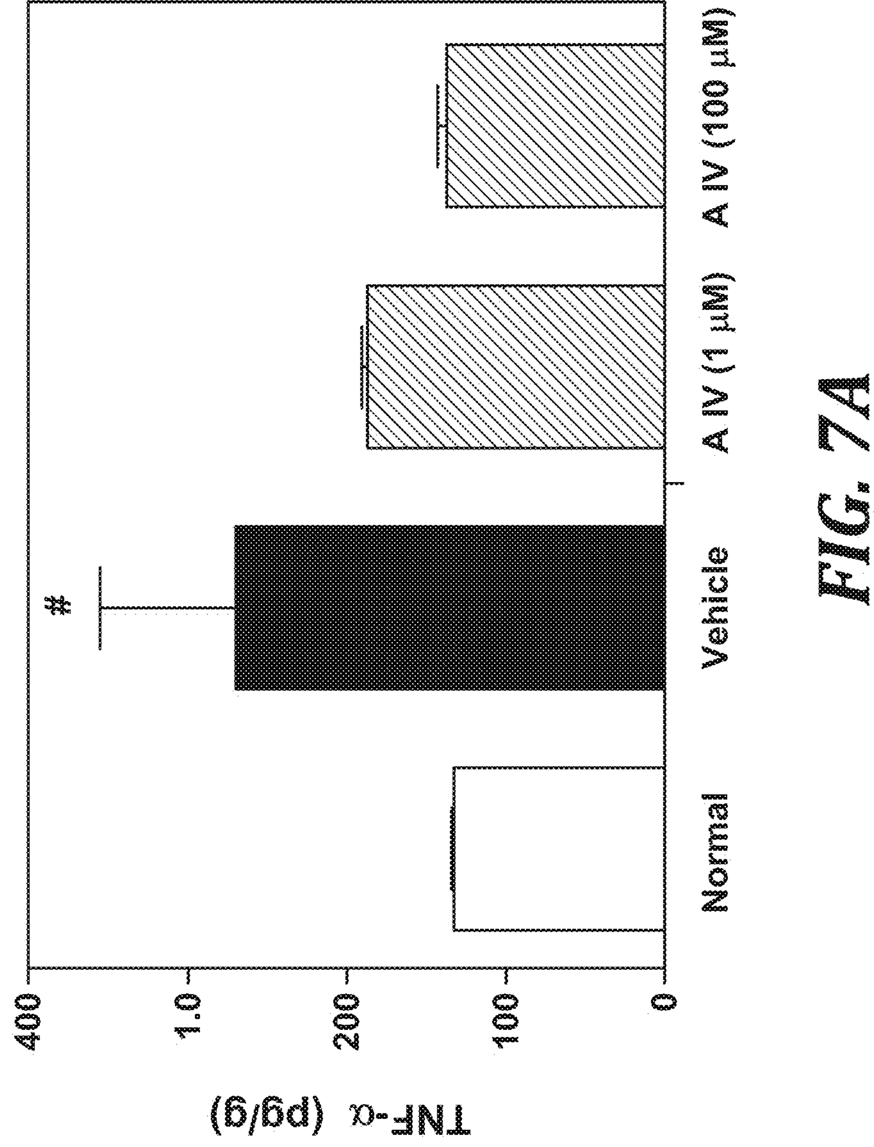
FIG. 7A is a bar graph showing activity on TNF-Alpha.
Figure 7B:
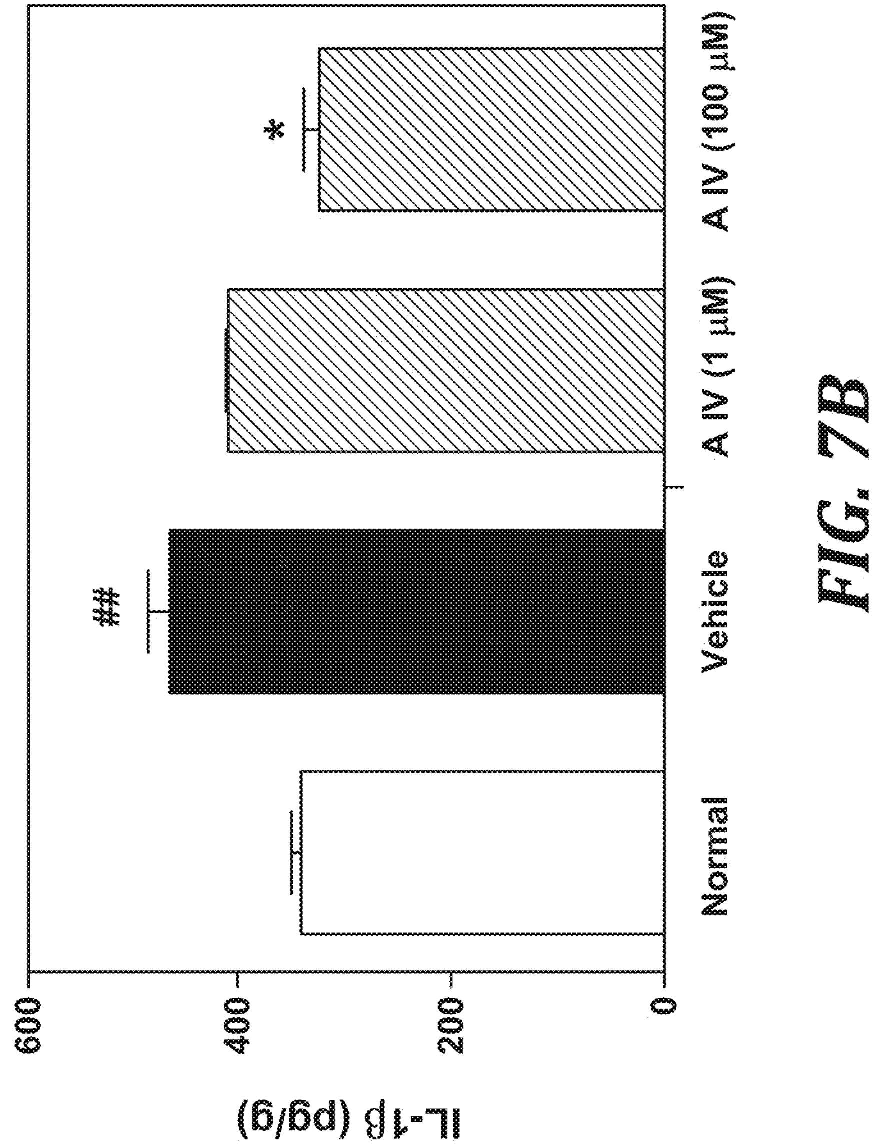
FIG. 7B is a bar graph showing activity of IL-1beta.
Figure 8:
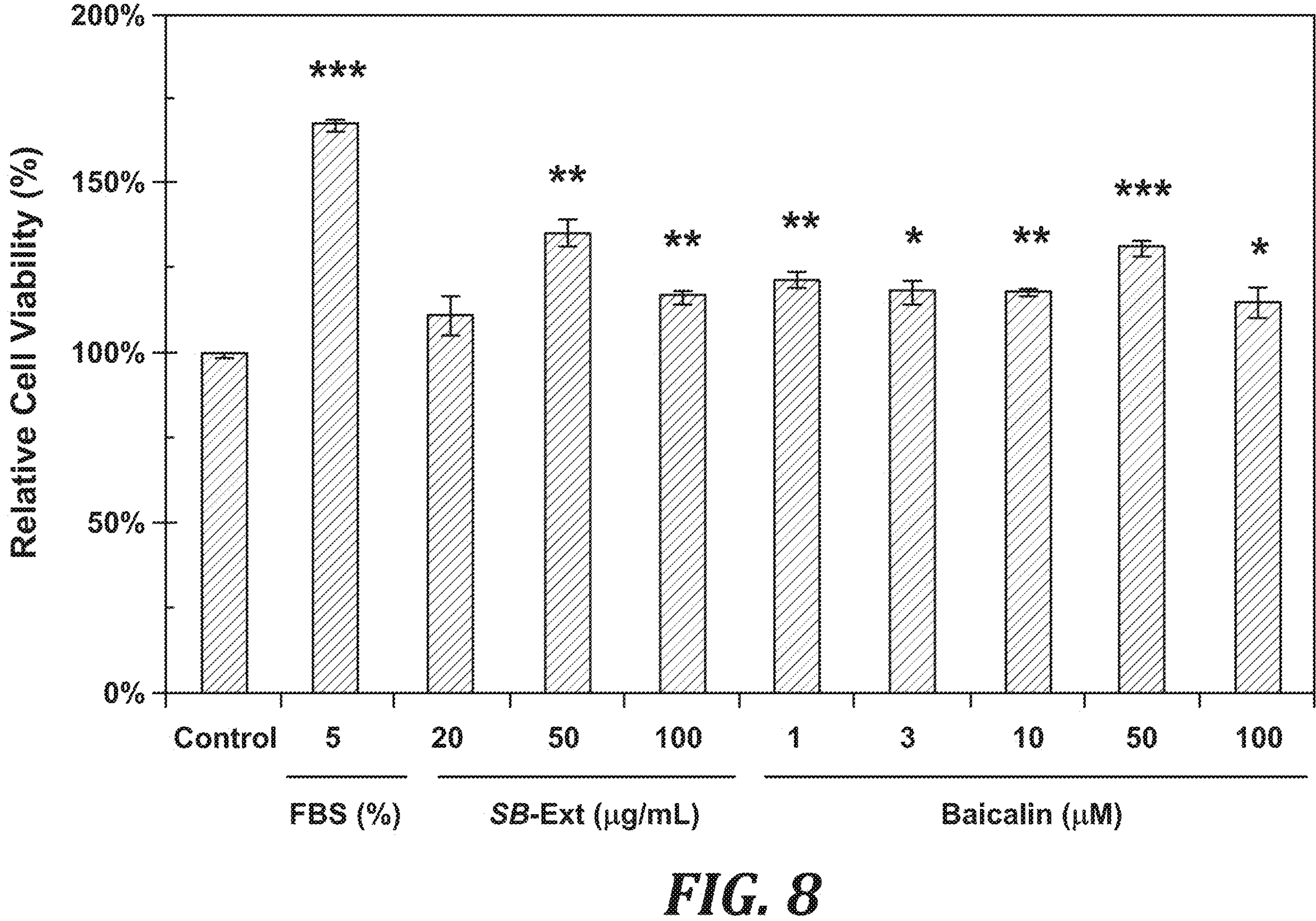
FIG. 8 is a graph showing cell viability.

Referring to FIGS. 5A and 5B, the research demonstrated that Astragaloside IV blocked the procaspase-8, resulting in the inhibition of the pro-apoptosis enzymes caspase-3 and procaspase-9 activities. The changes were accompanied with the down-regulation of Bax and p53 (pro-apoptotic molecules), and up-regulation of the anti-apoptotic Bcl-2 and Bcl-$_{XL}$ molecules. Further, the expressions of KGF (keratinocyte growth factor), p21, TNF-a and IL-1b, which are keratinocyte terminal differentiation markers associated with catagen, were modulated by treatment with Astragaloside IV.[146]

Procyanidins are a species of polyphenol which have been shown to possess a variety of physiological activities in both in vitro and in vivo murine models. Previous studies have reported that procyanidin oligomers such as procyanidin B-2 possess growth-promoting activity in murine hair epithelial cells, and that they can stimulate anagen induction in the in vivo murine model.[168] Results of a 12 month, double-blind clinical trial involving a total of 43 human subjects aimed at treating male pattern baldness by external application of 0.7% apple procyanidin oligomers demonstrated a statistically significant increase in total number of hairs in a designated scalp area after treatment with procyanidins compared to controls (procyanidin, 3.3±13.0 (mean±SD)/0.50 $cm^2$; placebo, −3.6±8.1/0.50 $cm^2$; P<0.001, two-sample t-test) without any adverse side effects observed in any of the subjects.[169]

Figure 9:
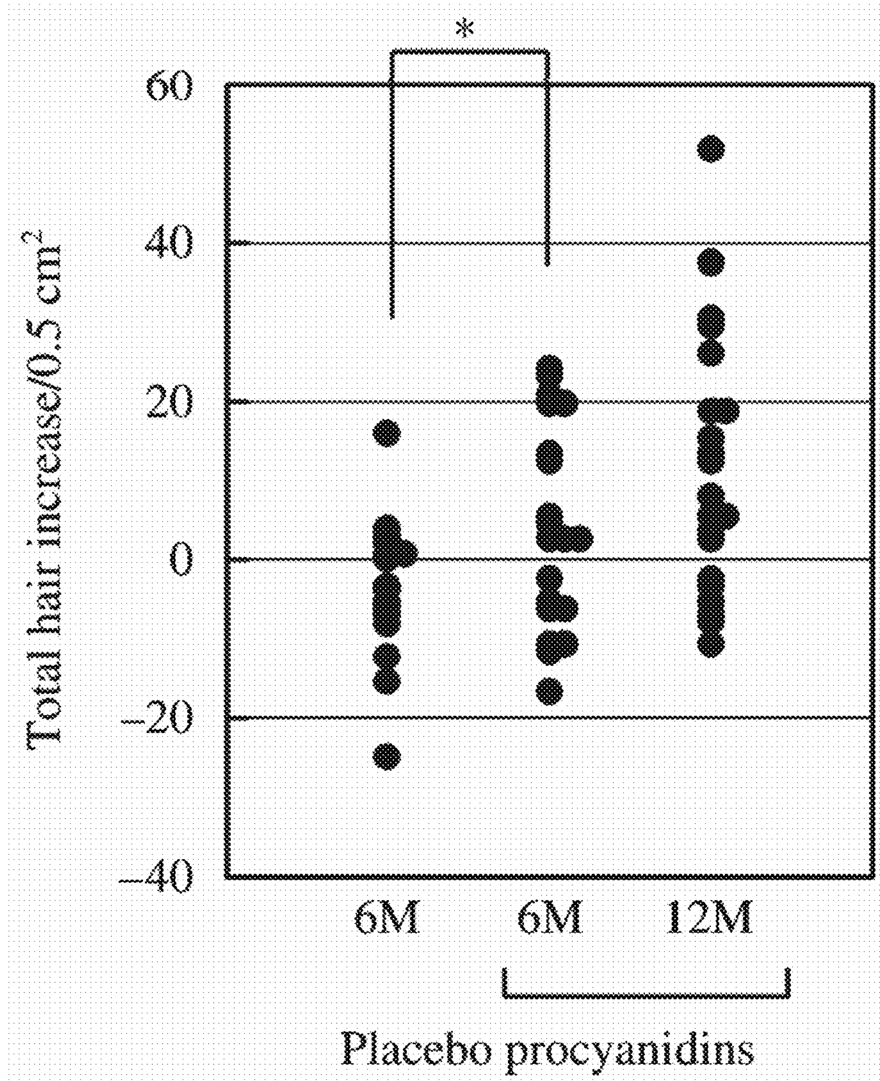
FIG. 9 is a graph showing change in hair density.

Referring to FIG. 9, the increased number of total hairs in the designated scalp area after the 6-month treatment of placebo control. 6-month treatment of procyanidin agent, (*P<0.001, two-sample t-test) and 12-month treatment of procyanidin. The total number of hairs in the designated scalp area after the 12-month procyanidin treatment significantly increased over the baseline value measured at the start of the trial (P<0.005, paired t-test).[169]

In a study to assess the effects of a *Scutellaria baicalensis* extract and its main component baicalin on proliferation of human scalp dermal papilla cells, researchers demonstrated that the extract and baicalin treatments dose-dependently inhibited the overgrowth of LNCaP prostate cancer cells, which are known to be stimulated by DHT.[170] Further, the extract and baicalin inhibited nuclear translocation of the androgen receptor stimulated by DHT in human dermal papilla cells, and the extract and baicalin enhanced proliferation of human dermal papilla cells in vitro.[170]

The results demonstrate that *Scutellaria baicalensis* extract and/or baicalin inhibited androgen activation signaling and promoted human dermal papilla cell proliferation, suggesting that either could be used as active ingredients for treating androgen-associated disorders, such as androgenetic alopecia.[146]

The above examples are representative of the discovery process and strategy utilized to develop a formulation that contains an exceptional mix of active ingredients that work together to provide a mammal with the fuel and nutrients it needs to support optimum hair health. More specifically, the formulations have been developed to provide the proper nutrition required as a foundation for healthy hair growth (scalp and follicular health) —amino acids, vitamins and trace minerals for proper protein production and tissue development and antioxidation necessary to scavenge the damage caused by free radical production. Further, the designed formulations necessarily modulate what the most recent researches in hair biology suggest are the important players in hair health. The following chart demonstrates cellular mediators targeted by the active ingredients within the formulations.

Composition Formulating Targets with Botanicals

Table 2 sets forth botanicals with their known targets. The present invention comprises the use of synergistic compositions of the botanicals in Table 2.

TABLE 2

| CATEGORY | TARGET | ACTIVE INGREDIENTS |
|---|---|---|
| GROWTH FACTOR | FGF-7 | *Eclipta alba*[171], *Polygonum multiflorum*[172], *Pisum sativum*[173] |
| MODULATION | FGF-18 | *Momordica charanita*[174] |
| | HGF | *Astragalus membranaceus*[172], *Momordica charanita*[176] |
| | IGF | *Sophora flavescens*[177] |
| | KGF | *Sophora flavescens*[177] |
| IMPROVED | VEGF | *Angelica sinensis*[178], |
| CIRCULATION | Blood flow | *Sophora flavescens*[179], Caffeine[180] |
| HAIR/STEM CELL | BMP | *Astragalus membranaceus*[181], *Pisum sativum*[182] |
| STIMULATION | mTORC1 | *Astragalus membranaceus*[183] |

TABLE 2-continued

| CATEGORY | TARGET | ACTIVE INGREDIENTS |
|---|---|---|
| | PKC | *Malus domestica*[184], *Vitis viniferis*[185] |
| | PPARγ | *Rosmarinus officinalis*[186] |
| | Shh | *Polygonum multiflorum*[187] |
| | Wnts/β-catenin | *Eclipta prostrat*, *Polygonum multiflorum*[188], *Scutellaria baicalensis*[189], *Sophora flavescens*[190], *Vitis viniferis*[185] |
| *IMMUNO-MODULATION | COX | *Punica granatum*[191], *Scutellaria baicalensis*[192], *Sophora flavescens*[193] |
| | INF-α, ING-γ | *Ganoderma lucidum*[194] |
| | Interleukins | *Ganoderma lucidum*[194], *Rosmarinus officinalis*[195], *Scutellaria baicalensis*[196] |
| | NF-κB | *Astragalus membranaceus*[197], *Ganoderma lucidum*[198], *Malus domestica*[199], *Rosmarinus officinalis*[200], *Scutellaria baicalensis*[201], *Sophora flavescens*[193] |
| | Prostaglandin | *Rosmarinus officinalis*[202], *Scutellaria baicalensis*[203] |
| | TNF-α | *Ganoderma lucidum*[194], *Rosmarinus officinalis*[202], *Scutellaria baicalensis*[203] |
| | TGF-β | *Astragalus membranaceus*[204], *Eclipta alba*[205], *Vitis viniferis*[206] |
| ANTI-ANDROGENETIC | DHT (or receptor) | *Rosmarinus officinalis*[207], *Scutellaria baicalensis*[42083] |
| | 5α-reductase | *Sophora flavescens*[177], Caffeine[209], *Ocimum basilicum*[210] |
| FOLLICLE PROTECTION | Antioxidant | *Astragalus membranaceus*[211], *Eclipta alba*[212], *Ganoderma lucidum*[213], *Malus domestica*[214], *Rosmarinus officinalis*[215], *Scutellaria baicalensis*[216], *Sophora flavescens*[217], *Vitis viniferis*[218], *Moringa olefiera*[219], *Punica granatum*[220] |
| | Anti-apoptosis | *Angelica sinensis*[221], *Astragalus membranaceus*[222], *Scutellaria baicalensis*[223], *Vitis viniferis*[224] |
| NUTRITION | | *Chenopodium quinoa*[225], *Ganoderma lucidum*[226], *Malus domestica*[227], *Moringa olefiera*[228], Lupine protein[229] |

Therapeutic Use

The botanical compositions and combinations of the present disclosure find use in any number of methods. For example, in some embodiments the botanical compositions are useful in methods for treating hair loss.

The present disclosure includes proliferators or reducers and activators or attenuators/inhibitors of stem cells and of one or more proteins in the Wnt pathway, including activators of one or more Wnt proteins, and compositions comprising the same. More particularly, it concerns the use of individual or combinations of botanical extracts or whole plant from grapeseed, skullcap, eclipta, Biotin or any combination thereof with or without Biotin or any analog thereof either by topical, oral, injectable, intravenous, buccal, suppository, inhalable administration in humans, mammals and vertebrates or in vitro administration in tissue or cells and thus treat or prevent diseases related to signal transduction.

The ingestible administered formulation composition may include any of fillers, such as rice bran, micro crystalline cellulose, production flow agents, such as silicon dioxide, binding agents, such as gums, resins, encapsulations, coatings, delayed release coatings, acid resistant coatings, fragrances, flavors, preservatives, slow release agents, rapid release agents, lipid or liposomal coatings, absorption enhancers, coloring agenms, solvents, water, oils, pH adjusters, anti-oxidation agents, anti-bacterial agents, oxygen, desiccants as a skilled artisan may employ to prepare the formula for oral, suppository, inhaling, buccal, nasal, or ocular delivery.

The topical formulation composition may include any of emulsifiers, surfactants, fragrances, permeators, preservatives, thickening agents, coloring agents, solvents, water, oils, conditioning agents, peroxides, pH adjusters, suspension agents, viscosity agents, anti-oxidation agents, anti-bacterial agents, masking agents, oxygen, pressure or temperature as a skilled artisan may employ to prepare the formula for topical delivery on the scalp and skin.

In one embodiment, the present invention provides a composition for preventing or decreasing the loss of hair and/or for stimulating or increasing hair growth or regrowth in a human or mammal, wherein the composition comprises a compound according to Formula X and/or XI.

In another embodiment, the present disclosure provides a composition for preventing depigmentation of hair color or repigmentation or remelanization of hair color and skin color, such as in greying of hair, canities and vitiligo in humans or mammal, wherein the composition comprises a compound according to Formula X and/or XI.

In another embodiment, the present disclosure provides a composition for Alopecia Areata, Scarring Alopecia such as; Central Centrifugal Cicatricial Alopecia, Cicatricial Alopecia Frontal Fibrosing Alopecia, Psuedopelade and Lichen Planopilaris; and Folliculitis, Seborrheic dermatitis, *Malassezia furfur*, Cradle Cap, Traction Alopecia, Loose Anagen Syndrome, Chronic Shedding, Medication induced hair loss, and growing of eyebrows, eyelashes and hair of the pubic region and the male beard.

In one embodiment, the present disclosure provides a composition for reducing scaling, flaking, redness, itch, irritation, allergy or sensitivity to the skin or scalp as is common with conditions such as psoriasis, eczema, dermatitis or rosacea in a human or mammal, wherein the composition comprises a compound according to Formula X and/or XI.

In one embodiment, the present disclosure provides a composition for preventing or decreasing inflammation, inflammatory responses on the skin and scalp and systemically by inhibition of TNF-alpha, prostaglandins, cox, and inflammatory response interleukins and cytokines and other inflammation markers including C-Reactive Protein and promotors such as insulin in a human or mammal, wherein the composition comprises a compound according to Formula X and/or XI.

In one embodiment, the present disclosure provides a composition for preventing oxidation and promoting antioxidant activity, wherein the composition comprises a compound according to Formula X and/or XI.

In one embodiment, the present disclosure provides a composition for improving kidney function as measured by glomerular filtration rate (GFR) in a human or mammal, wherein the composition comprises a compound according to Formula X and/or XI.

In one embodiment, the present disclosure provides a composition for improving thyroid function as measured by thyroid stimulating hormone in a human or mammal, wherein the composition comprises a compound according to Formula X and/or XI.

In one embodiment, the present disclosure provides a composition for improving cardiovascular risk factors, such as lipid markers and cardiovascular function as measured by HDL, Triglycerides, LDL and C-Reactive Protein in a human or mammal, wherein the composition comprises a compound according to Formula X and/or XI.

In one embodiment, the present disclosure provides a composition for reducing inflammation as measured by C-Reactive Protein in a human or mammal, wherein the composition comprises a compound according to Formula X and/or XI.

In one embodiment, the present disclosure provides a composition for retarding, reducing and/or reversing aging or the effects of aging in a human or mammal, wherein the composition comprises a compound according to Formula X and/or XI.

One embodiment of a tissue regenerator disclosed herein includes compounds of Formula X:

One embodiment of a tissue regenerator disclosed herein includes compounds of Formula XI:

Some embodiments include prodrugs of a compound of Formula X and/or XI. For example, prodrugs of a compound of Formula X and/or XI can be prodrug polymer conjugates for delayed release or extended release.

Also provided herein are pharmaceutical, botanical, vitamin, mineral, and enzyme compositions comprising a compound of Formula X and/or XI and a pharmaceutically acceptable carrier, diluent, or excipient.

Some embodiments of the present disclosure include methods to prepare or deliver compounds of Formula X and/or XI.

In various aspects, the composition or combination as disclosed herein can be administered at about 1.0 mcg/kg to about 100 mg/kg body weight (e.g., about 0.001 mg/kg to about 10 mg/kg or about 0.001 mg/kg to about 5 mg/kg or about 1 mg/kg to about 100 mg/kg).

In other aspects, the composition is administered by volume in a sufficient amount to cover the surface area of interest. A shampoo or conditioner for the hair and scalp may require 1-25 mL depending on the volume of hair present. A topical cream or ointment for the skin may only require 0.1 mL for a small area. One of average skill in the art or having common sense will know how to apply topical products of the present invention to saturate an area.

The concentrations of a disclosed compounds in a therapeutically acceptable formulation will vary depending on several factors, including the dosage of the compounds to be administered, the pharmacokinetic characteristics of the compound(s) employed, and the route of administration. The agent may be administered in a single dose or in repeat doses. The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. Treatments may be administered one, two, three, four or more times daily or more frequently depending upon a number of factors, including the overall health of a patient, and the formulation and route of administration of the selected compound(s). An ordinarily skilled physician, veterinarian or health practitioner can readily determine and prescribe the effective amount of the formulation required to prevent, counter or arrest the progress of the condition and regenerate the tissue.

The compounds or compositions of the present disclosure may be manufactured and/or administered in single or multiple unit dose forms.

Having now generally described the invention, the same will be more readily understood through reference to the following examples, which are provided by way of illustration and are not intended to be limiting of the present invention.

EXAMPLES

The disclosure now being generally described, it will be more readily understood by reference to the following examples which are included merely for purposes of illustration of certain aspects and embodiments of the present invention, and are not intended to limit the invention.

General Materials and Methods

The compositions of the present invention can be prepared and tested in a variety of ways known to one skilled in the art. The botanical extracts of the present invention can be prepared and tested using the methods as hereinafter described below, together with preparation methods known in the art of botanical extraction or variations thereon as appreciated by those skilled in the art.

Example 1: Dermal Papilla Media Preparation Protocol

Passage 3 human dermal papilla stem cells (HDPSCs) from a 55-year old male were purchased from Sigma-Aldrich (Burlington, ON, Canada) and all work was performed under Brock University Research Ethics Board approval (File 15-138). The cells were grown on collagen-coated plates in a 50:50 mixture of Dulbecco's modified Eagles medium (DMEM):Ham's F12 media (Sigma) supplemented with 10% fetal bovine serum (FBS), 1% Gluta-Max™, 0.1% penicillin/streptomycin, 20 ng/mL human fibroblast growth factor, and 10 ng/mL human epidermal growth factor (complete medium). Cell cultures were maintained in incubators set to 5% $CO_2$, 37° C. and 100% humidity. Experiments were performed under conditions of unregulated $O_2$ (18-19%), except where indicated. Cells initially underwent 5-7 passages and were then stored frozen in vials of one million cells each in the above medium supplemented with 10% dimethylsulfoxide (DMSO) and stored in liquid nitrogen. For each experiment, a single vial was thawed, grown overnight, and used to seed 96-well plates.

To a 500 mL bottle of high glucose DMEM bottle add the agents of Table 3:

TABLE 3

| Ingredient |
|---|
| 1.77 g of Ham's F-12 mixture |
| 0.196 g $NaHCO_3$ |
| (Add the above two first to DMEM, then filter using a 0.2 μm filter into an autoclaved bottle) |
| 10% FBS → 50 mL |
| 1% Gluta-Max ™ → 5 mL |
| 0.1% P/S → 0.5 mL |

Example 2: Basic FGF Preparation (20 ng/mL)

F0291 SIGMA (25 μg)

Reconstitute entire bottle with 1 mL of sterile filtered mM Tris (pH 7.0)

i. Can be stored for maximum 2 weeks at 4° C., or in aliquots at −20° C. for 6 months Therefore, 25 μg/mL aliquots (25,000 ng/mL) to be used at 20 ng/mL Therefore, add 8 μL of 25 μg/mL per 10 mL to reach desired 20 ng/mL Example 3: Epidermal GF Preparation (10 ng/mL)

E9644 SIGMA—2 mg

Reconstitute entire bottle with 2 mL sterile filtered 10 mM acetic acid (=1 mg/mL) (Note—if diluting this to lower concentration (>10 μg/mL), do so including 0.1% BSA Can be stored for maximum 1 month at 4° C. Otherwise, freeze aliquots at −20° C.

Therefore, going to have to dilute initial stock (1 mg/mL—initial stock) (x)=(10 μg/mL—new stock) (1250 μL) x=12.5 μL Therefore, add 12.5 μL of initial 1 mg/mL stock into 1237.5 μL 10 mM acetic acid containing 0.1% BSA (0.1% BSA here=1.25 mg BSA)

Therefore, add 10 μL of 10 μg/mL stock per 10 mL plate to reach 10 ng/mL.

Example 4: TopFlash/FopFlash Protocol

D-MEM F-12 Ham

1 L of D-MEM F-12 Ham medium (Gibco 12500-039) was made up by adding a full pouch of powder to 1 L Mili-Q® water.

The solution was filtered using a 0.2 μm bottle-top filter into a sterile bottle, after all D-MEM powder was dissolved into solution.

1.219 g $NaHCO_3$(EMD SX0320-1), 50 mL FBS (10%) and 5 mL Gluta-Max™ (Gibco 35050-061; 5%) were added to the D-MEM medium.

Basic FGF Preparation (20 ng/mL)

Sigma Aldrich F0291 25 μg was reconstituted entirely with 1 mL of sterile filtered 5 mM Tris (pH 7.0).

Aliquots of 10 μL were frozen at −20 for later use.

Epidermal GF Preparation (10 ng/nL)

Sigma Aldrich E9644 2 mg was reconstituted entirely with 2 mL of sterile filtered 10 mM acetic acid.

Aliquots of 12 μL were frozen at −20 for later use.

Cell Growth Assay

A vial of DP cells was thawed and grown in 10 mL of prepared D-MEM medium containing 8 μL (25 μg/mL) FGF and 10 μL (10 μg/mL) Epidermal GF on a collagen (Sigma Aldrich C4243) coated plate and grown in 5% oxygen until 80% confluent.

The cells were then seeded onto a collagen coated 96-well plate (white opaque with clear bottom, Greiner Bio-one 655098) using 2500 cells per well on average with 200 μL supplemented D-MEM. A total of 80 wells were seeded.

The cells were grown in 5% oxygen until 80% confluent and then transferred.

Transfection

In a 1.5 or 2 mL centrifuge tube, 5000 ng of Topflash plasmid DNA (95.5 ng/μL) and 500 μL DMEM (with no supplements or antibiotics) medium were mixed gently.

In a 1.5 or 2 mL centrifuge tube, 60 μL FuGene® 6 was added to 500 μL DMEM (with no supplements or antibiotics) medium and mixed gently, then incubated for 5 min.

1) and 2) were combined and mixed gently, then incubated for 20 min at room temperature with occasional gentle mixing by hand.

Old medium was removed from all wells and replaced with 100 μL fresh supplemented D-MEM.

μL of the DNA/FuGENE® 6 mixture was then added to each well and mixed gently by pipette.

Medium was changed after 4-6 h with 100 μL fresh supplemented DMEM.

Example 5: Preparation of Botanical Extracts

Grapeseed extract (*Vitis vinifera*) fine powder, extracted in water based extraction process, with an approximate extract ratio of 10-15:1, standardized to >=95% polyphenols as proanthocyanadins, as >=85% oligomeric proanthocyanadins and 5-15% monomers.

Skullcap (*Scutellaria baicalensis*; syn. huang qin), root, spray dried, fine powder, extracted in lower-temperature water based extraction process, with an approximate extract ratio of 12:1, standardized to 30% flavones as baicalin by UV with plant constituents including flavones (baicalin, baicalein, wogonin) and sterols.

*Eclipta* (*Eclipta prostrata*; syn. *Eclipta alba*; syn. Han Lian Cao) whole plant, spray dried, fine powder, extracted in lower-temperature water based extraction process, with an approximate extract ratio of 10:1, standardized to 5% lactones as wedelolactone with plant constituents including tannins, saponins, nicotine and ecliptine, Grapeseed, skullcap and eclipta or their respective extracts are used herein interchangeably and have the same meaning as the extracted or standardized materials. Extracts were prepared by solubilization in phosphate buffered saline (PBS). Where required, PBS was warmed and vortexed repeatedly to promote solubilization. Solubilized extracts were then filter sterilized using 0.2 micron syringe filters and stored in small aliquots as stock solutions.

Fresh aliquots of biotin, grapeseed, skullcap and eclipta extracts were made up according to Table 4:

TABLE 4

| | Concentration (mg/mL) |
|---|---|
| Biotin | 0.25 |
| Grapeseed | 7.5 |
| Skullcap | 1.7 |
| Eclipta | 0.3 |

Each extract was mixed with 1 mL medium and sterile filtered (0.45 μm).

They were then aliquoted in 50 μL amounts to freeze at −20 for later use.

10 μL of each stock was mixed with 990 μL of medium to yield a 1000-fold dilution.

To make mixtures of biotin with grapeseed, skullcap and eclipta, 2) was done in a 15 mL falcon tube with biotin and then mixed with 1 mL 1000-fold dilution of the three paired extracts, yielding three separate 15 mL falcon tubes with 1000-fold dilution.

100 μL of the 1000-fold dilution mixes of biotin+grapeseed and biotin+skullcap was added to 900 μL medium to make 10,000-fold dilutions.

10 μL of 1000-fold biotin and biotin+eclipta, and 10,000-fold biotin+grapeseed and biotin+skullcap dilutions were added to 100 μL of supplemented D-MEM medium in the appropriate wells. There were 8 wells for each of the 4 treatment combinations and 8 wells for untreated control cells, done in duplicate, for a total of 80 wells.

The treatments were performed three times once a day for a total of three days of treatment.

Example 6: Ludferase Assay

For all assays, general procedure was nearly identical:

Medium was removed from each well and wells were washed with 50 μL room temperature PBS so that no colour could be seen leftover.

20 μL lysis solution was added to each well and hand shaken every few minutes for a total of 15 mins.

The fluorescence spectrophotometer (Varian Cary Eclipse model) was set to:

Data mode: Bio/Chemi-luminescence

Emission wavelength: 560.00 nm

Stop time: 0.8 mins

PMT Detector Voltage: Medium

Emission slit: 20 nm a. 100 μL luciferase reagent was added for wells one at a time and ran for 1 min using the Twinlite™ assay kit (Perkin-Elmer) for TopFlash assays.

b. 100 μL of reagent was added to every well simultaneously and measured in sequence in the spectrophotometer using the Luciferase Reporter Gene Assay—High Sensitivity (Roche) for FopFlash assays.

For both TopFlash and FopFlash assays, 8 wells from each type of extract (biotin, biotin+grapeseed, biotin+skullcap, and biotin+eclipta), and 8 wells of control cells, were used in the luciferase assay.

3 of the duplicates of the wells from 3) were used to count the cells in each well and estimate a count for each type of extract.

Example 7: Measuring Effects of Botanical Extracts and Biotin on HDPSC Growth

Botanical extracts and Biotin were screened for their ability to stimulate HDPSC growth in culture using a 96-well plate format with MTT assay as an endpoint. Cells were treated for 72 h with various concentrations and combinations (as indicated, range; $1\times10^{-1}$-$1\times10^{-5}$) of extracts (Table 5a). All the ingredients were able to stimulate growth or cell proliferation above control to varying rates and by varied concentrations. However, the combination of eclipta extract with Biotin and skullcap extract with Biotin, strongly stimulated growth in this assay. Whereas grapeseed extract showed a tendency to promote growth with Biotin there was, however, no statistical significance.

Cell proliferation was assessed by MTT [3-(4,5-dimethylthiazol-2-yl)-2,5-diphenyltetrazolium bromide] assay according to the manufacturer's recommendations. HDPSCs were seeded onto collagen-coated 96-well plates at~2000 cells/well and grown in complete medium overnight. The next day, indicated concentrations of botanical extracts were added to individual wells.

For all constituents, lyophilized extracts (botanicals) or oil (Biotin) were initially dissolved in PBS at the following concentrations: Biotin 0.25 mg/mL; grapeseesd 7.5 mg/mL; skullcap 1.7 mg/mL; eclipta 3.0 mg/mL. These solutions were sterilized by passing through a 0.45 μm syringe filter. The following dilutions of these solutions, referred to as "Stock Solutions", were then used for experimental treatments in cell culture media: Biotin (1:100); grapeseed (1:1000); skullcap (1:1000); eclipta (1:100). DMEM media and extracts were refreshed each day. The following day, the MT assay was performed to evaluate cell growth. For this, all media/extract was removed from wells and replaced with phenol-red free DMEM. The cells were incubated for 2 h at 37° C. in a tissue culture incubator. Solubilization solution was then applied to lyse cells and the mixture was triturated repeatedly. The solubilized solutions from each well were then transferred to a fresh 96-well plate and absorbance read at 570 nm. Experiments were tested for 3 different concentration models and one was repeated three times at 5% oxygen and three times at 18% oxygen. Results confirmed proliferation of HDPSC's in all tested ingredients and combinations, although some concentrations and ratios did not proliferate HDPSC's and a few resulted in decreased HDPSC counts.

Botanical extracts of grapeseed, skullcap and eclipta and Biotin were screened for their ability to stimulate HDPSC growth in culture using a 96-well plate format with MT assay as an endpoint. Cells were treated for 72 h with various concentrations and combinations with further stock dilutions in the range; $10^{-1}$-$10^{-5}$ of the extracts. All the ingredients were able to stimulate growth or cell proliferation above control to varying rates and by varied concentrations, however for skullcap there was no statistical significance and for very low concentrations of Biotin, there was a statistically significant reduction in the cell population. The combinations of grapeseed extract with Biotin, skullcap extract with Biotin and eclipta extract with Biotin all stimulated statistically significant growth in this assay. (See Tables 5a, b, c, d, e, f, and g).

TABLE 5a

Effects of botanical extracts and Biotin on HDPSC proliferation in culture at 5% Oxygen with varying stock solution dilutions.

| Ingredient | Stock Dilutions and HDPSC Proliferation |
| --- | --- |
| Biotin | $10^{-3}$, 152% ***; |
| Grapeseed | $10^{-2}$, 118%; $10^{-3}$, 136% ***; |
| Skullcap | $10^{-2}$, 108%; $10^{-3}$, 107%; |
| Eclipta | $10^{-1}$, 122%; $10^{-2}$, 141% **; $10^{-3}$, 115% *; $10^{-5}$; 123%; |

HDPSC cells were treated 72 h with botanical extracts prepared as described in Materials and Methods and added to media at the indicated dilutions in 5% oxygen. Data are from the MTT assay and presented as means % relative to Control = 100% (n = 3-8). Signal is absorbance at 570 nm of reduced MTT.

* = $p < 0.05$,  = $p < 0.01$, * = $p < 0.001$ using Student T-Test for comparisons of treatment means with Control.

Table 5b shows the effects of botanical extracts with Biotin on HDPSC growth in culture at 5% Oxygen with varying stock solution dilutions using the following extract to Biotin ratios; Grapeseed:Biotin (7.5:1); Skullcap:Biotin (4:1); *Eclipta*:Biotin (1.2:1).

TABLE 5b

| Control | Biotin | | | Grapeseed (7.5) + Biotin (1) | | | Skullcap (4) + Biotin (1) | | | Eclipta (1.2) + Biotin (1) | | |
|---|---|---|---|---|---|---|---|---|---|---|---|---|
| | $1/10^3$ | $1/10^4$ | $1/10^5$ | $1/10^3$ | $1/10^4$ | $1/10^5$ | $1/10^3$ | $1/10^4$ | $1/10^5$ | $1/10^3$ | $1/10^4$ | $1/10^5$ |
| n = 6 | n = 6 | n = 6 | n = 6 | n = 6 | n = 6 | n = 6 | n = 6 | n = 6 | n = 6 | n = 6 | n = 6 | n = 6 |
| 1.00 ± | 1.12 ± | 0.95 ± | 0.69 ± | 0.69 ± | 0.82 ± | 1.08 ± | 1.10 ± | 1.25 ± | 1.05 ± | 0.94 ± | 0.90 ± | 0.80 ± |
| 0.04 | 0.10 | 0.08 | 0.09 | 0.04 | 0.20 | 0.07 | 0.04 | 0.10 | 0.08 | 0.08 | 0.05 | 0.04 |
| T-test to | 0.107 | 0.289 | 0.001 | 0.0001 | 0.007 | 0.158 | 0.079 | 0.008 | 0.263 | 0.275 | 0.456 | 0.01 |
| Control | ↑ | | ↓*** | ↓ | ↓ | ↑* | ↑ | ↑** | ↑ | ↓ | ↓ | ↓* |
| T-test to | | | | 0.001 | 0.077 | 0.003 | 0.438 | 0.023 | 0.006 | 0.099 | 0.298 | 0.137 |
| Biotin | | | | ↓* | ↓ | ↑** | ↓ | ↑* | ↑** | ↓ | ↓ | ↑ |

[]HDPSC cells were treated 72 h with botanical extracts prepared as described in Materials and Methods and added to media at the indicated dilutions in 5% oxygen. Data are from the MTT assay and presented as means ± SEM (n = 6). Signal is absorbance at 570 nm of reduced MTT.
*= $p < 0.05$, = $p < 0.01$, *= $p < 0.001$, using Student T-Test, for comparisons of treatment means with Control or Biotin alone at the same dilution.

Table 5c shows the effects of botanical extracts with Biotin on HDPSC growth in culture at 5% Oxygen with varying stock solution dilutions using the following extract to Biotin ratios; Grapeseed:Biotin (22.5:1); Skullcap:Biotin (4:1); *Eclipta*:Biotin (6:1).

TABLE 5c

| Control | Biotin | | | Grapeseed (22.5) + Biotin (1) | | | Skullcap (4) + Biotin (1) | | | Eclipta (6) + Biotin (1) | | |
|---|---|---|---|---|---|---|---|---|---|---|---|---|
| | $1/10^3$ | $1/10^4$ | $1/10^5$ | $1/10^3$ | $1/10^4$ | $1/10^5$ | $1/10^3$ | $1/10^4$ | $1/10^5$ | $1/10^3$ | $1/10^4$ | $1/10^5$ |
| n = 6 | n = 6 | n = 6 | n = 6 | n = 6 | n = 6 | n = 6 | n = 6 | n = 6 | n = 6 | n = 6 | n = 6 | n = 6 |
| 1.00 ± | 0.76 ± | 0.70 ± | 0.95 ± | 0.79 ± | 0.76 ± | 0.86 ± | 1.03 ± | 0.96 ± | 0.92 ± | 0.72 ± | 0.104 ± | 0.101 ± |
| 0.05 | 0.08 | 0.11 | 0.06 | 0.05 | 0.10 | 0.15 | 0.02 | 0.08 | 0.09 | 0.06 | 0.05 | 0.11 |
| T-test to | 0.10 | 0.08 | 0.272 | 0.013 | 0.016 | 0.147 | 0.367 | 0.355 | 0.221 | 0.005 | 0.313 | 0.468 |
| Control | ↓ | ↓ | ↓ | ↓* | ↓* | ↓ | ↑ | ↓ | ↓ | ↓ | ↑ | ↑ |
| T-test to | | | | 0.370 | 0.353 | 0.309 | 0.004 | 0.048 | 0.418 | 0.370 | 0.011 | 0.311 |
| Biotin | | | | ↑ | ↑ | ↓ | ↑** | ↑* | ↓ | ↓ | ↑* | ↑ |

HDPSC cells were treated 72 h with botanical extracts prepared as described in Materials and Methods and added to media at the indicated dilutions in 5% oxygen. Data are from the MTT assay and presented as means ± SEM (n = 6). Signal is absorbance at 570 nm of reduced MTT.
*= $p < 0.05$, = $p < 0.01$, *= $p < 0.001$, using Student T-Test, for comparisons of treatment means with Control or Biotin alone at the same dilution.

Table 5d shows the effects of botanical extracts with Biotin on HDPSC growth in culture at 5% Oxygen with varying stock solution dilutions using the following extract to Biotin ratios; Grapeseed:Biotin (30:1); Skullcap:Biotin (6.8:1); *Eclipta*:Biotin (12:1).

TABLE 5d

| Control | Biotin | | | Grapeseed (30) + Biotin (1) | | | Skullcap (6.8) + Biotin (1) | | | Eclipta (12) + Biotin (1) | | |
|---|---|---|---|---|---|---|---|---|---|---|---|---|
| Dilution of stock | $1/10^3$ | $1/10^4$ | $1/10^5$ | $1/10^3$ | $1/10^4$ | $1/10^5$ | $1/10^3$ | $1/10^4$ | $1/10^5$ | $1/10^3$ | $1/10^4$ | $1/10^5$ |
| n = 30 | n = 30 | n = 30 | n = 30 | n = 30 | n = 30 | n = 30 | n = 30 | n = 30 | n = 30 | n = 30 | n = 30 | n = 30 |
| 1.00 ± | 1.52 ± | 1.09 ± | 0.79 ± | 1.12 ± | 1.22 ± | 0.82 ± | 1.14 ± | 1.25 ± | 1.30 ± | 1.10 ± | 0.99 ± | 1.33 ± |
| 0.07 | 0.17 | 0.14 | 0.09 | 0.13 | 0.20 | 0.07 | 0.15 | 0.19 | 0.13 | 0.17 | 0.07 | 0.14 |
| T-test to | 0.001 | 0.261 | 0.046 | 0.198 | 0.109 | 0.062 | 0.185 | 0.073 | 0.019 | 0.275 | 0.456 | 0.013 |
| Control | ↑*** | ↑ | ↓* | ↑ | ↑ | ↓* | ↑ | ↑ | ↑* | ↑ | | ↑* |
| T-test to | | | | 0.037 | 0.300 | 0.394 | 0.05 | 0.251 | 0.002 | 0.048 | 0.252 | 0.001 |
| Biotin | | | | ↓* | ↑ | — | ↓* | ↑ | ↑** | ↓* | — | ↑*** |

HDPSC cells were treated 72 h with botanical extracts prepared as described in Materials and Methods and added to media at the indicated dilutions in 5% oxygen. Data are from the MTT assay and presented as means ± SEM (n = 29-30). Signal is absorbance at 570 nm of reduced MTT.
*= $p < 0.05$, = $p < 0.01$, *= $p < 0.001$, using Student T-Test, for comparisons of treatment means with Control or Biotin alone at the same dilution.

Table 5e shows the effects of botanical extracts with biotin on HDPSC growth in culture at 5% oxygen with varying stock solutions using the following extract to biotin ratios: Grapeseed:Biotin (30:1); Skullcap:Biotin (6.8:1); *Eclipta*: Biotin (12:1).

TABLE 5e

| | Control | Biotin | | Proanthocyanidins (30) + Biotin (1) | | Skullcap (6.8) + Biotin (1) | | Eclipta (12) + Biotin (1) | |
|---|---|---|---|---|---|---|---|---|---|
| Dilution of stock | n/a | $1/10^3$ | $1/10^5$ | $1/10^3$ | $1/10^5$ | $1/10^3$ | $1/10^5$ | $1/10^3$ | $1/10^5$ |
| N | n = 30 | n = 30 | n = 30 | n = 29 | n = 30 | n = 30 | n = 30 | n = 29 | n = 30 |
| Change in Stem | 1.00 ± | 1.52 ± | 0.79 ± | 1.12 ± | 0.82 ± | 1.14 ± | 1.30 ± | 1.10 ± | 1.33 ± |
| Cells SEM | 0.07 | 0.17 | 0.09 | 0.13 | 0.07 | 0.15 | 0.13 | 0.17 | 0.14 |
| Change vs Control | | 52.0% | −21.0% | | −18.0% | 14.0% | 30.0% | | 33.0% |
| T-test to Control | | 0.001 | 0.046 | | 0.062 | 0.185 | 0.019 | | 0.013 |
| | | ↑*** | ↓* | | ↓* | ↑ | ↑* | | ↑* |
| Change vs Biotin | | | | −26.3% | | −25.0% | 64.6% | −27.6% | 68.4% |
| T-test to Biotin | | | | 0.037 | | 0.05 | 0.002 | 0.048 | 0.001 |
| | | | | ↓* | | ↓* | ↑** | ↓* | ↑*** |

Table 5f shows the effects of botanical extracts with Biotin on HDPSC growth in culture at 18% Oxygen with varying stock solution dilutions using the following extract to Biotin ratios; Grapeseed:Biotin (30:1); Skullcap:Biotin (6.8:1); *Eclipta*: Biotin (12:1)

TABLE 5f

| Control | Biotin | | | Grapeseed (30) + Biotin (1) | | | Skullcap (6.8) + Biotin (1) | | | Eclipta (12) + Biotin (1) | | |
|---|---|---|---|---|---|---|---|---|---|---|---|---|
| Dilution of stock | $1/10^3$ | $1/10^4$ | $1/10^5$ | $1/10^3$ | $1/10^4$ | $1/10^5$ | $1/10^3$ | $1/10^4$ | $1/10^5$ | $1/10^3$ | $1/10^4$ | $1/10^5$ |
| n = 30 | n = 30 | n = 29 | n = 30 | n = 30 | n = 30 | n = 30 | n = 30 | n = 30 | n = 30 | n = 30 | n = 30 | n = 30 |
| 1.00 ± | 0.99 ± | 1.21 ± | 0.98 ± | 1.07 ± | 1.13 ± | 1.06 ± | 1.32 ± | 1.41 ± | 1.19 ± | 1.75 ± | 1.57 ± | 1.24 ± |
| 0.10 | 0.10 | 0.12 | 0.07 | 0.09 | 0.10 | 0.09 | 0.10 | 0.11 | 0.15 | 0.28 | 0.17 | 0.12 |
| T-test to | 0.479 | 0.096 | 0.444 | 0.299 | 0.191 | 0.348 | 0.017 | 0.004 | 0.133 | 0.001 | 0.001 | 0.058 |
| Control | ↓ | ↑ | ↓ | ↑ | ↑ | ↑ | ↑* | ↑* | ↑ | ↑*** | ↑*** | ↑ |
| T-test to | | | | 0.276 | 0.312 | 0.260 | 0.017 | 0.120 | 0.115 | 0.008 | 0.048 | 0.034 |
| Biotin | | | | ↑ | ↓ | ↑ | ↑* | ↑ | ↑ | ↑** | ↑* | ↑* |

HDPSC cells were treated 72 h with botanical extracts prepared as described in Materials and Methods and added to media at the indicated dilutions in 18% oxygen. Data are from the MTT assay and presented as means ± SEM (n = 29-30). Signal is absorbance at 570 nm of reduced MTT.
*= $p < 0.05$, = $p < 0.01$, *= $p < 0.001$, using Student T-Test, for comparisons of treatment means with Control or Biotin alone at the same dilution.

Table 5g shows the effects of botanical extracts with Biotin on HDPSC growth in culture at 18% Oxygen with varying stock solution dilutions using the following extract to Biotin ratios; Grapeseed:Biotin (30:1); Skullcap:Biotin (6.8:1); *Eclipta*: Biotin (12:1).

TABLE 5g

| | Control | Skullcap (6.8) + Biotin (1) | | Eclipta (12) + Biotin (1) | | |
|---|---|---|---|---|---|---|
| Dilution of stock | n/a | $1/10^3$ | $1/10^4$ | $1/10^3$ | $1/10^4$ | $1/10^5$ |
| N | n = 30 | n = 30 | n = 30 | n = 30 | n = 30 | n = 30 |
| Change in Stem Cells SEM | 1.00 ± 0.10 | 1.32 ± 0.10 | 1.41 ± 0.11 | 1.75 ± 0.28 | 1.57 ± 0.17 | 1.24 ± 0.12 |
| Change vs Control | | 32.0% | 41.0% | 75.0% | 57.0% | |
| T-test to Control | | 0.017 | 0.004 | 0.001 | 0.001 | |
| | | ↑* | ↑* | ↑*** | ↑*** | |
| Change vs Biotin | | 33.3% | | 76.8% | 29.8% | 26.5% |
| T-test to Biotin | | 0.017 | | 0.008 | 0.048 | 0.034 |
| | | ↑* | | ↑** | ↑* | ↑* |

HDPSC cells were treated 72 h with botanical extracts prepared as described in Materials and Methods and added to media at the indicated dilutions in 18% oxygen. Data are from the MTT assay and presented as means ± SEM (n = 29-30). Signal is absorbance at 570 nm of reduced MTT.
*= $p < 0.05$, = $p < 0.01$, *= $p < 0.001$, using Student T-Test, for comparisons of treatment means with Control or Biotin alone at the same dilution.

Stock Solutions

Biotin 0.25 mg/mL stock (1:100 dilution);

Grapeseed 7.5 mg/mL stock (1:1000 dilution);

Skullcap 1.7 mg/mL stock (1:1000 dilution);

*Eclipta* 3.0 mg/mL stock (1:100 dilution).

HDPSC Proliferation

Table 6 shows botanical ingredients and biotin proliferate HDPSC populations in %.

TABLE 6

| Ingredient | Stock Dilutions and HDPSC Proliferation |
|---|---|
| Biotin | $10^{-3}$, 152% ***; |
| Grapeseed | $10^{-2}$, 118%; $10^{-3}$, 136% ***; |
| Skullcap | $10^{-2}$, 108%; $10^{-3}$, 107%; |
| Eclipta | $10^{-1}$, 122%; $10^{-2}$, 141% **; $10^{-3}$, 115% *; $10^{-5}$, 123%; |

HDPSC Reduction

Table 7 shows biotin diluted stock reduces HDPSC populations in % with statistical significance.

TABLE 7

| Ingredient | Stock Dilutions and HDPSC Proliferation |
|---|---|
| Biotin | $10^{-5}$, 79% *; (HDPSC population reduced by 21%) |

HDPSC Proliferation

Table 8 shows that combinations of botanical ingredients with biotin mixed in various ratios of diluted stock concentrations ($10^{-x}$) promote proliferation of HDPSC's in % with statistical significance.

TABLE 8

| Combinations | Ratio | Stock Dilutions HDPSC Proliferation |
|---|---|---|
| Grapeseed:Biotin | 7.5:1 | $10^{-5}$, 108% **; |
| Skullcap:Biotin | 4:1 | $10^{-4}$, 125% ** |
| | 6.8:1 | $10^{-3}$, 132% *; $10^{-4}$, 141% *; $10^{-5}$, 130% **; |
| Eclipta:Biotin | 12:1 | $10^{-3}$, 175% **; $10^{-4}$, 157% *; $10^{-5}$, 133% *; |

Example 8: Measuring Effects of Botanical Extracts on HDPSC Wnt/Beta-Catenin Protein Signaling Stimulation of stem cell growth and proliferation can be achieved by activation of the Wnt/beta-Catenin signaling pathway. Having confirmed proliferation of HDPSC's by exposure to grapeseed, skullcap, eclipta and Biotin and combinations thereof, a series of studies were conducted to detect and measure the upregulation of the Wnt/beta-Catenin protein as the activation mechanism of the HDPSC proliferation. The method selected for the Wnt/beta-Catenin protein studies was transfection with Topflash and Fopflash plasmids followed by measuring luciferase activity by bioluminescence assays.

Topflash and Fopflash plasmids were obtained as bacterial stab cultures from Add gene. Plasmid DNA was purified using the Norgen Biotek kit (info). For transfections, HDPSCs were seeded onto 96-well plates according to the most efficacious dilution identified by the MTT growth assay and grown until 80% confluent. Cells were transfected with Topflash or Fopflash using FuGENE™ 6. Old medium was removed and replaced with 100 μL fresh complete medium. 20 μL of DNA/FuGENE™ 6 mixture was added and mixed gently by pipette. After 4-6 h, medium was removed and replaced with 100 μL fresh complete medium. Botanical extracts were then added to each well. Treatments lasted 72 h with media/extracts refreshed every 24 h.

Activation of Wnt/beta-Catenin signaling was assayed as luciferase activity using standard bioluminescence assays. Media from each well was removed and cells were washed twice with 50 μL PBS. 20 μL of cell lysis solution was then added to each well and the plate was incubated at room temperature for 15 min. Luminescence at 560±10 nm was measured using a Varian Cary Eclipse fluorescence spectrophotometer. Immediately prior to each measurement, 100 μL of luciferase reagent was added to the well to be measured.

HDPSCs were transfected with Topflash plasmid, which contains the luciferase cDNA and several tandem repeats of the Wnt/β-catenin response element 1. Following transfection, cells were treated for three days as for the MTT assay and then assayed for luciferase activity using standard assays. Grapeseed, skullcap, and eclipta extracts increased the luciferase signal significantly in this assay, indicating Wnt/beta-Catenin-mediated stimulation of transcription.

To evaluate whether the extract combinations with Biotin identified in FIG. 1 activate Wnt/beta-Catenin signaling, HDPSCs were transfected with Topflash plasmid, which contains the luciferase cDNA and several tandem repeats of the Wnt/beta-Catenin response element.[230] Following transfection, cells were treated for three days as for the MTT assay and then assayed for luciferase activity using standard assays. Both eclipta and skullcap extracts increased the luciferase signal with statistical significance and grapeseed also increased the luciferase signal in this assay, indicating Wnt/beta-Catenin-mediated stimulation of transcription.

Wnt/beta-Catenin Signaling Results

Table 9a shows the summary effects of botanical extracts and biotin on luciferase activity in TopFlash transfected HDPSCs at 18% Oxygen using the following extract to Biotin ratios; Grapeseed:Biotin (30:1); Skullcap:Biotin (6.8:1); *Eclipta*:Biotin (12:1).

TABLE 9a

| Control | Biotin | Grapeseed | Skullcap | Eclipta |
|---|---|---|---|---|
| 17.5 ± 0.9 | 17.0 ± 0.9 | 23.0 ± 0.9*** | 33.8 ± 0.9*** | 47.8 ± 1.2*** |

HDPSC cells were treated 72 h with botanical extracts and biotin prepared as described in Materials and Methods and added to media at the indicated dilutions in 18% oxygen. Data are means ± standard error of the mean (SEM) of 27-28 replicate measurements. ***= highly significant difference from control, $p < 0.001$ determined by Student T-Test for comparison to Control. Units are arbitrary luminescence values measured at 560 ± 10 nm.

FIG. 1 shows the effects of individual extracts and Biotin on Wnt/β-Catenin Signaling in HDPSCs transfected with Topflash plasmid. In the figure '***'=highly significant difference from control, p<0.001 determined by Student T-Test compared to Control.

Table 9b shows the effects of single botanical extract treatments on luciferase activity (Wnt/beta-Catenin Signalling) in TopHlash transfected HDPSCs at 18% Oxygen.

TABLE 9b

| | Control | Biotin | Grapeseed | Skullcap | Eclipta |
|---|---|---|---|---|---|
| 1 | 19.889109 | 20.499516 | 25.026705 | 32.198992 | 41.075333 |
| 2 | 13.327229 | 14.242840 | 18.871763 | 28.333078 | 42.525055 |
| 3 | 13.378097 | 12.513352 | 16.837072 | 25.637112 | 37.489189 |
| 4 | 18.668293 | 15.717993 | 21.465994 | 31.842920 | 42.372452 |
| 5 | 23.704157 | 22.025536 | 26.857927 | 31.130779 | 39.778217 |
| 6 | 23.653290 | 23.297216 | 28.180477 | 38.048729 | 45.780560 |
| 7 | 21.008190 | 21.567730 | 25.789715 | 35.861437 | 47.281143 |
| 8 | 13.225495 | 17.498346 | 23.348085 | 34.945827 | 48.425655 |
| 9 | 11.953812 | 14.293708 | 19.227835 | 33.216339 | 48.629128 |
| 10 | 17.650949 | 19.583904 | 23.297216 | 34.996693 | 46.492699 |
| 11 | 22.330738 | 23.449820 | 27.519201 | 37.590923 | 49.137802 |
| 12 | 24.111094 | 26.247520 | 32.809399 | 42.118114 | 53.054581 |

TABLE 9b-continued

| | Control | Biotin | Grapeseed | Skullcap | Eclipta |
|---|---|---|---|---|---|
| 13 | 19.278702 | 19.583904 | 23.297216 | 45.805990 | 62.744799 |
| 14 | 24.212828 | 19.990845 | 30.367771 | 35.810570 | 49.493870 |
| 15 | 23.551554 | 20.753853 | 28.638283 | 40.744698 | 52.495041 |
| 16 | 15.056717 | 12.462485 | 20.041712 | 34.589756 | 52.800247 |
| 17 | 10.376926 | 7.884430 | 15.819727 | 32.046394 | 53.817589 |
| 18 | 13.988504 | 11.648608 | 21.567730 | 33.470676 | 54.733200 |
| 19 | 14.751513 | 12.513352 | 24.772367 | 29.655628 | 51.579430 |
| 20 | 20.092579 | 16.277531 | 27.468334 | 40.337761 | 58.599113 |
| 21 | 20.499516 | 20.143446 | N/A | 37.641792 | 54.758636 |
| 22 | 23.144615 | 20.753853 | 23.348085 | 33.775879 | 44.661476 |
| 23 | 21.465994 | 20.652119 | 27.061398 | 33.725014 | 44.864948 |
| 24 | 11.394273 | 10.275191 | 17.447479 | 28.943487 | 40.337761 |
| 25 | 8.545704 | 7.630093 | 12.309884 | 25.535379 | 37.336586 |
| 26 | 10.224324 | 10.936467 | 17.040541 | 28.638283 | 43.186325 |
| 27 | 12.462485 | 15.565390 | 19.227835 | 29.197823 | 45.271885 |
| 28 | 17.396612 | 18.617428 | 23.500687 | 31.385117 | 50.104279 |
| Mean | 17.476546 | 17.022374 | 23.005201 | 33.829471 | 47.815250 |
| SEM | 0.939119 | 0.936618 | 0.926875 | 0.919666 | 1.185888 |
| T-TEST (p-value) | | 0.73336161 | 0.000120236 | 1.74696E−17 | 6.17291E−26 |
| % Change vs Control | | 0% | 31.6% | 93.6% | 173.6% |

HDPSC cells were treated 72 h with botanical extracts and biotin prepared as described in Materials and Methods and added to media at the indicated dilutions in 18% oxygen. Data are means ± standard error of the mean (SEM) of 27-28 replicate measurements.
*** = highly significant difference from control, p < 0.001 determined by student t-test for comparison to Control. Units are arbitrary luminescence values measured at 560 ± 10 nm.

Table 9c shows the effects of Combination of Botanical extracts with biotin on luciferase activity in TopFlash transfected HDPSCs at 18% Oxygen using the following extract to Biotin ratios; Grapeseed:Biotin (30:1); Skullcap:Biotin (6.8:1); *Eclipta*:Biotin (12:1).

TABLE 9c

| Control | Biotin | Grapeseed + Biotin | Skullcap + Biotin | Eclipta + Biotin |
|---|---|---|---|---|
| 80.01 ± 8.3 | 79.2 ± 7.3 | 86.7 ± 6.7† | 101 ± 7.7* | 116.8 ± 7.0*** |

HDPSC cells were treated 72 h with grapeseed, eclipta and skullcap extracts in combination with Biotin in 18% oxygen increase luciferase signal (arbitrary units) above control. Eclipta and skullcap data represent means ± SEM of 18-20 replicate measurements.
*= significant difference, p < 0.05, and ***= highly significant difference, p < 0.001, students t-test.
† = positive result, not statistically significant compared to Control. Units are arbitrary luminescence values measured at 560 ± 10 nm.

Table 9d Table 9d shows the effects of combination Botanical treatment with Biotin on luciferase activity in TopFlash transfected HDPSCs.

TABLE 9d

| | Control | Biotin | Grapeseed + Biotin | Skullcap + Biotin | Eclipta + Biotin |
|---|---|---|---|---|---|
| 1 | 94.0743 | 95.4836 | 98.9276 | 109.5094 | 126.6342 |
| 2 | 74.2798 | 110.3368 | 108.8306 | 120.3577 | 140.0427 |
| 3 | 84.9048 | 109.6925 | 134.1370 | 115.3670 | 141.30933 |
| 4 | 93.73824 | 129.5662 | 139.5798 | 128.44717 | 175.73195 |
| 5 | 118.0412 | 112.3295 | 119.4300 | 167.8112 | 149.8042 |
| 6 | 106.1092 | 79.5782 | 103.7523 | 124.4277 | 135.5032 |
| 7 | 122.8021 | 105.8972 | 96.6478 | 111.1874 | 139.6900 |
| 8 | 117.8680 | 78.0728 | 84.3041 | 120.1655 | 140.1139 |
| 9 | 114.7820 | 83.6682 | 82.8882 | 115.4942 | 134.3066 |
| 10 | 110.9331 | 87.4832 | 94.7827 | 126.9308 | 126.9563 |
| 11 | 104.7781 | 90.9168 | 91.6629 | 115.8926 | 121.7848 |
| 12 | 95.5881 | 94.2910 | 90.7557 | 107.3639 | 115.6807 |
| 13 | 108.6440 | 100.5561 | 93.3923 | 131.4241 | 124.4723 |
| 14 | 119.8518 | 22.6868 | 33.7962 | 107.0587 | 117.7832 |
| 15 | 42.7896 | 41.6603 | 42.4742 | 46.8488 | 69.4135 |
| 16 | 27.2445 | 37.0416 | 56.8493 | 49.6668 | 70.0341 |
| 17 | 17.0914 | 33.2163 | 55.5267 | 49.3209 | 69.7391 |
| 18 | 22.4223 | 44.2139 | 65.4052 | 52.9325 | 76.1483 |
| 19 | 29.5030 | 48.4257 | 54.3975 | 75.3446 | 80.1567 |
| 20 | 33.0536 | N/A | N/A | 54.8227 | 80.0753 |
| 21 | 41.6603 | N/A | N/A | N/A | N/A |

TABLE 9d-continued

| | Control | Biotin | Grapeseed + Biotin | Skullcap + Biotin | Eclipta + Biotin |
|---|---|---|---|---|---|
| MEAN | 80.0076 | 79.2167 | 86.7126 | 101.5187 | 116.7690 |
| SEM | 8.30017 | 7.2726 | 6.7175 | 7.66597 | 7.0158 |
| T-TEST (to Control) | | 0.471881 | 0.2695607 | 0.0324942* | 0.000861*** |
| % Change vs Control | 0.0% | −1.0% | 8.4% | 26.9% | 45.9% |
| T-TEST (to Biotin) | | | 0.226944 | 0.021013* | 0.000331*** |
| % Change vs Biotin | | | 9.5% | 28.2% | 47.4% |

HDPSC cells were treated 72 h with grapeseed, skullcap, and eclipta extracts in presence of 18% oxygen increase luciferase signal (arbitrary units) above control.
Data represent means ± SEM of 19-20 replicate measurements.
* = significant difference, $p < 0.05$, , and ** = highly significant difference, $p < 0.01$, students t-test.
↑ = positive result, not statistically significant.
Units are arbitrary luminescence values measured at 560 ± 10 nm.

Table 9e shows the relative effects (Control=100) of Single extracts with and without Biotin on Wnt/beta-Catenin Signaling in HDPSCs TopFlash transfected HDPSCs.

TABLE 9e

| | Control | Biotin | Grapeseed | Skullcap | Eclipta |
|---|---|---|---|---|---|
| No Biotin | 100 | 97 | 132 | 194 | 274 |
| With Biotin | 100 | 99 | 108 | 127 | 146 |

Referring to FIG. 1, Comparison of Relative Effects of HDPSC cells increase in luciferase signal (arbitrary units) above control treated 72 h with grapeseed, skullcap, and eclipta extracts with and without Biotin in presence of 18% oxygen. Data represent means as % of Control.

Table 10 shows the summary effects of single treatments on luciferase activity (Wnt/beta-Catenin Signalling) in TopFlash transfected HDPSCs.

TABLE 10

| Ingredient | Dilutions | Wnt/β-catenin Signal Upregulation | Statistical Significance |
|---|---|---|---|
| Biotin | $10^{-3}$ | No Effect | — |
| Grapeseed | $10^{-3}$ | +31.6% | *** |
| Skullcap | $10^{-3}$ | +93.6% | *** |
| Eclipta | $10^{-3}$ | +173.6% | *** |

In Table 10, *** = highly significant difference, $p < 0.001$.

Figure 2:
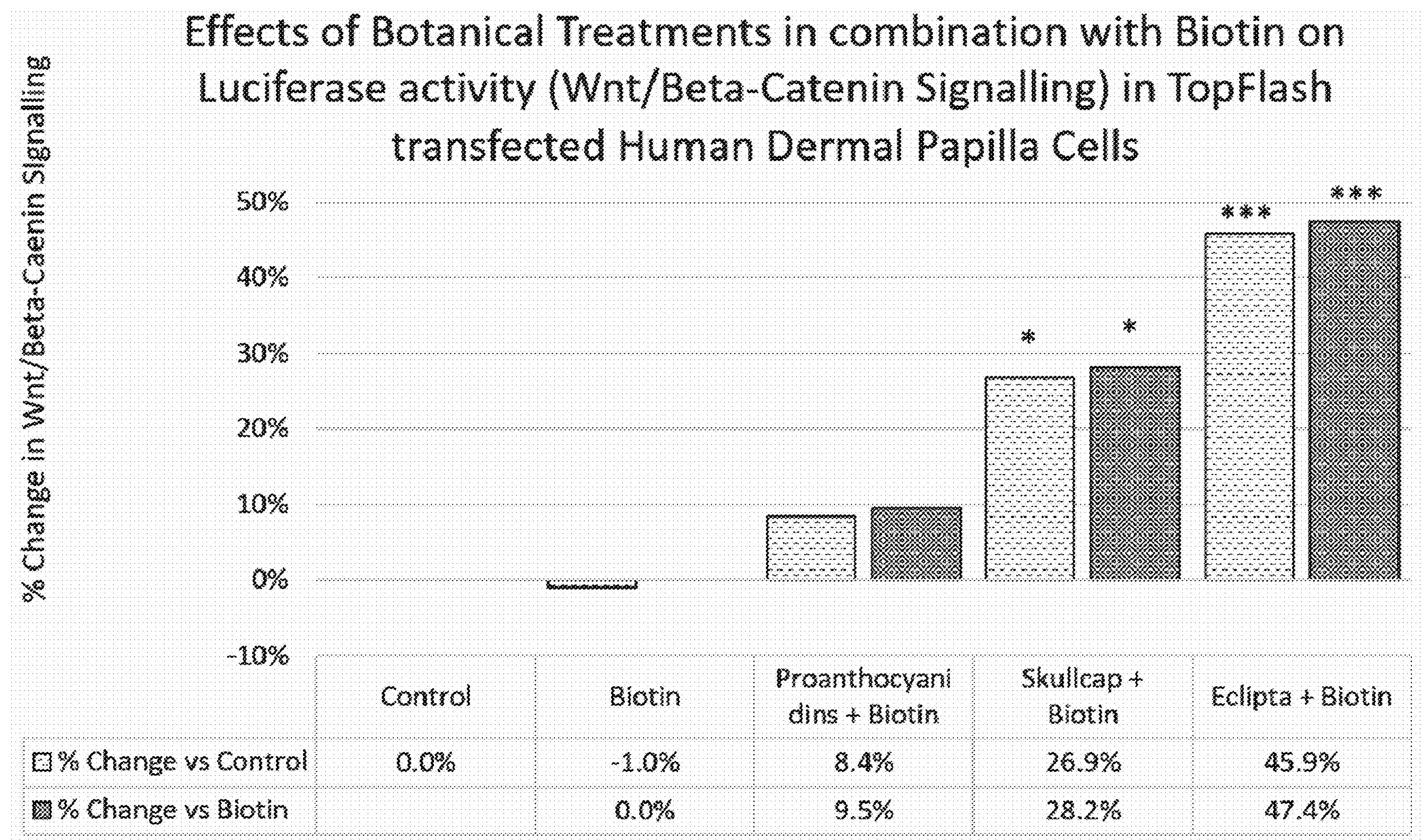
FIG. 2 is a bar graph showing the effects of Botanical Treatments in combination with Biotin on Wnt/beta-Catenin Signaling.

Table 11 shows the summary effects of combination treatments of botanicals with biotin on luciferase activity (Wnt/beta-Catenin Signalling) in TopFlash transfected HDPSCs. See FIG. 2.

TABLE 11

| Combinations | Ratio | Dilutions | Wnt/β-catenin Signal Upregulation of Combinations vs Control | Wnt/β-catenin Signal Upregulation of Combinations vs Biotin |
|---|---|---|---|---|
| Grapeseed: Biotin | 7.5:1 | $10^{-3}$ | +8% (↑) | +9.5% (↑) |
| Skullcap:Biotin | 6.8:1 | $10^{-3}$ | +27% (↑*) | +28.2% (↑*) |
| Eclipta:Biotin | 12:1 | $10^{-3}$ | +46% (↑***) | +47.4% (↑***) |

In Table 11 * = significant difference, $p < 0.05$ and *** = highly significant difference, $p < 0.001$, Students T-Test, ↑ = positive result versus either Control or Biotin.

Botanical extracts of Proanthocyanadins from grapeseed, skullcap, and eclipta, each in combination with Biotin increase Wnt/beta-Catenin Signaling in HDPSC's with statistical significance in the Skullcap and *Eclipta* combinations with Biotin.

Biotin Found to Promote and Decrease Stem Cell Proliferation and Also Attenuate or Inhibit Wnt Activation in HDPSC's Biotin at concentrations of at least $10^{-3}$ promote proliferation of stem cells, as per Table 6 yet at concentrations at not more than $10^{-5}$, Biotin has shown to decrease the stem cell population as per Table 7. The results further demonstrate, as per Table 8, that at the same concentrations of Biotin and ratios with botanical extracts that demonstrated Biotin as a potentiator of HDPSC proliferation, Biotin also attenuates or inhibits the effect of Wnt signaling activated by the extracts, yet the extracts can overcome this attenuating effect. This counter-point result of Biotin as both a potentiator and simultaneously an attenuator is significant, since Biotin is present in vivo. The findings further demonstrates that extracts are able to activate Wnt in the presence of Biotin, suggesting they will do so in vivo.

The in vitro results are definitive and the first to demonstrate that the mechanism by which individual botanicals such as grapeseed, skullcap, eclipta activate HDPSCs is through the Wnt/β-catenin pathway. The results are also definitive in demonstrating that the extracts and biotin in the correct concentrations and mixed ratios, will proliferate HDPSC's and in combination with the extracts, Biotin will potentiate the proliferation of the HDPSC's. This will ultimately cause tissues to regenerate by activating the Wnt/ beta-Catenin signaling and thus retard aging and treat or prevent diseases related to signal transduction or attenuation.

Example 9: The Optimal Stock Concentrations and Dilutions of Extracts and Biotin Biotin 0.25 mg/mL stock (1:100 dilution);
Grapeseed 7.5 mg/mL stock (1:1000 dilution);
Skullcap 1.7 mg/mL stock (1:1000 dilution);
*Eclipta* 3.0 mg/mL stock (1:100 dilution).

Biotin:

- Biotin solution of 0.25 mg/mL stock (1:100 dilution):
- tested under MTT assay for HDPSC growth sensitivity (n=3) showed positive results at dilution of $10^{-3}$ with cell proliferation rates at 152%.
- tested under MTT assay for HDPSC growth sensitivity (n=30) showed statistically significantly negative results at dilution of $10^{-5}$ with cell population declining by 21%.
- tested for Wnt signaling had no effect in HDPSC's.
- tested in combination with botanical extracts that upregulate Wnt/beta-Catenin signaling, Biotin was found to have an attenuating or inhibiting effect.

Conclusions

- Biotin at concentrations of at least 0.25 mg/mL stock diluted at least 10 parts per million or 2.5 mcg/kg bioavailable as per human metabolic rate promotes HDPSC proliferation without upregulating Wnt/beta-Catenin signaling.
- Biotin has an attenuating effect on Wnt/beta-Catenin signaling.
- Biotin at concentrations of less than 0.25 mg/mL stock diluted at least 1 part per 10 million or 0.025 mcg/kg bioavailable as per human metabolic rate causes a decline in HDPSC populations.

Grapeseed:

- Grapeseed 7.5 mg/mL stock (1:1000 dilution);
- tested under MTT assay for HDPSC growth sensitivity (n=3) showed positive results at dilution of $10^{-2}$ and $10^{-3}$ with cell proliferation rates at 118%, and 136% with statistical significance respectively.
- tested under MTT assay in combination with biotin at ratios of grapeseed to biotin from 7.5:1 to 30:1 at concentrations of $10^{-3}$ in varying oxygen concentrations from 5% to 19%, HDPSC proliferation was statistically significant.
- tested for Wnt signaling upregulation against a control at concentration of $10^{-3}$ was 31.6% and highly statistically significant.
- tested for Wnt signaling upregulation in combination with biotin at ratio of grapeseed to biotin from 7.5:1 at concentration of $10^{-3}$ against a control was 9.3%.

Conclusions

- Grapeseed at concentrations of at least 7.5 mg/mL stock diluted at least 1 part per million or 7.5 mcg/kg bioavailable as per human metabolic rate promotes HDPSC proliferation and upregulating Wnt/beta-Catenin signaling.
- Grapeseed upregulation of Wnt/β-Catenin signaling is attenuated in the presence of biotin.
- Grapeseed has the ability to overcome the attenuating effect of Biotin on Wnt/beta-Catenin signaling.
- Grapeseed activates Wnt/beta-Catenin.

Skullcap:

- Grapeseed 1.7 mg/mL stock (1:1000 dilution);
- tested under MTT assay for HDPSC growth sensitivity (n=3) showed positive results at dilutions of $10^{-2}$ and $10^{-3}$ with cell proliferation rates at 107% and 108%.
- tested under MTT assay in combination with biotin at ratios of grapeseed to biotin from 4:1 to 6.8:1 at concentrations of $10^{-3}$, $10^{-4}$, $10^{-5}$ in varying oxygen concentrations from 5% to 19%, HDPSC proliferation rates varied from 103% to 130% and were statistically significant.
- tested for Wnt/beta-Catenin signaling upregulation compared to control at concentration of $10^{-3}$ was 93.6% and highly statistically significant.
- tested for Wnt/beta-Catenin signaling upregulation in combination with biotin at ratio of skullcap to biotin from 6.8:1 at concentration of $10^{-3}$ against a control was 26.2% and was statistically significant.

Conclusions

- Skullcap at concentration of at least 1.7 mg/mL stock diluted at least 1 part per million or 1.7 mg/kg bioavailable as per human metabolic rate promotes HDPSC proliferation and upregulating Wnt/beta-Catenin signaling.
- Skullcap upregulation of Wnt/beta-Catenin signaling is attenuated in the presence of biotin.
- Skullcap has the ability to overcome the attenuating effect of Biotin on Wnt/beta-Catenin signaling.
- Skullcap activates Wnt/beta-Catenin.

Edlipta:

- *Eclipta* 3.0 mg/mL stock (1:100 dilution).
- tested under MT assay for HDPSC growth sensitivity (n=3) showed positive results at dilution of $10^{-1}$ to 10-5 with cell proliferation rates at, 122% to 141% with statistical significance at dilutions of $10^{-2}$ land $10^{-3}$.
- tested under MT assay in combination with biotin at ratios of eclipta to biotin from 12:1 at concentrations of $10^{-3}$, $10^{-4}$, $10^{-5}$ in varying oxygen concentrations from, HDPSC proliferation rates varied from 133% to 175% and were statistically significant.
- tested for Wnt signaling upregulation compared to control at concentration of $10^{-3}$ was 173.6% and highly statistically significant.
- tested for Wnt/beta-Catenin signaling upregulation in combination with biotin at ratio of skullcap to biotin from 12:1 at concentration of $10^{-3}$ against a control was 41.1% and was highly highly statistically significant.

Conclusions

- *Eclipta* at concentration of at least 3.0 mg/mL stock diluted at least 1 part per 10 million or 0.3 mcg/kg bioavailable as per human metabolic rate promotes HDPSC proliferation and upregulating Wnt/beta-Catenin signaling.
- *Eclipta* upregulation of Wnt/beta-Catenin signaling is attenuated in the presence of biotin.
- *Eclipta* has the ability to overcome the attenuating effect of Biotin on Wnt/beta-Catenin signaling.
- *Eclipta* activates Wnt/β-catenin Example 10: Formula I—Grapeseed In one aspect the invention comprises Grapeseed (*Vitis vinifera*) as described below.

Formula I.a. Grapeseed and grapeseed extracts including polyphenol compounds including proanthocyanadins as monomers and or oligomers.

Formula I.b. Grapeseed as in Formula I.a at least 7.5 mg/mL stock diluted at least 1 part per 15,000 bioavailability, as per human metabolic rate.

Formula I.c. Grapeseed as in Formula I.a. or I.b. at least 112.5 mg/kg bioavailability, as per human metabolic rate.

Formula I.d. Grapeseed extract an approximate extract ratio of 10:1 to 15:1 from original dry grapeseed material.

Formula I.e. Grapeseed extract standardized to >=95% polyphenols as proanthocyanadins, as >=85% oligomeric proanthocyanadins and 5-15% monomer proanthocyanadins.

Formula I.f. Grapeseed extract concentration as in Formula I.d or I.e of 7.5 mg/mL stock diluted at least 1 part per thousand bioavailable as per human metabolic rate.

Formula I.g. Grapeseed extract as in Formula I.d. or I.e. at least 7.5 mg/kg bioavailability, as per human metabolic rate.

Formula I.h. Grapeseed and Biotin. Formula I.a and biotin with ratios of grapeseed to Biotin of 75 to 300 parts grapeseed to 1 part Biotin or Formula I.d or I.e and Biotin with ratios of skullcap to Biotin of 7.5 to 30 parts grapeseed extract to 1 part Biotin.

Example 11: Formula II—Skullcap

In one aspect the invention comprises Skullcap: (*Scutellaria baicalensis*; syn. huang qin) as described below.

Formula II.a. Skullcap: and skullcap extracts primarily from the root, including any and all of the Flavones compounds; baicalin, baicalein or wogonin, and sterols.

Formula II.b. Skullcap root as in Formula II.a at least 1.7 mg/mL stock diluted at least 1 part per 12,000 bioavailability as per human metabolic rate.

Formula II.c. Skullcap extract concentration as in Formula II.a. or II.b. at least 1.7 mg/kg bioavailability as per human metabolic rate.

Formula II.d. Skullcap extracts from original plant material approximate extract ratio of 12:1

Formula II.e. Skullcap extracts standardized to 30% flavones as baicalin

Formula II.f. Skullcap extract concentration as in Formula II.c. or II.d. at least 1.7 mg/mL stock diluted at least 1 part per thousand as per human metabolic rate.

Formula II.g. Skullcap extract concentration as in Formula II.c. or II.d. at least 1.7-mg/kg bioavailability as per human metabolic rate.

Formula II.h. Skullcap and Biotin. Formula II.a or II.b and Biotin with ratios of skullcap to Biotin of 48 to 81.6 parts skullcap to 1 part Biotin or Formula II.c or II.d and Biotin with ratios of skullcap extract to biotin of 4 to 6.8 parts skullcap to 1 part Biotin.

Example 12: Formula III—*Eclipta*

In one aspect the invention comprises *Eclipta* (*Eclipta prostrata*; syn. *Eclipta alba*; syn. Han Dan Cao) as described below Formula III.a. *Eclipta* and eclipta extracts from the whole plant, with any or all of compounds including lactones such as wedelolactone, tannins, saponins, nicotine, ecliptine, 2, methylbutanal oxime, Catechol, Uracil, Phenyl ethylamine, Nicotinic acid, 4-hydroxybenzoic acid, 3,4-dihydroxybenzoic acid, Dihydrocarveol, L-nicotene, Gallic acid, Catechol derivative, Caryophyllene oxide, Coumestan, Apigenin, Butein, α-terthienyl methanol, Indolylmethyl glucosinolate, Luteolin, Testosterone, 2-Terthiophene-5-carboxylic acid, Demethylwedelolactone, Wedelolactone, Tyramine β xanthine, Gallic acid hexoxide, Quercetin derivative, Catechin derivative, 16-methoxytabersonine, Stigmasterol, β sitosterol, β-amyrin, Hypophyllanthin, Apigenin-7-O-glucoside, Epicatechin, Quercetin-3-rhamnoside, Cynaroside, Demethylwedelolactone 7-glucoside, Galloyl-isorhamnetin, Echinocystic acid, Caulophyllogenin, Myoinositol.

Formula III.b. *Eclipta* as in Formula III.a. at least 3.0 mg/mL stock diluted at least 1 part per 10,000 bioavailability as per human metabolic rate.

Formula III.c. *Eclipta* as in Formula III.a. or III.b. at least 3.0 mg/kg bioavailablity as per human metabolic rate.

Formula III.d. *Eclipta* extracts from original whole plant material approximate extract ratio of 10:1

Formula III.e. *Eclipta* extracts standardized to 5% lactones as wedelolactone

Formula III.f. *Eclipta* extract concentration as in Formula III.d. or III.e. at least 3.0 mg/mL stock diluted at least 1 part per 1,000 bioavailable as per human metabolic rate.

Formula III.g. *Eclipta* extract concentration as in Formula III.d. or III.e. at least 3.0 mg/kg bioavailablity as per human metabolic rate.

Formula III.h. *Eclipta* and Biotin. Formula II.a, III.b, and biotin with ratios of eclipta to Biotin of 120 parts eclipta to 1 part biotin or Formula III.d or III.e and Biotin with ratios of eclipta to biotin of 12 parts eclipta to 1 part biotin, all diluted to 1 part per 1000.

Example 13: Formula IV—Biotin

In one aspect the invention comprises Biotin as described below

IV.a. Biotin concentration of at least 0.25 mg/mL stock diluted at least 10 parts per million bioavailable as per human metabolic rate.

Formula IV.b. Biotin extract concentration of at least 2.5 mg/kg bioavailable as per human metabolic rate.

Example 14: Formula V

In one aspect the invention comprises a combination of grapeseed and skullcap as described below Formula V.a. Grapeseed and Skullcap Formula V.b. Grapeseed and Skullcap and Biotin Formula V.c. Any combination of Formula I and II and/or IV Example 15: Formula VI In one aspect the invention grapeseed and eclipta as described below.

Formula VI.a. Grapeseed and *Eclipta*

Formula VI.b. Grapeseed and *Eclipta* and Biotin

Formula VI.c. Any combination of Formula I and III and/or IV

Example 16: Formula VII

In one aspect the invention comprises Skullcap and *Eclipta* as described below

Formula VII.a. Skullcap and *Eclipta*

Formula VII.b. Skullcap and *Eclipta* and Biotin

Formula VII.c. Any combination of Formula II and III and/or IV

Example 17: Formula VIII

In one aspect the invention comprises grapeseed, skullcap, and eclipta as described below Formula VIII.a. Grapeseed, Skullcap and *Eclipta*

Formula VIII.b. Grapeseed, Skullcap, *Eclipta* and Biotin

Formula VIII.c. Any combination of Formula I, II, III and/or IV

Example 18: Formula IX

In one aspect the invention comprises Biotin as described below

IX.a. Biotin concentration of less than or equal to 0.25 mg/mL stock diluted at least 1 parts per 10 million bioavailable as per human metabolic rate.

Formula IX.b. Biotin extract concentration of less than or equal to 0.025 mg/kg bioavailable as per human metabolic rate.

Example 19: Formulation X—Topical Application Preparation

In one aspect the invention comprises the topical formulation as described in Table 12 below.

TABLE 12

Botanicals For Topical Formulations.

| Botanical | Common Name | Part |
|---|---|---|
| *Chenopodium quinoa* | Quinoa | Seed |
| *Eclipta prostrata* | Han Lian Cao | Whole Plant |
| *Lupinus* | Lupine | Seeds |
| *Malus domestica* | Apple | Fruit |
| *Momordica charantia* | Bitter Melon | Fruit |
| *Moringa olifiera* | Moringa | Seed |
| *Ocimum basilicum* | Basil | Root |
| *Pisum sativum* | Pea | Whole Plant |
| *Rosmarinus officinalis* | Rosemary | Leaf & Stem |
| *Scutellaria baicalensis* | Skullcap | Root |
| *Vitis viniferis* | Grape Seed | Seed |

Table 13 shows the botanical extracts preferred in the the topical formulation.

TABLE 13

Botanical Extracts Preferred for Topical Formulations

| Botanical | Approximate Extract Ratio | Preferred Standardization | Preferred Constituents |
|---|---|---|---|
| *Chenopodium quinoa* | | | |
| *Eclipta prostrata* | 10 | 5% lactones as wedelolactone | Tannins, saponins, nicotine, ecliptine |
| *Lupinus* | | | |
| *Malus domestica* | 30 | 50% Polyphenols by UV | Polyphenols, pectin, potassium |
| *Momordica charantia* | 10 | 5% bitter principles by UV | Charantin, momordicosides, momordicine |
| *Moringa olifiera* | | | |
| *Ocimum basilicum* | | | |
| *Pisum sativum* | | | |
| *Rosmarinus officinalis* | | | |
| *Scutellaria baicalensis* | 12 | 30% flavones as baicalin by UV | Flavones (baicalin, baicalein, wogonin)sterols |
| *Vitis viniferis* | 10-15 | >=95% Proanthocyanadins as Catechins by HPLC | 5-15% Catechin Monomers, >=80% Procyanidolic Oligomers |

Table 14 shows the concentration ranges for the topical active ingredients by percent weight.

TABLE 14

Topical Active Ingredient Concentration Ranges

| Ingredients | Min | Max |
|---|---|---|
| Biotin | 0.005% | 1.00% |
| Caffeine | 0.0001% | 1.00% |
| *Chenopodium quinoa* | 0.1% | 2.00% |
| *Eclipta prostrata* | 0.01% | 4.00% |
| *Lupinus* | 0.01% | 6.00% |
| *Malus domestica* | 0.01% | 4.00% |
| Methylsulfonylmethane | 0.005% | 2.00% |
| *Momordica charantia* | 0.01% | 4.00% |
| *Moringa olifiera* | 0.01% | 6.00% |
| *Ocimum basilicum* | 0.01% | 6.00% |
| *Pisum sativum* | 0.01% | 6.00% |
| *Rosmarinus officinalis* | 0.01% | 4.00% |
| *Scutellaria baicalensis* | 0.01% | 4.00% |
| Vitamin E (Alpha tocopherol) | 0.005% | 2.00% |
| *Vitis viniferis* | 0.01% | 4.00% |

Table 15 shows the minimum and maximum concentrations of the primary active ingredients by percent weight.

TABLE 15

Essential Topical Ingredient Concentration Ranges
Select at least 1 of Eclipta, Scutellaria or Vitis with or without

| Ingredients | Min | Max |
|---|---|---|
| Biotin | 0.00% | 1.00% |
| *Eclipta prostrata* | 0.01% | 4.00% |
| *Scutellaria baicalensis* | 0.01% | 4.00% |
| *Vitis viniferis* | 0.01% | 4.00% |

Table 16 shows the preferred concentration of essential topical active ingredients by percent weight.

TABLE 16

Essential Topical Active Ingredient Preferred Concentration
Scalp & Skin Creams

| Ingredients | Shampoo | Hair Conditioner | Scalp & Skin Creams or Serum |
|---|---|---|---|
| Biotin | 0.025% | 0.025% | 0.025% |
| *Eclipta prostrata* | 0.03% | 0.15% | 0.30% |
| *Scutellaria baicalensis* | 0.10% | 0.10% | 0.17% |
| *Vitis viniferis* | 0.19% | 0.56% | 0.75% |

Table 17 shows the preferred active ingredient concentration by weight.

TABLE 17

| Topical Preferred Active Ingredient Concentration | | | |
|---|---|---|---|
| Ingredients | Shampoo ALRVXR-S00 | Hair Conditioner ALRVXR-C00 | Scalp & Skin Creams or Serum ALRVXR-N00 |
| Biotin | 0.025% | 0.025% | 0.025% |
| Caffeine | 0.0010% | 0.0010% | 0.0010% |
| *Chenopodium quinoa* | 0.50% | 0.50% | 1.50% |
| *Eclipta prostrata* | 0.03% | 0.15% | 0.30% |
| *Lupinus* | 1.00% | 2.50% | 2.50% |
| *Malus domestica* | 0.06% | 0.19% | 0.25% |
| *Methylsulfonylmethane* | 0.80% | 0.80% | 0.80% |
| *Momordica charantia* | 0.05% | 0.10% | 0.20% |
| *Moringa olifiera* | 1.00% | 2.00% | 2.00% |
| *Ocimum basilicum* | | | 2.00% |
| *Pisum sativum* | | | 4.00% |
| *Rosmarinus officinalis* | 0.03% | 0.03% | 0.30% |
| *Scutellaria baicalensis* | 0.10% | 0.10% | 0.17% |
| Vitamin E (Alpha tocopherol) | 0.20% | 0.40% | 0.50% |
| *Vitis viniferis* | 0.19% | 0.56% | 0.75% |

Table 18 shows the preferred fragrance range by weight.

TABLE 18

| Topical Ingredient Fragrance Ranges | | |
|---|---|---|
| Essential Oils | Min | Max |
| *Cedrus deodora* | — | 1.00% |
| *Juniperus virginiana* | — | 1.00% |
| *Matricaria chamomilla* | — | 1.00% |
| *Anthemis nobilis* | — | 1.00% |
| *Helichrysium angustifolia* | — | 1.00% |
| *Jasminium grandiflorum* | — | 1.00% |
| *Lavandula angustifolia* | — | 1.00% |
| *Mentha piperita* | — | 5.00% |
| Citrus x sinensis | — | 4.00% |
| *Achillea millefolium* | — | 1.00% |
| Citrus bergamia | — | 1.00% |
| Calendula | — | 1.00% |
| Tea Tree | — | 1.00% |

Table 19 shows preferred fragrance ranges in an embodiment of the present invention.

TABLE 19

| Topical Ingredient Preferred Fragrance Ranges | | | |
|---|---|---|---|
| Essential Oils | Shampoo ALRVXR-S00F | Hair Conditioner ALRVXR-C00F | Scalp & Skin Creams or Serum ALRVXR-N00F |
| *Cedrus deodora* | 0.0245% | 0.0245% | 0.0280% |
| *Juniperus virginiana* | 0.0140% | 0.0140% | 0.0140% |
| *Matricaria chamomilla* | | | 0.0007% |
| *Anthemis nobilis* | 0.0035% | 0.0035% | 0.0000% |
| *Helichrysium angustifolia* | | | 0.0004% |
| *Jasminia grandiflorum* | | | 0.0035% |
| *Lavandula angustifolia* | 0.0280% | 0.0280% | 0.0228% |
| *Achillea millefolium* | | | 0.0007% |

Table 20 shows a representative formulations of shampoo, conditioner and a cream or serum by percent weight.

TABLE 20

| Representative Topical Cosmetic and Mixing Agent Concentrations | | | |
|---|---|---|---|
| Ingredients | Shampoo ALRVXR-S00M | Hair Conditioner ALRVXR-C00M | Scalp & Skin Creams or Serum ALRVXR-N00M |
| Aqua | 66.464 | 73.324 | 69.67 |
| *Aloe barbadensis* | 0.01 | — | — |
| Distearoylethyl dimonium chloride | — | 5 | 7.5 |
| Cetearyl alcohol | — | 3 | 3 |
| Cocomidopropyl betain | 9 | — | — |
| *Cocos nucifera* | 0.1 | 3 | 0.1 |
| Glycerin | 3 | 6 | 3 |
| Glyceryl caprylate | 0.5 | 0.5 | 0.5 |
| Glyceryl undecylenate | 0.5 | 0.5 | 0.5 |
| Guar hydroxypropyl-trimonium chloride | — | 0.3 | 0.3 |
| Glycol distearate | 0.6 | — | — |
| Hydroxypropyl methylcellulose | 0.55 | — | — |
| Jojoba esters | — | 0.5 | 0.5 |
| Panthenol | — | 0.25 | 0.25 |
| Sodium cocoyl isethionate | 4 | — | — |
| Sodium lauroyl methyl isethionate | 6 | — | — |
| Sodium laurylglucosides hydroxypropylsulfonate | 6 | — | — |
| *Butyrospermum parkii* | — | 1 | 0.1 |

Example 20: Formulation XI—Internal Administration

In one aspect the invention comprises the ingestible formulation as described below.

Table 21 shows an average BMI and weight for a typical patient.

TABLE 21

| Reference Body Mass Index (BMI) and Weights (kg/lb) | | | |
|---|---|---|---|
| Adult | BMI | kg | lb |
| Male | 24.4 | 76 | 167 |
| Female | 22.8 | 61 | 134 |

Adapted from USA Third National Health and Nutrition Examination Survey (NHANES III), 1988-1994, as a reference guide to recommended daily intake of nutrients. Reference Body Mass Index(BMI) ($Kg/m^2$), and Weights (kg/lb) for Adults in USA Table 22 shows preferred botanicals for the ingestible formulation.

TABLE 22

| Botanicals For Ingestible Formulations | | |
|---|---|---|
| Botanical | Common Name | Part |
| *Angelica sinensis* | Dong Quai | Root |
| *Withania somnifera* | Ashwaganda | Root |
| *Astragalus membranaceus* | Astragalus | Root |
| *Eclipta prostrata* | Han Lian Cao | Whole Plant |
| *Ganoderma lucidum* | Reishi | Fruiting Body |
| *Ascophyllum nodosum* | Norwegan Kelp | Whole Plant |
| *Malus domestica* | Apple | Fruit |
| *Moringa oleifera* | Moringa | Leaf |
| *Polygonum multiflorum* | Fo Ti (He Shou Wu) | Root |
| *Punica granatum* | Pomegranate | Fruit |
| *Rosmarinus officinalis* | Rosemary | Leaf & Stem |
| *Scutellaria baicalensis* | Skullcap | Root |
| *Sophora flavescens* | Ku Shen | Root |
| *Vitis viniferis* | Grape Seed | Seed |

Table 23 shows preferred extracts for the ingestible formulation.

TABLE 23

| Botanical Extracts Preferred for Ingestible Formulations | | | |
|---|---|---|---|
| Botanical | Approximate Extract Ratio | Preferred Standardization | Preferred Constituents |
| *Angelica sinensis* | 10 | 1% lactones as ligustilide by HPLC | Butylidenphthalide, ligustilide, vitamins, polysaccharides |
| *Ascophyllum nodosum* | 1 | 0.5% Iodine | Iodine |
| *Withania somnifera* | 1 | | Alkaloids (isopelletierine, anaferine, cuseohygrine, anahygrine), Steroidal Lactones (withanolides, withaferins) and saponins |
| *Astragalus membranaceus* | 12 | 4% isoflavones using formonetin std. by UV | Isoflavones. Amino acids, Choline, Betaine, Saponins |
| *Eclipta prostrata* | 10 | 5% lactones as wedelolactone | Tannins, saponins, nicotine, ecliptine |
| *Ganoderma lucidum* | 10 | 10% polysaccharides by UV | Ergosterols, polysaccharides, vitamins, minerals |
| *Malus domestica* | 30 | 50% polyphenols by UV | Polyphenols, pectin, potassium |
| *Moringa oleifera* | 4 | | Amino Acids, Minerals, Vitamins, Potassium |
| *Polygonum multiflorum* | 16 | 8% stilbenes by UV | Anthraquinones, stilbenes, catechins |
| *Punica granatum* | 25 | 40% ellagic acid by HPLC | Ellagic Acid, Polyphenols, Potassium |
| *Rosmarinus officinalis* | 10 | 10% carnosic acid | Apigenin-7-glucoside, luteolin-7-glucoside, diosmin, rosmarinic acid, carnosic acid |
| *Scutellaria baicalensis* | 12 | 30% flavones as baicalin by UV | Flavones (baicalin, baicalein, wogonin), sterols |
| *Sophora flavescens* | 12 | 8% alkaloids | Flavonoids, alkaloids (matrine, oxymatrine) |
| *Vitis viniferis* | 10-15 | >=95% Proanthocyanadins as Catechins by HPLC | 5-15% Catechin Monomers, >=80% Procyanidolic Oligomers |

Table 24 shows the by weight the range of extracts for a daily dosage.

TABLE 24

| Composition Ranges of Daily Dosage of Botanical Extracts for the Ingestible Embodiment | | | | |
|---|---|---|---|---|
| | Dry Herb Equivalent (DHE) | | | |
| Botanical | Min (mg) | | Max (mg) | Extract* Max (mg) |
| *Angelica sinensis* | 0 | — | 600 | 60 |
| *Ascophyllum nodosum* | 0 | — | 21 | 21 |
| *Withania somnifera* | 0 | — | 5000 | 5000 |
| *Astragalus membranaceus* | 0 | — | 600 | 50 |
| *Eclipta prostrata* | 0 | — | 4000 | 400 |
| *Ganoderma lucidum* | 0 | — | 500 | 50 |
| *Malus domestica* | 0 | — | 1000 | 33.3 |
| *Moringa oleifera* | 0 | — | 2000 | 500 |
| *Polygonum multiflorum* | 0 | — | 750 | 47 |
| *Punica granatum* | 0 | — | 750 | 30 |
| *Rosmarinus officinalis* | 0 | — | 1000 | 100 |
| *Scutellaria baicalensis* | 0 | — | 600 | 50 |
| *Sophora flavescens* | 0 | — | 1200 | 100 |
| *Vitis viniferis* | 0 | — | 3000 | 300 |

*DHE prevails as the reference dosage, unless the Extract standardization remains constant Table 25 shows the range by weight of the primary active agents for the ingestible formulation.

TABLE 25

| Essential Composition Ranges of Daily Dosage of Botanical Extracts for the Internal Embodiment Select at least 1 of Eclipta, Scutellaria or Vitis | | | | |
|---|---|---|---|---|
| | Dry Herb Equivalent (DHE) | | | |
| Botanical | Min (mg) | | Max (mg) | Extract* Max (mg) |
| *Eclipta prostrata* | 0 | — | 4000 | 400 |
| *Scutellaria baicalensis* | 0 | — | 1000 | 50 |
| *Vitis viniferis* | 0 | — | 3000 | 300 |

*DHE prevails as the reference dosage, unless the Extract standardization remains constant Table 26 shows various ranges of the preferred actives in the ingestible form of the present invention.

TABLE 26

Preferred Composition of Daily Dosage of Essential Botanical Extracts for the Ingestible Embodiment

| Formulation: Botanical | 1 ALRVXR-D00 (mg) | 2 ALRVXR-D02 (mg) | 3 ALRVXR-D06 (mg) | 4 ALRVXR-D08 (mg) | 5 ALRVXR-D10 (mg) | 6 ALRVXR-D12 (mg) | 7 ALRVXR-D14 (mg) |
|---|---|---|---|---|---|---|---|
| *Eclipta prostrata* | 33 | 300 | 200 | 100 | 300 | 50 | 200 |
| *Scutellaria baicalensis* | 20 | 20 | 50 | 20 | 20 | 50 | 50 |
| *Vitis viniferis* | 100 | 150 | 100 | 300 | 300 | 100 | 200 |

Daily Dosage per Adult Reference BMI and Weight. Actual dosage may adjust to patient
Formulation based on Extracts in Table X relative to the Dry Herb Equivalents (DHE) or the Standardized Compounds. Changes in commercially available extracts always reference the dosage to the DHE or Standardized compounds.

Table 27 shows various preferred formulation of the ingestible composition.

TABLE 27

Preferred Composition of Daily Dosage of Botanical Extracts for the Ingestible Embodiment

| Formulation: Botanical | 1 ALRVXR-D00 (mg) | 2 ALRVXR-D02 (mg) | 3 ALRVXR-D06 (mg) | 4 ALRVXR-D08 (mg) | 5 ALRVXR-D10 (mg) | 6 ALRVXR-D12 (mg) | 7 ALRVXR-D14 (mg) |
|---|---|---|---|---|---|---|---|
| *Angelica sinensis* | 33 | 33 | — | 33 | 33 | — | 33 |
| *Ascophyllum nodosum* | 21 | 21 | 21 | 21 | 21 | 21 | 21 |
| *Withania somnifera* | — | — | — | — | — | — | 250 |
| *Astragalus membranaceus* | 17.5 | 17.5 | — | 17.5 | 17.5 | — | 17.5 |
| *Eclipta prostrata* | 33 | 300 | 200 | 100 | 300 | 50 | 200 |
| *Ganoderma lucidum* | 10 | 10 | 50 | 10 | 10 | 30 | 10 |
| *Malus domestica* | 13.3 | 13.3 | 33.3 | 13.3 | 13.3 | 33.3 | 33.3 |
| *Moringa oleifera* | 100 | 300 | 250 | 200 | 100 | 250 | 250 |
| *Polygonum multiflorum* | 37.5 | 37.5 | 37.5 | 37.5 | 37.5 | 37.5 | 37.5 |
| *Punica granatum* | 16 | 16 | 30 | 16 | 16 | 30 | 30 |
| *Rosmarinus officinalis* | 36 | 36 | 36 | 36 | 36 | 36 | 36 |
| *Scutellaria baicalensis* | 20 | 20 | 50 | 20 | 20 | 50 | 50 |
| *Sophora flavescens* | 50 | 50 | 50 | 50 | 50 | 50 | 50 |
| *Vitis viniferis* | 100 | 150 | 100 | 300 | 300 | 100 | 200 |

Daily Dosage per Adult Reference BMI and Weight. Actual dosage may adjust to patient Formulation based on Extracts in Table 23 relative to the Dry Herb Equivalents (DHE) of Table 24 or the Standardized Compounds. Changes in commercially available extracts always reference the dosage to the DHE or Standardized compounds.

Table 28 shows the preferred range of biotin in an ingestible formulation.

TABLE 28

Essential Composition Ranges of Daily Dosage of Vitamins, Minerals and Amino-Acids for the Ingestible Embodiment

| Ingredient | Min | Max |
|---|---|---|
| Biotin | 0 | 5,000 mcg |

Daily Dosage per Adult Reference BMI and Weight.
Actual dosage may adjust to patient.

Table 29 shows preferred ranges of vitamins, minerals and amino acids in the ingestible formulation.

TABLE 29

Composition Ranges of Daily Dosage of Vitamins, Minerals and Amino-Acids for the Ingestible Embodiment

| Ingredient | Min | | Max |
|---|---|---|---|
| Vitamin A | 0 | — | 4,000 IU |
| Vitamin C | 0 | — | 2,000 mg |
| Vitamin D | 0 | — | 5,000 IU |
| Vitamin K | 0 | — | 15 mg |
| Riboflavin | 0 | — | 400 mg |
| Niacin | 0 | — | 1,000 mg |
| Vitamin B6 | 0 | — | 3 mg |
| Folate | 0 | — | 750 mcg |
| Vitamin B12 | 0 | — | 1,000 mcg |
| Biotin | 0 | — | 5,000 mcg |
| Pantothenic acid | 0 | — | 10 mg |
| Iodine | 0 | — | 125 mcg |
| Zinc | 0 | — | 20 mg |
| Selenium | 0 | — | 70 mcg |
| Copper | 0 | — | 2,000 mg |
| Silica | 0 | — | 2,000 mcg |

TABLE 29-continued

Composition Ranges of Daily Dosage of Vitamins, Minerals and Amino-Acids for the Ingestible Embodiment

| Ingredient | Min | | Max |
|---|---|---|---|
| CoQ10 | 0 | — | 200 mg |
| L-Tyrosine | 0 | — | 5,000 mg |
| N-Acetyl Cysteine (NAC) | 0 | — | 6,000 mg |
| Astaxanthin | 0 | — | 12 mg |

Table 30 shows 7 the amount of vitamins, minerals, enzymes and amino acids used in 7 embodiments of the ingestible formulation.

TABLE 30

Preferred Composition of Daily Dosage of Vitamins, Minerals, Enzymes and Amino-Acids for the Ingestible Embodiment

| Formulation: | 1 ALRVXR-D00 | 2 ALRVXR-D02 | 3 ALRVXR-D06 | 4 ALRVXR-D08 | 5 ALRVXR-D10 | 6 ALRVXR-D12 | 7 ALRVXR-D14 |
|---|---|---|---|---|---|---|---|
| Vitamin A | 2,000 IU | 2,000 IU | 2,000 IU | 2,000 IU | 2,000 IU | 2,000 IU | 2,000 IU |
| Vitamin C | | 1,000 mg | 2,000 mg | 2,000 mg | 2,000 mg | 2,000 mg | 2000 mg |
| Vitamin D | 1,000 IU | 1,000 IU | 1,000 IU | 1,000 IU | 1,000 IU | 1,000 U | 1,000 IU |
| Vitamin K | | 3 mg | | | 10 mg | | 5 mg |
| Riboflavin | 1.3 mg | 1.3 mg | 1.3 mg | 1.3 mg | 1.3 mg | 1.3 mg | 1.3 mg |
| Niacin | 15 mg | 15 mg | 15 mg | 500 mg | 500 mg | 15 mg | 15 mg |
| Vitamin B6 | 1.7 mg | 1.7 mg | 1.7 mg | 1.7 mg | 1.7 mg | 1.7 mg | 1.7 mg |
| Folate | 400 mcg | 400 mcg | 400 mcg | 400 mcg | 400 mcg | 400 mcg | 400 mcg |
| Vitamin B12 | 20 mcg | 20 mcg | 20 mcg | 20 mcg | 20 mcg | 20 mcg | 20 mcg |
| Biotin | 500 mcg | 500 mcg | 500 mcg | 500 mcg | 500 mcg | 500 mcg | 500 mcg |
| Pantothenic acid | 5 mg | 5 mg | 5 mg | 5 mg | 5 mg | 5 mg | 5 mg |
| Iodine | 105 mcg | 105 mcg | 105 mcg | 105 mcg | 105 mcg | 105 mcg | 105 mcg |
| Zinc | 15 mg | 15 mg | 15 mg | 15 mg | 15 mg | 15 mg | 15 mg |
| Selenium | 36 mcg | 36 mcg | 36 mcg | 36 mcg | 36 mcg | 36 mcg | 36 mcg |
| Copper | 900 mcg | 900 mcg | 900 mcg | 900 mcg | 900 mcg | 900 mcg | 900 mcg |
| Silicon | 800 mcg | 1,000 mcg | 800 mcg | 800 mcg | 800 mcg | 800 mcg | 800 mcg |
| CoQ10 | 60 mg | 60 mg | 60 mg | 150 mg | 150 mg | 60 mg | 150 mg |
| L-Tyrosine | | 200 mg | | | | | 100 mg |
| N-Acetyl Cysteine | | 100 mg | | 100 mg | 100 mg | 100 mg | 100 mg |
| Astaxanthin | | 3 mg | | 3 mg | 3 mg | 3 mg | 10 mg |

Daily Dosage per Standard Adult Reference BMI and Weight
Dosages are pro-rated by weight of subject relative to the Standard

Example 21: Hair Loss Randomized Controlled Study in Women

This study investigated in a randomized clinical trial the effect of ALRV5XR against placebo (administered as oral supplement, shampoo, conditioner and topical serum) containing vitamins, minerals, and herbal extracts on scalp hair growth. ALRV5XR comprises various formulations of Formulation X used in the clinical trial: ALRVXR-500, ALRVXR-S0F, ALRVXR-S0M, ALRVXR-C00, ALRVXR-C0F, ALRVXR-C0M, ALRVXR-N00, ALRVXR-N0F, ALRVXR-N0M. ALRVXR-D00 is a formulation of Formulation X1.

Objectives

The purpose of this study was to evaluate the effects of ALRV5XR on parameters of hair growth in women with androgenetic alopecia, diffuse hair loss, or self-reported thinning hair over a 6-month period compared to placebo.

The primary objective was to determine the change in terminal (non-vellus) hair count from baseline to week 24, as number of hairs in the area being examined, as measured by macrophotography (trichometric analysis and validated computer-assisted techniques).

The safety of ALRV5XR was assessed by laboratory tests and the recording of adverse events.

Methods

Study Design

This was a prospective, 24-week, randomized, double-blind, placebo-controlled, 2-arm parallel study to evaluate the efficacy and safety of ALRV5XR on changes in total and terminal hair growth, compared to placebo, in healthy female adults with thinning hair.

Study Subjects

All subjects signed an institutional review board approved informed consent form before participation in the study.

Eligible subjects were healthy adult females, 18-65 years of age, who suffer from androgenetic alopecia, diffuse hair loss or self-reported thinning or hair loss for more than 3 months prior to screening, clinically confirmed by the investigator via physical exam. Women had to be in good general health, as determined by the Investigator with a Fitzpatrick skin type I-IV and willing to follow study requirements and procedures.

Reasons for exclusion from the study included clinical diagnosis of scarring forms of alopecia or alopecia areata, clinical diagnosis on the scalp of psoriasis, scaling, fungal or bacterial infection, lesions, follicular dermatitis, lice, fleas or chemical burns, unusual thinning patches, traction alopecia or trichokryptomania, trichthiodystrophy, pili annulati, monilethrix or clear signs of trichodysmorphia, poor nutrition or hygeine. Additional exclusion criteria included damage to the skin in or around the assessment areas, scalp hair loss on the treatment area due to disease, injury, or medical therapy, history of surgical correction of hair loss on the scalp, hair transplants or hair weave. Women were also not allowed to use or have used depilatories, razors, or wax on the scalp to an extent which, in the opinion of the investigator, may interfere with the performance of the study assessments. Subjects who were pregnant or planned to become pregnant or were breastfeeding during the course of the study or subjects who were unwilling to use appropriate contraceptives for the duration of the study, were also excluded. The presence of diseases such as diabetes, endocrine, cardiovascular, renal, or liver disease, a history of neurological disease (e.g., Parkinson's disease, stroke, traumatic brain injury, etc.) were also considered exclusion criteria. Women were also not allowed to have recently started (<6 months) using hormone replacement therapy, including hormonal birth control. Hypertension defined as a seated resting systolic blood pressure ≥140 mmHg and/or diastolic blood pressure ≥90 mmHg or current use of blood pressure lowering medications were also considered exclusion criteria. Women were also not allowed to use any medications (including natural health products) that are known to potentially cause hair loss or affect hair growth within 30 days prior to the baseline visit, as determined by the principal investigator. Subjects with a history of malignancy (in past 5 years) or undergoing chemotherapy or radiation treatments, or a known history of autoimmune disease (e.g., HIV/AIDS, systemic lupus erythematosus, inflammatory bowel disease, alopecia areata, alopecia totalis, etc.), uncontrolled thyroid disease, or any other disorders that in the opinion of the investigator may interfere with the study treatment, were also excluded. Evidence of hepatic or renal dysfunction, as determined by the principal investigator, were also considered exclusion criteria.

Test Materials

Subjects were randomized to receive either ALRV5XR or placebo. Test materials included for both groups oral formulations (capsules), shampoo, conditioner, and topical follicle serum. The treatment group received ALRV5XR provided by Arbor Life Labs, the placebo groups received similar looking and smelling products, containing the same base materials as the active treatment group products. Study ingredients included . . . .

Study Procedures

Subjects were randomized to receive either ALRV5XR or placebo. The duration of the study was approximately 28 weeks, including the screening period (eligibility assessment), followed by a baseline visit, a 12-week, and a 24-week experimentation period for assessment of treatment effects.

Dermatologist Assessment, Diagnosis and Hair Loss Pattern Classification

Subjects were clinically assessed by a dermatologist for eligibility, diagnosis of hair loss condition, and hair loss pattern classification. At weeks 12 and 24 patients were assessed for any changes in health, eligibility adverse events and compliance.

A 35-mm Nikon camera (Canfield Scientific) was used to take the macrophotographs at 0, 45, and 90 degrees of the frontal, mid-scalp, as well as of the head. The 2-D images were blindly assessed in addition to the dermatologist's physical assessment, to determine the hair loss diagnosis and the Ludwig (or Hamilton-Norwood) hair loss pattern classification.

Efficacy Evaluation

Target area hair counts (TAHC) were performed at baseline week 12, and week 24. At baseline, a circular area at the center of the hair-whorl on the vertex region of the scalp was chosen as the target area for hair counts. A permanent ink dot tattoo was placed for precise localization of the target area on subsequent evaluations. The hairs in the target area were clipped to less than 0.5 mm and then dyed. Mineral oil was applied to the target area. Phototrichoscopy images were taken of the target area at each visit using a Firefly DE330T Trichoscope with 2 MP resolution at 35× magnification and a 55.10 $mm^2$ field of view. A cover glass was fixed to the lens of the trichoscope to orient the hair shafts in the target area at 90 degrees to the lens.

Figure 10:
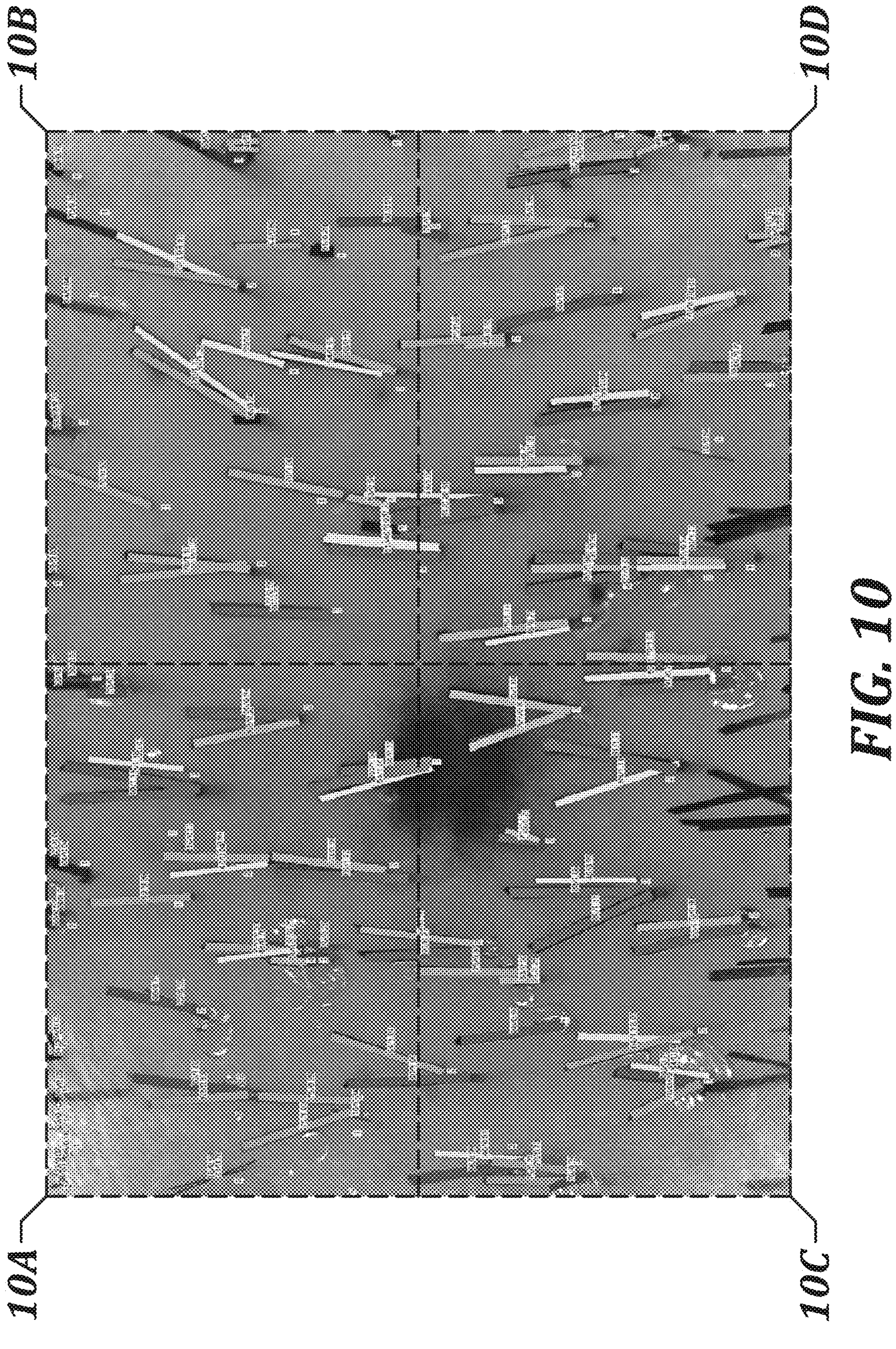
FIG. 10 is a an analyzed Phototricoscopy image used in studies of the invention.
Figure 10A:
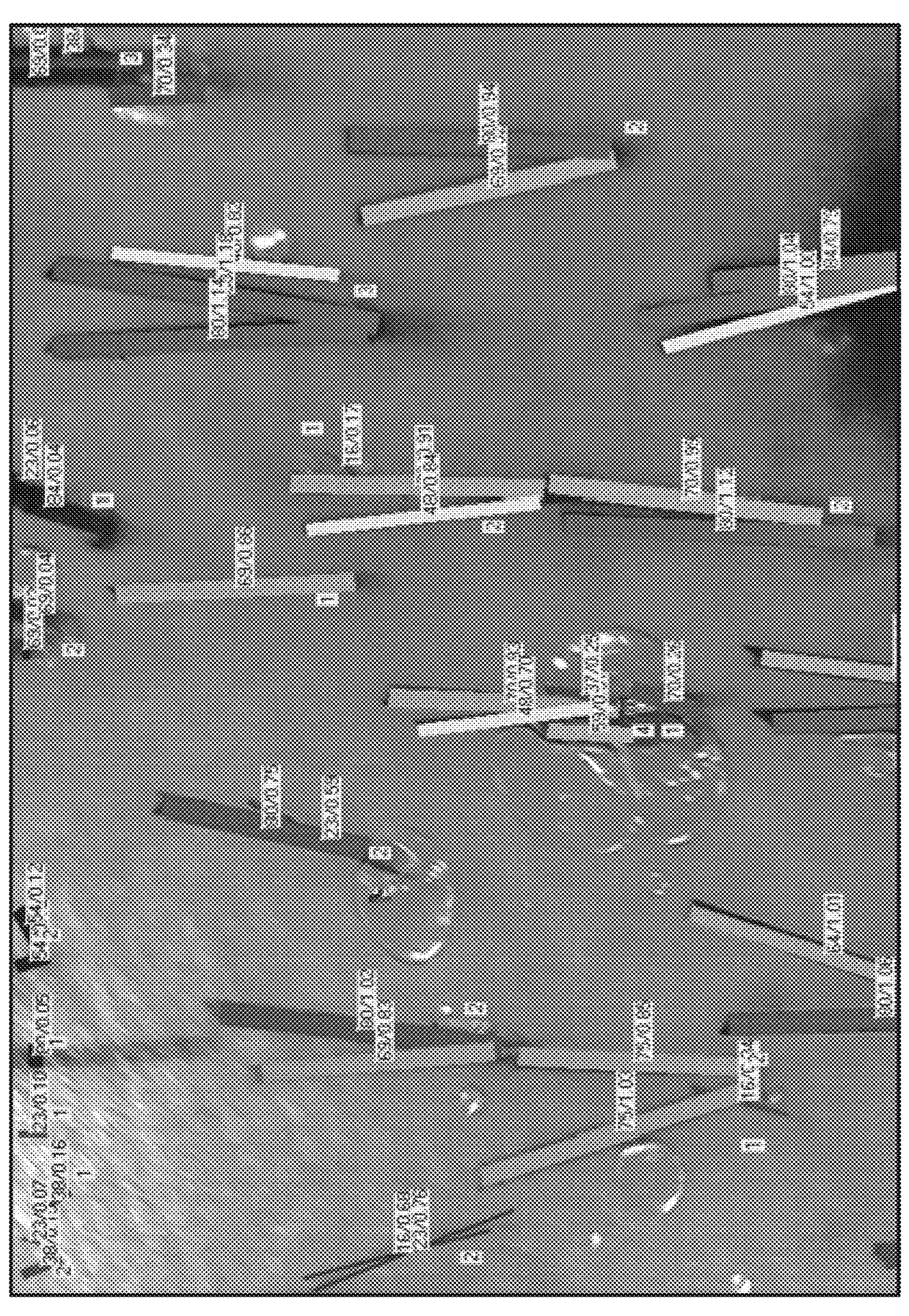
FIGS. 10A-10D are enlargements of the four quadrants of FIG. 10 with FIG. 10A the upper left quadrant of FIG. 10, FIG. 10B the upper right quadrant of FIG. 10, FIG. 10C the lower left quadrant of FIG. 10, and FIG. 10D the lower left quadrant of FIG. 10.
Figure 10B:
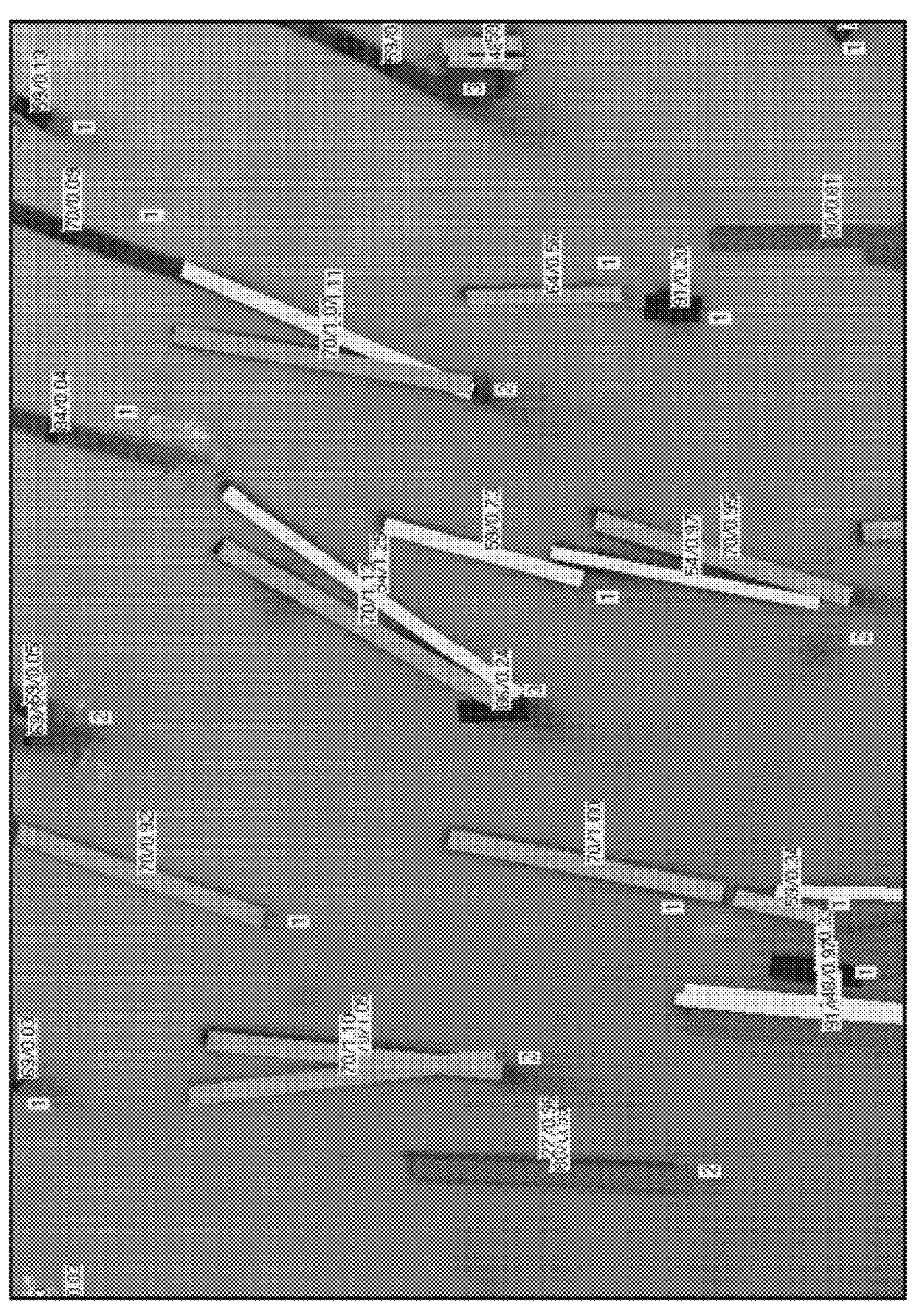
Figure 10C:
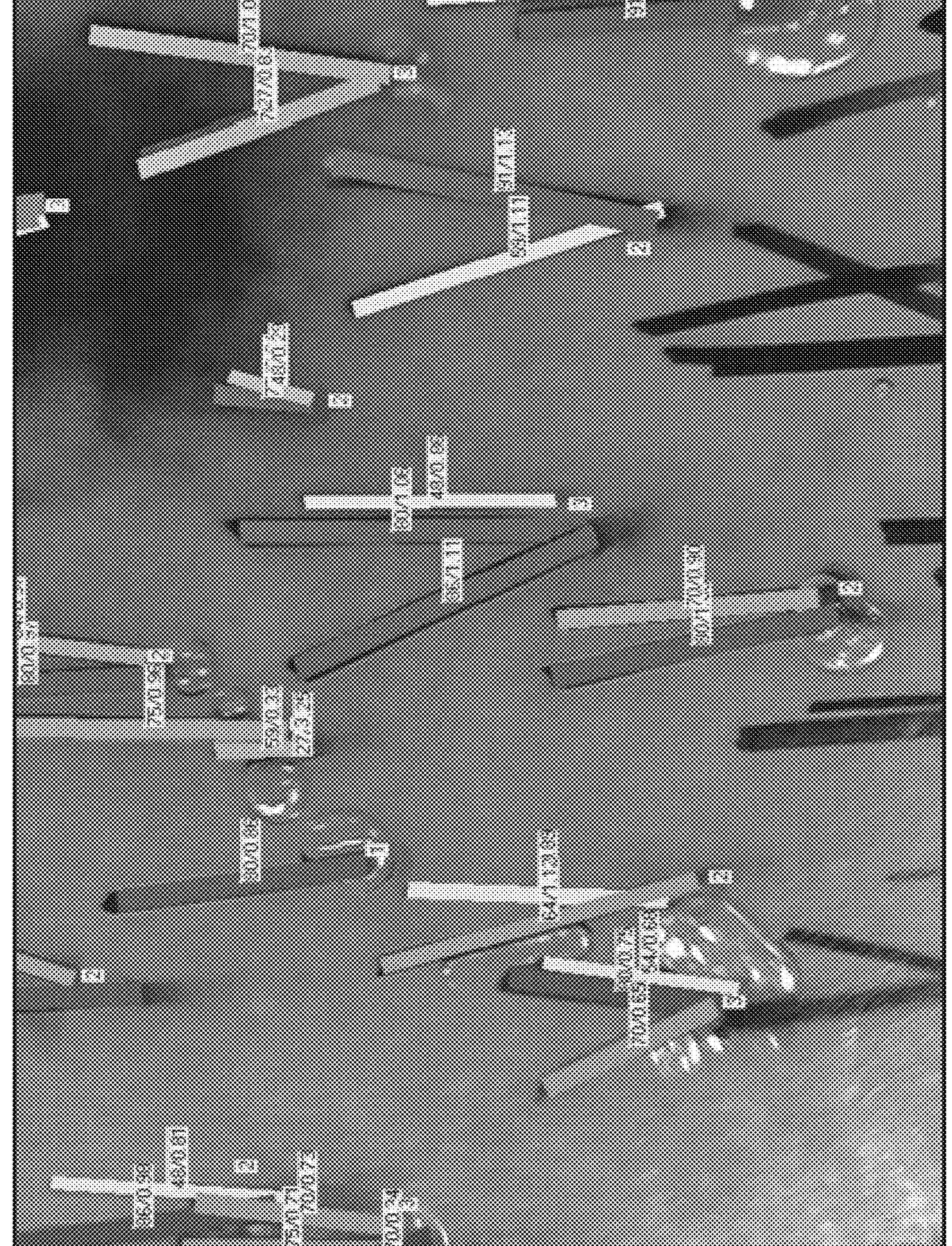
Figure 10D:
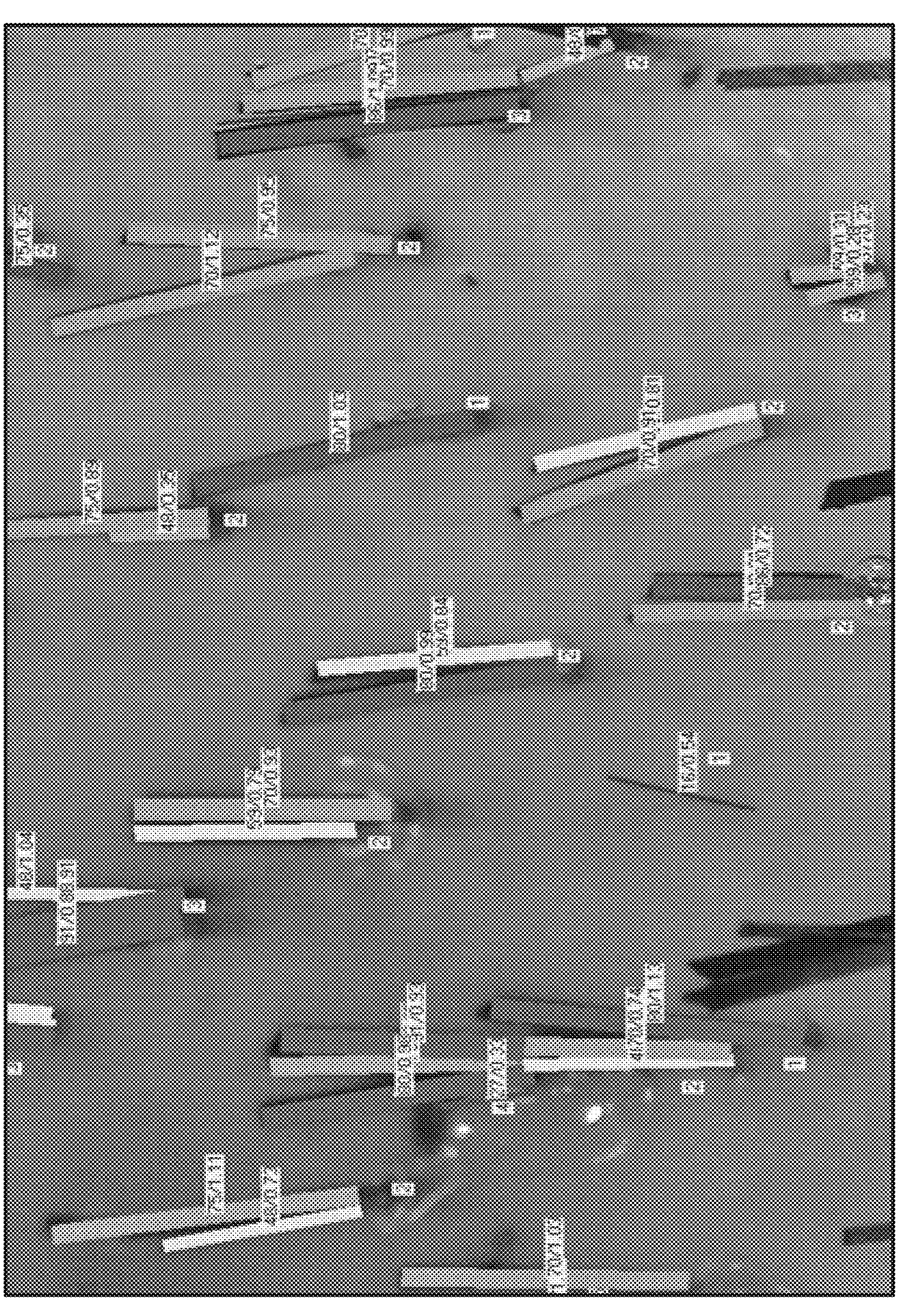

FIG. 10 shows an example of an analyzed Phototricoscopy image.

Phototrichoscopy images were analyzed by a blinded trichoanalyst, using the TrichosciencePro V1.5. Terminal (non-vellus) hair density was determined by counting hairs in the field of view, only when a hair was fully visible from its trimmed end to the exiting position of a scalp pore and then eliminating vellus hairs from the hair count. Terminal hairs were determined based on hair diameter greater than or equal to 40 μm. Digital images were initially automatically analyzed by computer to determine hair count and measure hair shaft diameter. This was repeated and compared using a semi-automatic and manual detection and measurement mode by a blinded trichoanalyst. Terminal hair density was calculated based on the number of hairs with hair diameter measuring greater than or equal to 40 μm per $cm^2$.

Results

A total of 46 women were enrolled in the study (23 subjects in each group). Five subjects (2 subjects in the placebo group and 3 subjects in the ALRV5XR group) withdrew consent at the baseline assessment and were excluded from any analysis. This became the Intent-To-Treat analysis group (ITT). At the end of the trial, 2 subjects in the ALRV5XR group were non-compliant with the treatment regimen and excluded from the hair analysis. This became the Per-Protocol analysis group (PP).

Baseline demographic and physical characteristics were similar between the groups (Table 31). Also, no differences were found in categorical variables (ethnicity, skin type and hair loss pattern) between treatment groups at baseline (Table 32).

There were some differences in baseline characteristics between treatment groups regarding trichoscopy characteristics. However, they were deemed not clinically relevant and were not expected to affect study outcomes, as the balance of the differences did not favor either group.

No Adverse events were reported and all labs were normal.

Difference in Terminal Hair count between the ALRV5XR group and the Placebo group at 6 months was 30.1 hairs per sq·cm and was highly statistically significant (p=0.0003).

Difference in Terminal Hair count between the ALRV5XR group and the Placebo group at 3 months was 12.9 hairs per sq·cm and was highly statistically significant (p=0.0029).

Additional data collected allowed for evaluation of Changes in Follicular Unit (FU). A FU is a cluster of 1 to 5 hair follicles that share a common sebaceous gland and erector pili muscle and exit the scalp through a common pore. Although Terminal Hair is reported as the primary endpoint, the number of FU's in the target area were also counted. The significant change in FU's was unexpected and upon further evaluation was a primary contributor to change in terminal hair count, which was also significantly greater than anticipated.

Difference in Follicular Unit (FU) count between the ALRV5XR group and the Placebo group at 6 months was 13.0 FU's per sq·cm and was highly statistically significant (p=0.0029).

Difference in Follicular Unit (FU) count between the ALRV5XR group and the Placebo group at 3 months was 6.5.0 FU's per sq·cm and was highly statistically significant (p=0.0031).

TABLE 31

| Baseline demographics and physical characteristics by treatment group, continuous variables (ITT) | | | | | | | | | | |
|---|---|---|---|---|---|---|---|---|---|---|
| | Variable | | | | | | | | | |
| Name | TRT | Visit | N | Mean | SD | TRT | N | Mean | SD | p value |
| Age | A | 0 | 21 | 51.86 | 10.53 | B | 20 | 50.1 | 9.12 | 0.6474 |
| Height | A | 0 | 21 | 159.1 | 4.63 | B | 20 | 160.9 | 8.2 | 0.398 |
| Weight | A | 0 | 21 | 76.53 | 29.85 | B | 20 | 66.94 | 17.01 | 0.3081 |
| Temperature | A | 0 | 21 | 97.8 | 0.32 | B | 20 | 97.77 | 0.66 | 0.8336 |
| Heart Rate | A | 0 | 21 | 71.86 | 7.6 | B | 20 | 67.25 | 9.41 | 0.0917 |
| Resp Rate | A | 0 | 21 | 15.86 | 2.31 | B | 20 | 15.5 | 2.14 | 0.6108 |
| BP left arm systolic | A | 0 | 21 | 118.67 | 11.47 | B | 19 | 120.63 | 8.71 | 0.5487 |
| BP left arm diastolic | A | 0 | 21 | 75.05 | 5.85 | B | 19 | 76.68 | 8.33 | 0.4817 |
| BP right arm systolic | A | 0 | 20 | 115.8 | 13.76 | B | 19 | 117.84 | 10.07 | 0.6018 |
| BP right arm diastolic | A | 0 | 20 | 74.55 | 6.89 | B | 19 | 76.95 | 6.76 | 0.28 |

Treatment group A = placebo, Treatment group B = ALRV5XR,
Abbreviations: SD = Standard Deviation

TABLE 32

| Categorical Physical Characteristics at Baseline. (ITT) | | | |
|---|---|---|---|
| | Treatment | | |
| Ethnicity | A | B | p-value = 0.8181 |
| Caucasian | 3 | 1 | |
| Chinese | 12 | 13 | |
| Hispanic | 4 | 3 | |
| Japanese | 2 | 1 | |
| Mongolian | 0 | 1 | |
| Philipino | 0 | 1 | |
| Skin Type | A | B | p-value = 0.6642 |
| 1 | 3 | 4 | |
| 2 | 8 | 8 | |
| 3 | 7 | 8 | |
| 4 | 2 | 0 | |
| 6 | 1 | 0 | |
| Diagnosis | A | B | p-value = 0.09995 |
| AA | 11 | 16 | |
| TE | 10 | 4 | |
| Ludwig Class | A | B | p-value = 0.2184 |
| I | 17 | 19 | |
| II | 0 | 1 | |
| Missing | 4 | 0 | |
| Ludwig Type | A | B | p-value = 0.4288 |
| 1 | 3 | 2 | |
| 2 | 4 | 12 | |
| 3 | 9 | 5 | |
| 4 | 1 | 1 | |

Treatment group A = placebo, Treatment group B = ALRV5XR Abbreviations:

Table 33 describes the Terminal hairs per square centimeter (sq cm) stratified per visit.

TABLE 33

| Comparison of Trichoscopy Summary Statistics by Visit for Terminal Hair Counts per sq.cm. (PP) "Terminal.hairs.per.sq.cm." | | | | | | | | | |
|---|---|---|---|---|---|---|---|---|---|
| TRT | Visit | N | Mean | SD | TRT | N | Mean | SD | p value |
| A | 0 | 21 | 141.2 | 33.26 | B | 18 | 148.74 | 31.09 | 0.4699 |
| A | 3 | 21 | 144.35 | 32.26 | B | 18 | 161.11 | 38.29 | |
| A | 6 | 21 | 145.45 | 33.76 | B | 18 | 176.32 | 48.15 | |

Treatment group A = placebo, Treatment group B = ALRV5XR
Abbreviations: TRT = Treatment Group;
Visit: 0 = Baseline, 3 = 3 Months, 6 = 6 Months;
N = sample size;
SD = Standard Deviation;
p value = T-Test where <0.05 is statistically significant and <0.01 is highly statistically significant.

In regard to trichoscopy changes, the active treatment group (group B) had a significantly higher mean increase in Terminal hairs per sq cm from baseline to 3 months (Table 34). The same was observed at 6 months (Table 35).

TABLE 34

| Increase in Terminal Hairs (per sq cm) at 3 and 6 Months (PP) "Increase in Terminal.hairs.per.sq.cm." | | | | | | | | | |
|---|---|---|---|---|---|---|---|---|---|
| TRT | Visit | N | Mean | SD | TRT | N | Mean | SD | p value |
| A | 3-0 | 21 | 3.14 | 7.49 | B | 18 | 16.06 | 16.62 | 0.0029 |
| A | 6-0 | 21 | 3.86 | 15.74 | B | 18 | 33.94 | 29.37 | 0.0003 |

Treatment group A = placebo, Treatment group B = ALRV5XR
Abbreviations: TRT = Treatment Group;
Visit: 0 = Baseline, 3 = 3 Months, 6 = 6 Months, 3-0 = Baseline to 3 Months, 6-0 = Baseline to 6 Months;
N = sample size;
SD = Standard Deviation;
p value = T-Test where <0.05 is statistically significant and <0.01 is highly statistically significant.

TABLE 35a

Comparison of Trichoscopy Summary Statistics by Visit for Follicular Unit Counts per sq.cm. (ITT) "Follicular Units.per.sq.cm."

| TRT | Visit | N | Mean | SD | TRT | N | Mean | SD | p value |
|---|---|---|---|---|---|---|---|---|---|
| A | 0 | 21 | 105.5 | 18.9 | B | 20 | 99.5 | 24.48 | 0.3802 |
| A | 3 | 21 | 106.2 | 18.19 | B | 20 | 106.3 | 25.06 | |
| A | 6 | 21 | 107.0 | 17.69 | B | 20 | 112.4 | 29.73 | |

Treatment group A = placebo, Treatment group B = ALRV5XR
Abbreviations: TRT = Treatment Group;
Visit: 0 = Baseline, 3 = 3 Months, 6 = 6 Months, 3-0 = Baseline to 3 Months, 6-0 = Baseline to 6 Months;
N = sample size;
SD = Standard Deviation;
p value = T-Test where <0.05 is statistically significant and <0.01 is highly statistically significant.

In regard to follicular unit changes, the active treatment group (group B) had a significantly higher mean increase in follicular units hairs per sq cm from baseline to 3 months (Table 35a). The same was observed at 6 months (Table 35b).

TABLE 35b

Increase in Follicular Units (per sq cm) at 3 and 6 Months (PP) Increase in Follicular Units (per sq cm)

| TRT | Visit | N | Mean | SD | TRT | N | Mean | SD | p value |
|---|---|---|---|---|---|---|---|---|---|
| A | 3-0 | 21 | 0.69 | 4.26 | B | 18 | 7.16 | 8.28 | 0.0031 |
| A | 6-0 | 21 | 1.53 | 6.53 | B | 18 | 14.52 | 16.96 | 0.0029 |

Treatment group A = placebo, Treatment group B = ALRV5XR
Abbreviations: TRT = Treatment Group;
Visit: 0 = Baseline, 3 = 3Months, 6 = 6 Months, 3-0 = Baseline to 3 Months, 6-0 = Baseline to 6 Months;
N = sample size;
SD = Standard Deviation;
p value = T-Test where <0.05 is statistically significant and <0.01 is highly statistically significant.

Conclusions

ALRV5XR significantly addresses an unmet need for an effective (and safe) treatment option for androgenetic alopecia and telogen effluvium in women by targeting multiple pathways associated with promoting normal hair growth and inhibiting hair loss. ALRV5XR was shown to be an effective, safe and well tolerated treatment option for women with androgentic alopecia or telogen effluvium in increasing the terminal hair count from baseline to week 12 with event greater increases to week 24. There was no difference found in the result across all ages, ethnicities, skin types and balding patterns ALRV5XR was also found to increase the number of follicular units and to be safe and effective.

Example 22: Hair Loss Randomized Controlled Study in Men

This study investigated in a randomized clinical trial the effect of ALRV5XR (administered as oral supplement, shampoo, conditioner and topical serum) containing vitamins, minerals, and herbal extracts on scalp hair growth.

This study objectives, methods, design and materials were identical to the study in Example 22, with the exception of eligibility being for men and elimination of other female specific criteria, such as pregnancy and breastfeeding.

Results

A total of 46 men were enrolled in the study (23 subjects in each group). Nine subjects (4 subjects in the placebo group (A) and 6 subjects in the ALRV5XR group (B)) withdrew consent at the baseline assessment and were excluded from any analysis. This became the Intent-To-Treat analysis group (TIT) and were used in the demographic and lab analysis. 4 subjects were eliminated from the hair analysis due to operator error with the trichoscopies (2 in each group). Subjects were eliminated from hair change calculations at month 12 weeks (3 months/visit 2) or 24 weeks (6 months/48 weeks) due to operator error with trichoscopies resulting in 14 (baseline visit), 11 (visit 2) and 11 (visit 3) subjects in the placebo group and 13 (baseline), 11 (visit 2) and 11 (visit 3) in the ALRV5XR group. As a result of the pair-wise trichoscopy analysis to determine the changes in each group, there were 11 subjects at each visit in each group used in trichoanalysis. These subjects formed the Per-Protocol group (PP) for trichometric analysis.

Baseline demographic and physical characteristics were similar between the groups (Table 36). Also, no differences were found in categorical variables (ethnicity, skin type and hair loss pattern) between treatment groups at baseline (Table 37).

At month 3, Group B had borderline significantly higher left arm diastolic BP (p=0.0418) however the mean is very similar to baseline values and borderline significance disappears at month 6. This is not a good measure for differences between groups since it is not looking at changes over time. Similarly, with right arm systolic BP (0.0318) however again month 3 mean is very similar to baseline and the significance disappears at month 6. There were no significant physical changes over time (see Table 36).

There were no differences in baseline characteristics between treatment groups regarding trichoscopy characteristics.

No Adverse events were reported, and all labs were normal.

Difference in Terminal Hair count between the ALRV5XR group and the Placebo group at 6 months was 21.0 hairs per sq·cm and was highly statistically significant (p=0.0016).

Difference in Terminal Hair count between the ALRV5XR group and the Placebo group at 3 months was 13.0 hairs per sq·cm and was highly statistically significant (p=0.0020).

TABLE 36

Baseline demographics and physical characteristics by treatment group, continuous variables (ITT)

| Variable name | TRT | Visit | N | MEAN | SD | TRT | N | MEAN | SD | P Value |
|---|---|---|---|---|---|---|---|---|---|---|
| Age | A | 0 | 18 | 46.56 | 11.51 | B | 17 | 48.24 | 8.80 | 0.5788 |
| Height | A | 0 | 19 | 177.65 | 11.19 | B | 17 | 174.15 | 9.43 | 0.3205 |
| Weight | A | 0 | 19 | 85.81 | 24.76 | B | 17 | 89.56 | 16.52 | 0.6013 |
| Weight | A | 3 | 19 | 85.54 | 23.93 | B | 17 | 89.29 | 16.6 | 0.5931 |
| Weight | A | 6 | 19 | 85.38 | 23.51 | B | 17 | 88.82 | 14.72 | 0.6070 |
| Temperature | A | 0 | 19 | 97.33 | 0.79 | B | 17 | 97.15 | 0.55 | 0.4386 |
| Temperature | A | 3 | 19 | 97.65 | 0.77 | B | 17 | 97.72 | 0.85 | 0.7960 |

TABLE 36-continued

Baseline demographics and physical characteristics by treatment group, continuous variables (ITT)

| Variable name | TRT | Visit | N | MEAN | SD | TRT | N | MEAN | SD | P Value |
|---|---|---|---|---|---|---|---|---|---|---|
| Temperature | A | 6 | 19 | 97.79 | 0.65 | B | 17 | 97.80 | 0.58 | 0.9596 |
| Resp Rate | A | 0 | 19 | 15.37 | 1.42 | B | 17 | 16.24 | 2.95 | 0.7880 |
| Resp Rate | A | 3 | 19 | 15.63 | 1.61 | B | 17 | 15.88 | 2.47 | 0.4636 |
| Resp Rate | A | 6 | 19 | 16.37 | 2.52 | B | 16 | 15.94 | 1.39 | 0.2255 |
| Heart Rate | A | 0 | 19 | 75.32 | 10.9 | B | 17 | 76.47 | 14.57 | 0.2817 |
| Heart Rate | A | 3 | 19 | 78.74 | 12.97 | B | 17 | 75.76 | 10.83 | 0.7175 |
| Heart Rate | A | 6 | 19 | 82.58 | 12.85 | B | 16 | 77.69 | 10.08 | 0.5280 |
| BP left arm systolic | A | 0 | 19 | 127.32 | 13.26 | B | 17 | 132.53 | 23.45 | 0.4266 |
| BP left arm systolic | A | 3 | 19 | 126.95 | 16.76 | B | 17 | 136.76 | 17.2 | 0.0921 |
| BP left arm systolic | A | 6 | 19 | 125.11 | 16.4 | B | 17 | 132.00 | 21.32 | 0.2816 |
| BP left arm diastolic | A | 0 | 19 | 86.26 | 8.94 | B | 17 | 87.41 | 20.63 | 0.8338 |
| BP left arm diastolic | A | 3 | 19 | 81.68 | 12.28 | B | 17 | 91.18 | 15.46 | 0.0481 |
| BP left arm diastolic | A | 6 | 19 | 77.16 | 20.23 | B | 17 | 85.18 | 20.63 | 0.9293 |
| BP right arm systolic | A | 0 | 18 | 131.39 | 17.64 | B | 17 | 131.76 | 22.36 | 0.2273 |
| BP right arm systolic | A | 3 | 19 | 124.11 | 15.43 | B | 17 | 131.06 | 18.6 | 0.0318 |
| BP right arm systolic | A | 6 | 18 | 126.67 | 15.97 | B | 16 | 130.81 | 18.96 | 0.6947 |
| BP right arm diastolic | A | 0 | 18 | 83.39 | 11.97 | B | 17 | 87.65 | 18.13 | 0.2559 |
| BP right arm diastolic | A | 3 | 19 | 83.95 | 9.16 | B | 17 | 89.53 | 10.71 | 0.2551 |
| BP right arm diastolic | A | 6 | 18 | 79.89 | 11.13 | B | 16 | 83.00 | 19.26 | 0.9557 |

Treatment group A = placebo, Treatment group B = ALRV5XR
Abbreviations: TRT = Treatment Group;
Visit: 0 = Baseline, 3 = 3 Months, 6 = 6 Months;
N = sample size;
SD = Standard Deviation;
P value = T-Test where <0.05 is statistically significant and <0.01 is highly statistically significant.

TABLE 37

Categorical Physical Characteristics at Baseline. (ITT)

| | Treatment | | |
|---|---|---|---|
| Ethnicity | A (N) | B (N) | p-value = 0.916 |
| African American | 3 | 2 | |
| Caucasian | 6 | 5 | |
| Chinese | 4 | 5 | |
| Other | 4 | 5 | |
| Skin Type | A (N) | B (N) | p-value = 0.6407 |
| 1 | 1 | 0 | |
| 2 | 2 | 1 | |
| 3 | 9 | 13 | |
| 4 | 2 | 1 | |
| 5 | 1 | 0 | |
| 6 | 2 | 2 | |
| Hamilton-Norwood | A(N) | B(N) | p-value = 0.4418 |
| I MPB | 3 | 0 | |
| II MPB | 2 | 1 | |
| IIA MPB | 2 | 1 | |
| III MPB | 1 | 0 | |
| IIIA MPB | 0 | 1 | |
| IIIV MPB | 4 | 3 | |
| IIIV MPB/TE | 0 | 1 | |
| IV MPB | 1 | 4 | |
| V MPB | 0 | 1 | |
| VA MPB | 3 | 2 | |
| VII MPB | 1 | 3 | |

Abbreviations:
TRT = Treatment Group;
Visit: 0 = Baseline,
3 = 3 Months,
6 = 6 Months;
N = sample size;
SD = Standard Deviation;
p value = T-Test where <0.05 is statistically significant and <0.01 is highly statistically significant.

Table 38 describes the Terminal hairs per square centimeter (sq cm) stratified per visit.

TABLE 38

Comparison of Trichoscopy Summary Statistics by Visit for Terminal Hair Counts per sq.cm. (PP) "Terminal.hairs.per.sq.cm."

| TRT | Visit | N | Mean | SD | TRT | N | Mean | SD | p value |
|---|---|---|---|---|---|---|---|---|---|
| A | 0 | 15 | 148.67 | 69.53 | B | 13 | 140.31 | 74.23 | 0.7609 |
| A | 3 | 11 | 130.09 | 61.92 | B | 11 | 143.36 | 78.82 | |
| A | 6 | 11 | 144.45 | 74.87 | B | 11 | 156 | 88.57 | |

Treatment group A = placebo, Treatment group B = ALRV5XR
Abbreviations: TRT = Treatment Group;
Visit: 0 = Baseline, 3 = 3 Months, 6 = 6 Months;
N = sample size;
SD = Standard Deviation;
p value = T-Test where <0.05 is statistically significant and <0.01 is highly statistically significant.

In regard to trichoscopy changes, the active treatment group (group B) had a significantly higher mean increase in Terminal hairs per sq cm from baseline to 3 months (Table 38). The same was observed at 6 months (Table 39).

TABLE 39

Increase in Terminal Hairs (per sq cm) at 3 and 6 Months (PP) "Increase in Terminal.hairs.per.sq.cm."

| TRT | Visit | N | Mean | SD | TRT | N | Mean | SD | p value |
|---|---|---|---|---|---|---|---|---|---|
| A | 3-0 | 11 | −5 | 10.27 | B | 11 | 8 | 8.35 | 0.0020 |
| A | 6-0 | 11 | −5.82 | 5.46 | B | 11 | 15.18 | 18.02 | 0.0016 |

Treatment group A = placebo, Treatment group B = ALRV5XR
Abbreviations: TRT = Treatment Group;
Visit: 0 = Baseline, 3 = 3 Months, 6 = 6 Months, 3-0 = Baseline to 3 Months, 6-0 = Baseline to 6 Months;
N = sample size;
SD = Standard Deviation;
p value = T-Test where <0.05 is statistically significant and <0.01 is highly statistically significant.

Figure 11:
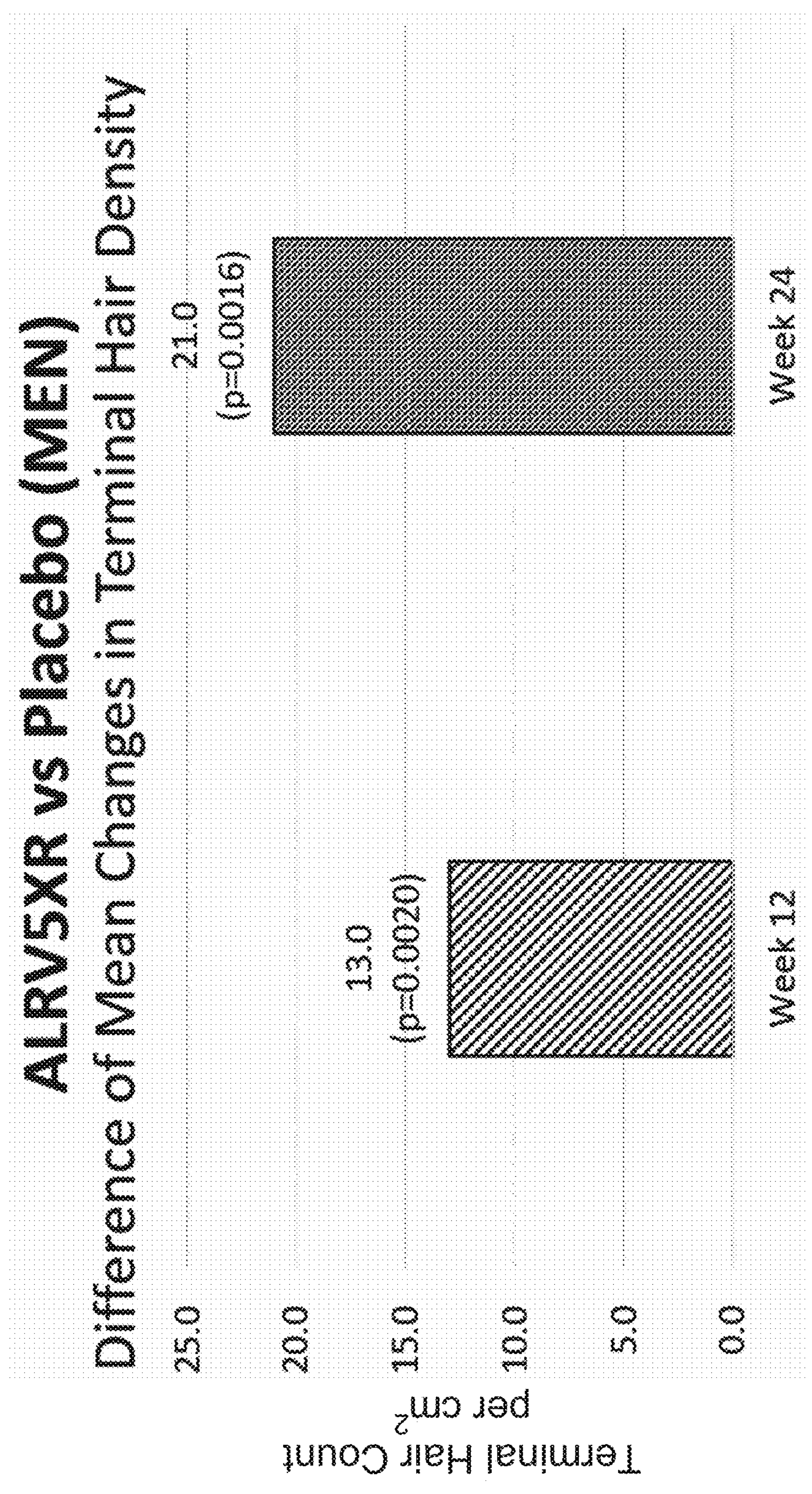
FIG. 11 is a graph showing differences in mean hair density using the present invention in men.
Figure 12:
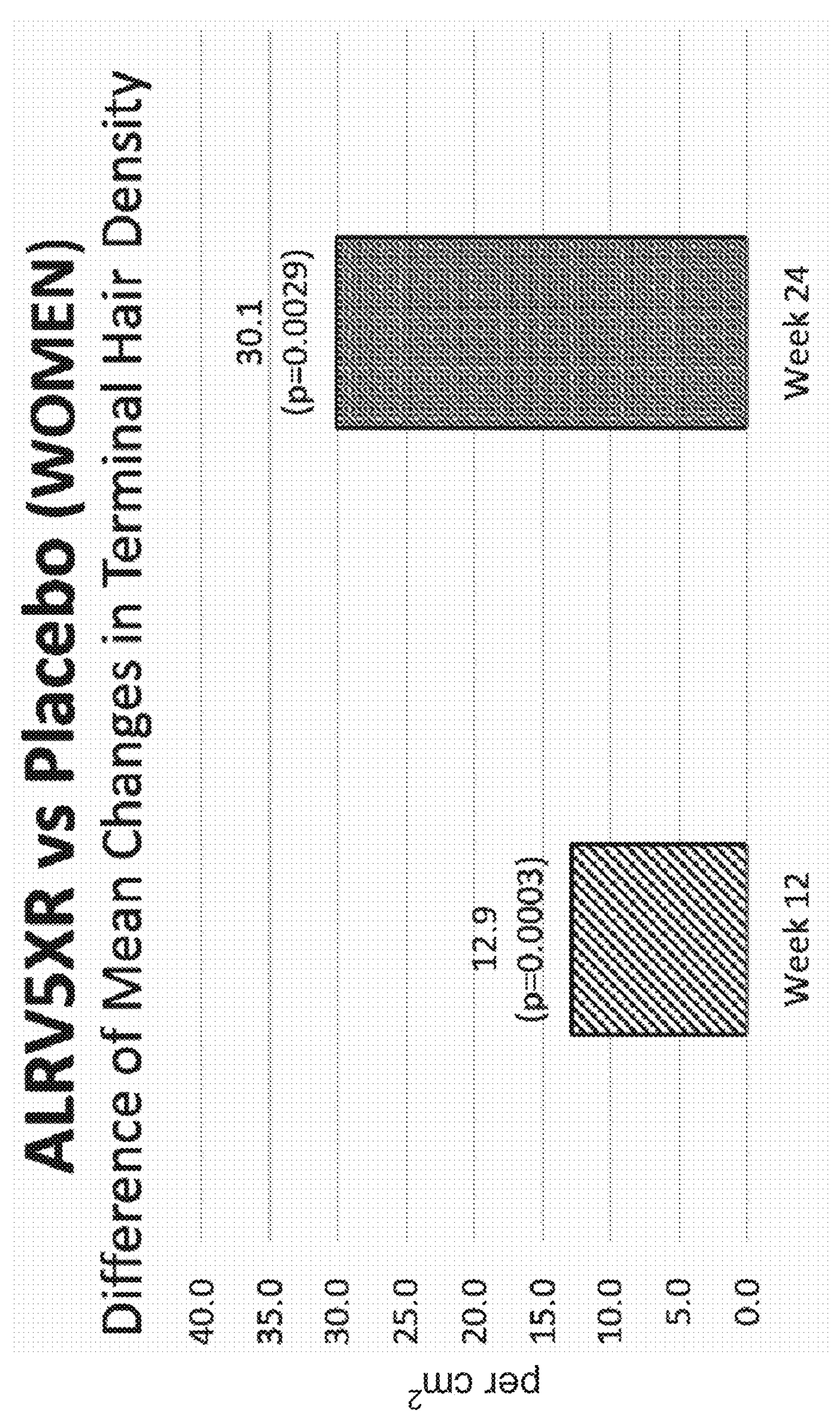
FIG. 12 is a graph showing differences in mean hair density using the present invention in women.
Figure 13:
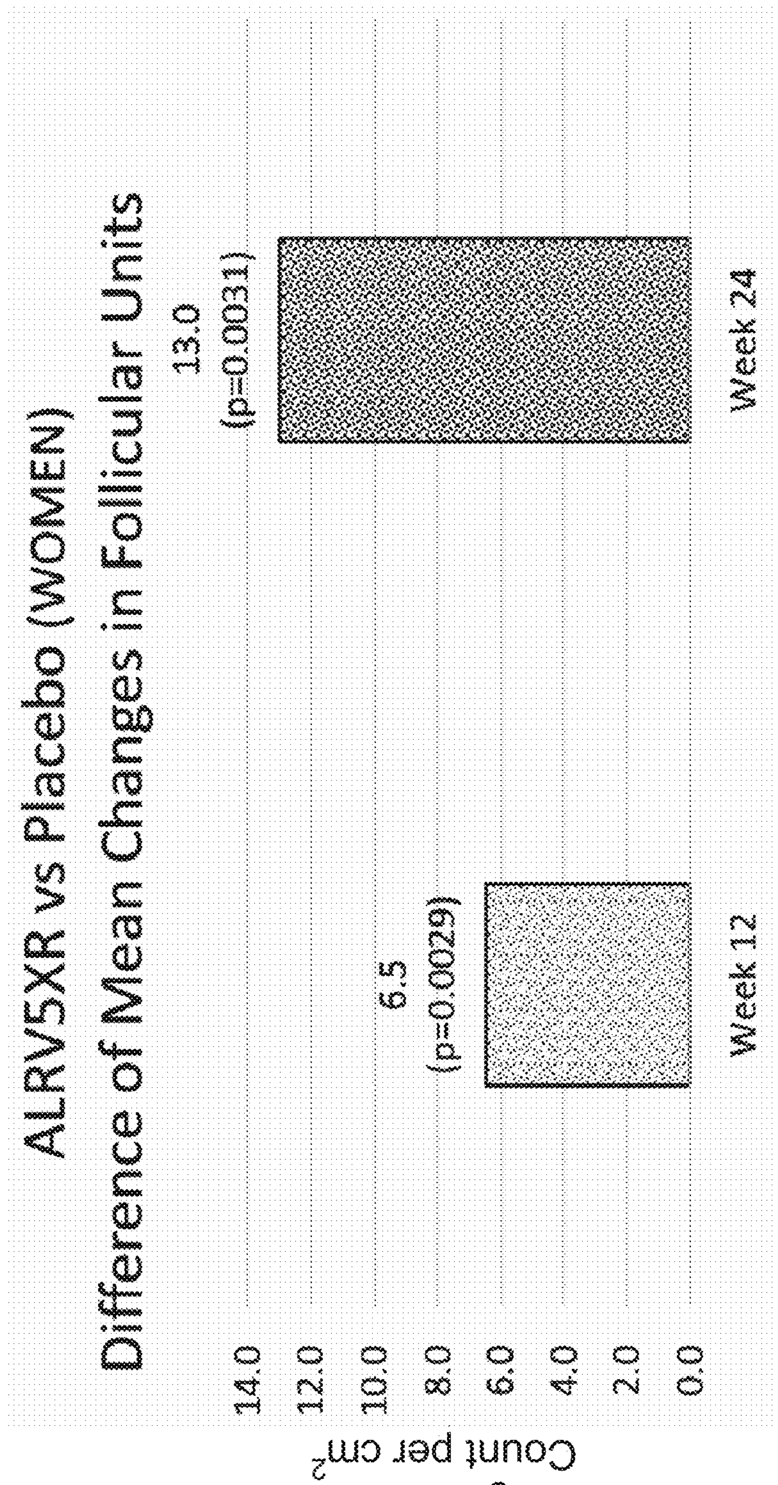
FIG. 13 is a graph showing differences in Follicular Units using the present invention in women.

FIG. 11 shows changes in hair density for men after using the present invention.

Conclusions

ALRV5XR significantly addresses an unmet need for an effective (and safe) treatment option for androgenetic alopecia and telogen effluvium in men by targeting multiple pathways associated with promoting normal hair growth and inhibiting hair loss. ALRV5XR was shown to be an effective, safe and well tolerated treatment option for male adults with androgentic alopecia or telogen effluvium in increasing the terminal hair count from baseline to week 12 with even greater increases to week 24. There was no difference found in the result across all ages, ethnicities, skin types and balding patterns.

Example 23: Comparison of Clinical Trial Results in Men to Standard of Care, Other Botanical Therapies and Emerging Treatments A comparative analysis of systematic reviews of randomized controlled clinical trials contributing to the standard of care in the treatment of androgenetic alopecia and telogen effluvium in Men, adjusted to 24 weeks of treatment showed that the invention in this disclosure using botanical formulation ALRV5XR in Men exceeds efficacy by a factor of 3.3 versus the standard of care in Men, i.e., topical 2% minoxidil and Finasteride 1 mg. Changes in Terminal hair count per sq·cm for ALRV5XR versus placebo at 6 months was 21.0 versus 6.4 for both 2% minoxidil and finasteride 1 mg. This is summarized in Table 40 below.

TABLE 40

ALRV5XR vs Comparator Therapeutics in Men
Comparison of Changes in Terminal Hair per sq.cm as Primary endpoint from clinical trials in Men, adjusted to 24 weeks, as between and placebo groups.

| Product | Terminal Hairs per sq.cm | Efficacy Factor Multiple vs 2% Minoxidil | Clinical Trial or Systematic Review |
|---|---|---|---|
| Nutrafol | N/A | N/A | N/A |
| Replicel | N/A | N/A | RepliCel-Phase 1 Poster |
| Samumed | 4.7 | 0.7 | Samumed-Phase 2 Poster Yazici |
| Viviscal | 6.4 | 1.0 | Viviscal-Men, Ablon, 2016 |
| Finasteride 1 mg | 6.4 | 1.0 | Finasteride 1 mg-Men, Godwin et al., 2017 |
| 2% Minoxidil | 6.4 | 1.0 | 2% Minoxidil-Men, Godwin et al., 2017 |
| 5% Minoxidil | 11.9 | 1.9 | 5% Minoxidil-Men, Godwin et al., 2017 |
| ALRV5XR | 21.0 | 3.3 | ALRV5XR (Men), 2019 |

Figure 15:
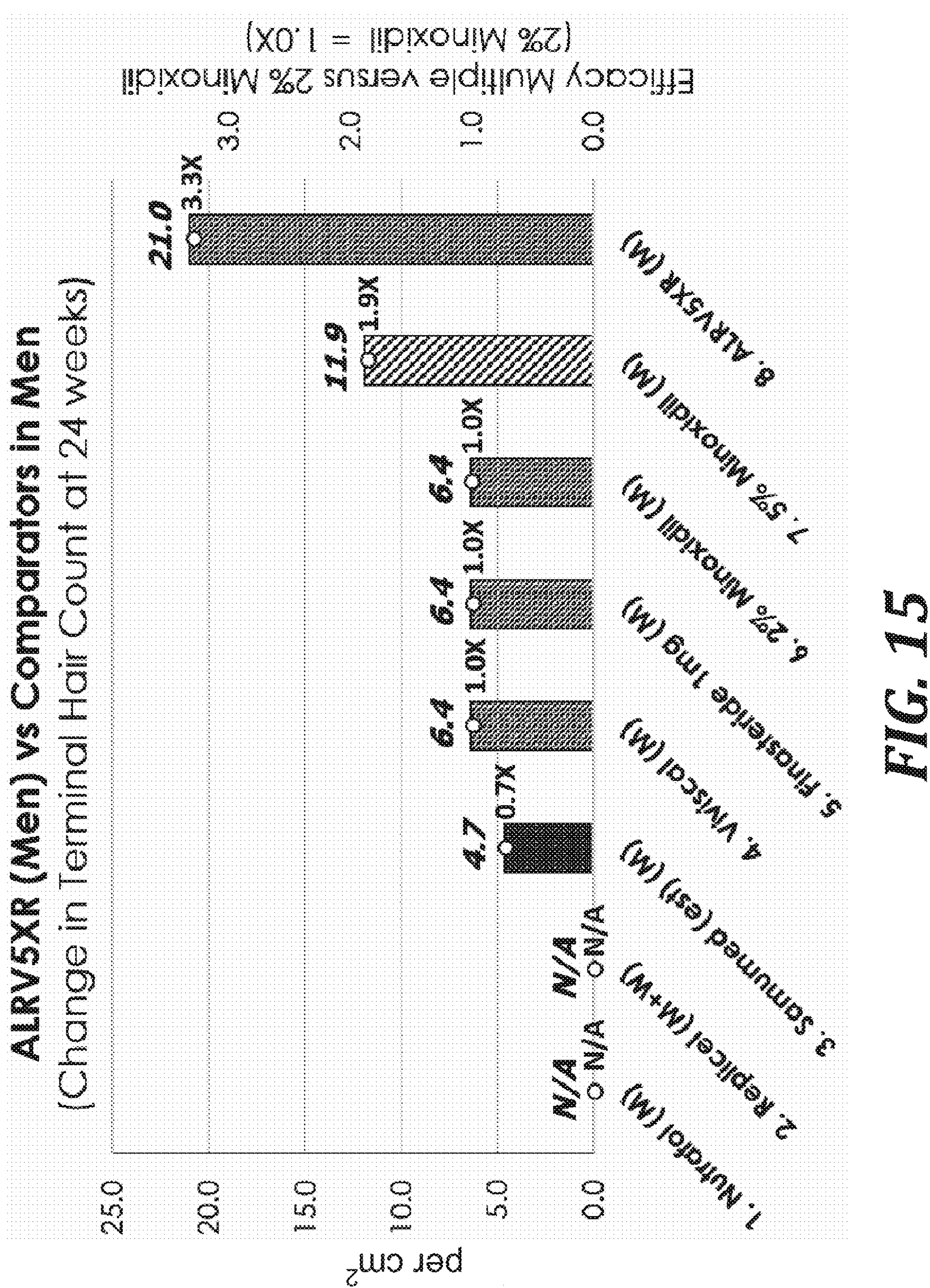
FIG. 15 is a bar chart comparing the present invention to the standard of care in men.
Figure 16:
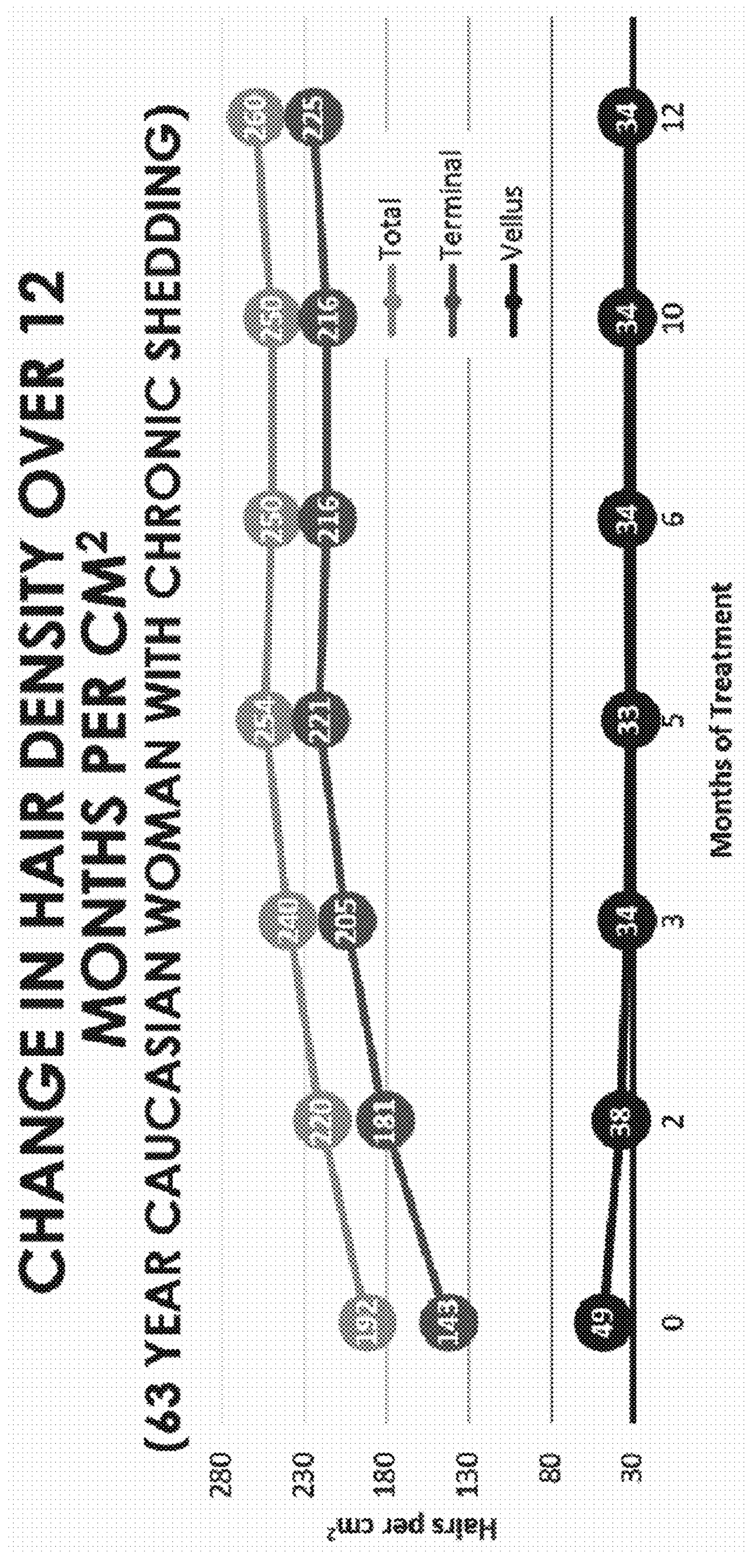
FIG. 16 is a graph showing change in hair density using the present invention.

FIG. 15 is a bar chart comparing the present invention to the standard of care in Men. As can be seen, the present invention shows superior results.

Example 24: Comparison of Clinical Trial Results to Standard of Care, Other Botanical Therapies and Emerging Treatments An comparative analysis of systematic reviews of randomized controlled clinical trials contributing to the standard of care in the treatment of androgentic alopecia and telogen effluvium in Women, adjusted to 24 weeks of treatment showed that the invention in this disclosure using botanical formulation ALRV5XR exceeds efficacy by a factor of 4.1 versus the standard of care in women, i.e. topical minoxidil 2%. Changes in Terminal hair count per sq·cm for ALRV5XR versus placebo at 6 months was 30.1 versus 7.3 for 2% minoxidil, 7.6 for 5% minoxidil. This is summarized in Table 41 below.

ALRV5XR vs Comparator Therapeutics in Women
Comparison of Changes in Terminal Hair per sq.cm as Primary endpoint from clinical trials in Women, adjusted to 24 weeks, as difference between active and placebo groups.

| Product | Terminal Hairs per sq.cm | Efficacy Factor Multiple vs 2% Minoxidil | Clinical Trial or Systematic Review |
|---|---|---|---|
| Viviscal | N/A | N/A | Viviscal-No Comparable Study in Women |
| Replicel | N/A | N/A | RepliCel-Phase 1 Poster (Men & Women), McElwee et al., 2013 (Insufficient Data) |
| Samumed | N/A | N/A | Samumed-No Comparable Study in Women |
| Finasteride 1 mg | −1.0 | −0.1 | Finasteride 1 mg-Women, Price et al., 2000 |
| 2% Minoxidil | 7.3 | 1.0 | 2% Minoxidil-Women, Godwin et al., 2017 |
| 5% Minoxidil | 7.6 | 1.0 | 5% Minoxidil-Women, Lucky et al., 2004 |
| Nutrafol | 9.2 | 1.3 | Nutrafol-Women, Ablon, 2018 |
| ALRV5XR | 30.1 | 4.1 | ALRV5XR-Arbor Life Labs, 2019 |

Figure 14:
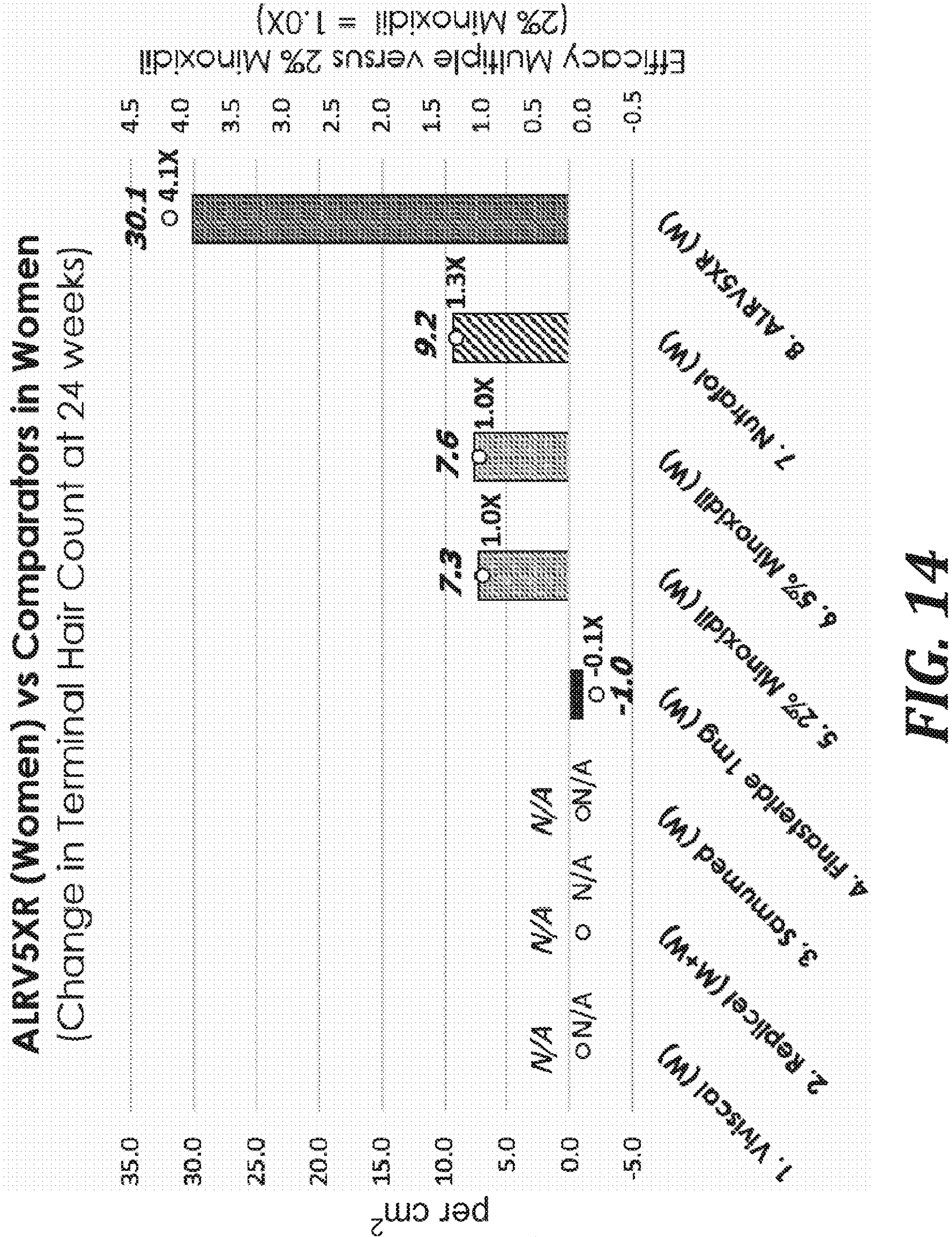
FIG. 14 is a bar chart comparing the present invention to the standard of care in women.

FIG. 14 is a bar chart comparing the present invention to the standard of care in Women. As can be readily observed, the present invention is far superior to the standard of care.

Example 25: Single Subject Change in Hair Over 12 Months

A Caucasian female age 63 with Blonde/Light (Grey <70%) hair. The hair condition was general thinning with chronic shedding. Overall health was normal with no medications. Patient exhibited mild weeping eczema on lower limbs. Her overall scalp condition was normal. She was treated daily with shampoo, conditioner and scalp cream in accordance with Formulation X for months 0-6 and then 3 times a week for months 7-12. Supplements in accordance with Formula XI were taken twice a day for the 12 months.

Patient underwent phototrichoscopy which is a non-invasive imaging method of diagnosing hair and scalp diseases without the need of biopsy or removing hair. It is used for quantitative evaluation and monitoring of hair loss in dermatological practice and in clinical trials. It is performed with a hand held dermoscope to obtain digital photographs of the visualized area. All hairs in a 1-2 sq cm area are trimmed 1 mm from the scalp surface, a small tattoo applied and a baseline photograph is taken. After 24-72 hours, the same region is photographed. By comparing the images, one can observe as to which hair fibers have grown, the rate of hair growth, the density of the hair and which hair fibers are missing. The images are repeated and compared to determine the changes overtime. The parameters of the equipment is in Table 42 below.

TABLE 42

| | |
|---|---|
| Methods: | Phototrichogram 48 hours apart |
| Imaging Equipment: | Firefly DE330T Trichoscope, |
| Magnification: | ×35 |
| Field of View: | 55.10 mm$^2$, |
| Resolution: | 1600 × 1200 (2 megapixels) |
| Analysis Software: | TrichosciencePro v1.5 |

A Trichogram image is shown in FIG. 10.

Table 43 below summarizes the change in hair quality during the study over 12 months.

TABLE 43

| Trichometric Measure | 12 Months |
|---|---|
| Overall density, hairs per $cm^2$ (Change %) | 260 (+35%) |
| Follicle Units (1-4 hairs per unit) | 134 (+25%) |
| Terminal (long/thick) scalp hairs per $cm^2$ (Change %) | 225 (+57%) |
| Vellus (short/thin) scalp hairs per $cm^2$ (Change %) | 34 (−31%) |
| Terminal % of Overall Density (Change %) | 87% (+18%) |
| Mean diameter of Terminal hairs, μm (Change %) | 69 (+13%) |
| Mean diameter of all hairs, μm (Change %) | 63 (+17%) |
| Mean growth rate, μm/24 hrs (Change %) | 335 (+33%) |

Table 44 below shows the change in hair quality at defined points during the study.

TABLE 44

Figure 17:
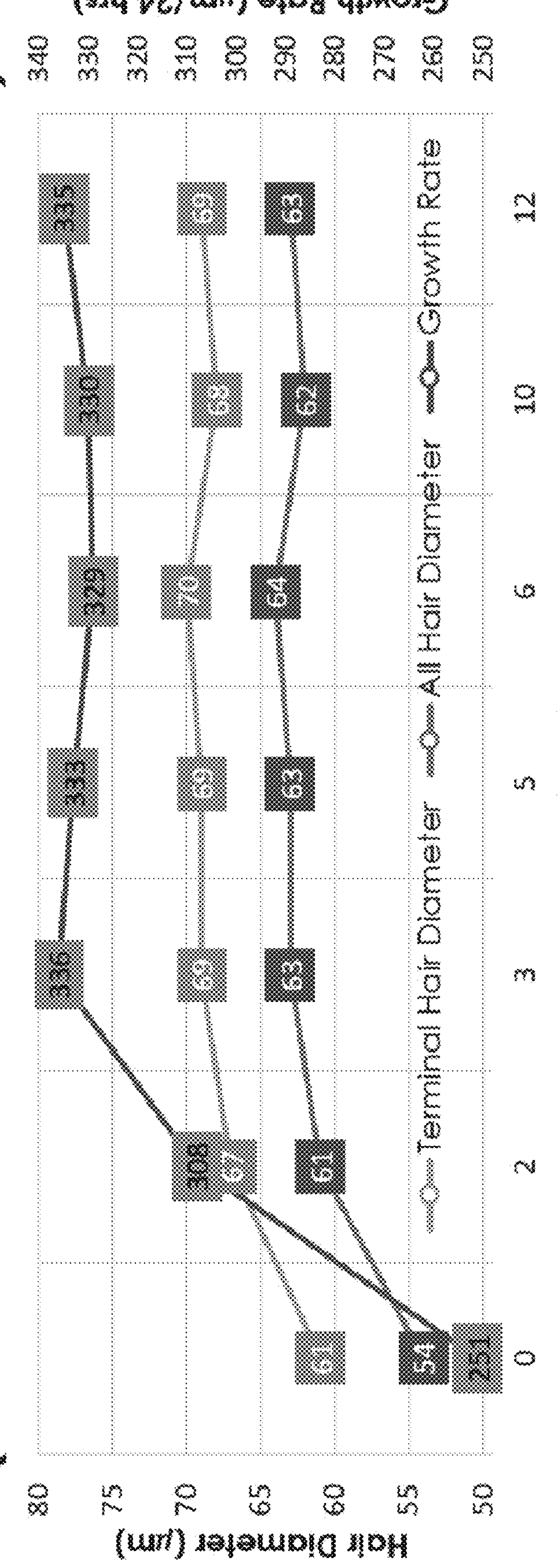
FIG. 17 is a graph showing change in hair shaft diameter and growth rate using the present invention.

| Time (Months) | 0 | 2 | 3 | 5 | 6 | 10 | 12 |
|---|---|---|---|---|---|---|---|
| Overall density, h/$cm^2$ | 192 | 220 | 240 | 254 | 250 | 250 | 260 |
| Change % | — | 15% | 25% | 32% | 30% | 30% | 35% |
| Terminal hairs per $cm^2$ | 143 | 181 | 205 | 221 | 216 | 216 | 225 |
| Change % | — | 27% | 43% | 55% | 51% | 51% | 57% |
| Vellus hairs per $cm^2$ | 49 | 38 | 34 | 33 | 34 | 34 | 34 |
| Change % | — | −22% | −31% | −33% | −31% | −31% | −31% |
| Terminal % of Overall Density | 74% | 82% | 85% | 87% | 86% | 86% | 87% |
| Mean diameter of Terminal hairs, μm | 61 | 67 | 69 | 69 | 70 | 68 | 69 |
| Change | — | 10% | 13% | 13% | 15% | 11% | 13% |
| Mean diameter of all hairs, μm | 54 | 61 | 63 | 63 | 64 | 62 | 63 |
| Change | — | 13% | 17% | 17% | 19% | 15% | 17% |
| Mean growth rate, μm/24 hrs | 251 | 308 | 336 | 333 | 329 | 330 | 335 |
| Change % | — | 23% | 34% | 33% | 31% | 31% | 33% |
| Anagen/Telogen hairs ratios, % | 80/20 | 83/17 | 78/22 | 77/23 | 67/33 | 80/20 | 80/20 |

change in hair shaft diameter and growth rate is shown in FIG. 17.

Scalp hairs are categorized as either Terminal (thicker and longer hairs) or Vellus (thinner and shorter hairs). A healthy looking scalp consists of at least 80% Terminal hair. A Terminal hair has a diameter>40 microns. There are 3 grades of Terminal hair thickness; Thin (40-60 μm), Regular(60-80 μm) and Thick (>80 μm). An increase in both the number and thickness of Terminal hairs, leads to animproved aesthetic effect of healthy looking head of hair. Table 45 below shows the improvement in terminal hair over time.

TABLE 45

Changes in Terminal Hair Quality Measures over 12 Months

| Time (Months) | | | 0 | 2 | 3 | 5 | 6 | 10 | 12 |
|---|---|---|---|---|---|---|---|---|---|
| Terminal Hairs | | | 143 | 181 | 205 | 221 | 216 | 216 | 225 |
| | Δ | % | — | 27% | 43% | 55% | 51% | 51% | 57% |
| Mean Diameter | | (μm) | 61 | 67 | 69 | 69 | 70 | 68 | 69 |
| | Δ | % | — | 10% | 13% | 13% | 15% | 11% | 13% |
| Terminal of Total | | % | 74% | 82% | 85% | 87% | 86% | 86% | 87% |
| Thin (40-60 μm) | | % | 64 | 37 | 31 | 30 | 30 | 30 | 29 |
| | Δ | % | — | −42% | −52% | −53% | −53% | −53% | −55% |
| Regular (60-80 μm) | | % | 23 | 39 | 42 | 43 | 33 | 39 | 42 |
| | Δ | % | — | 70% | 83% | 87% | 43% | 70% | 83% |
| Thick (80+ μm) | | % | 12 | 24 | 27 | 27 | 37 | 30 | 29 |
| | Δ | % | — | 100% | 125% | 125% | 208% | 150% | 142% |

Figure 18:
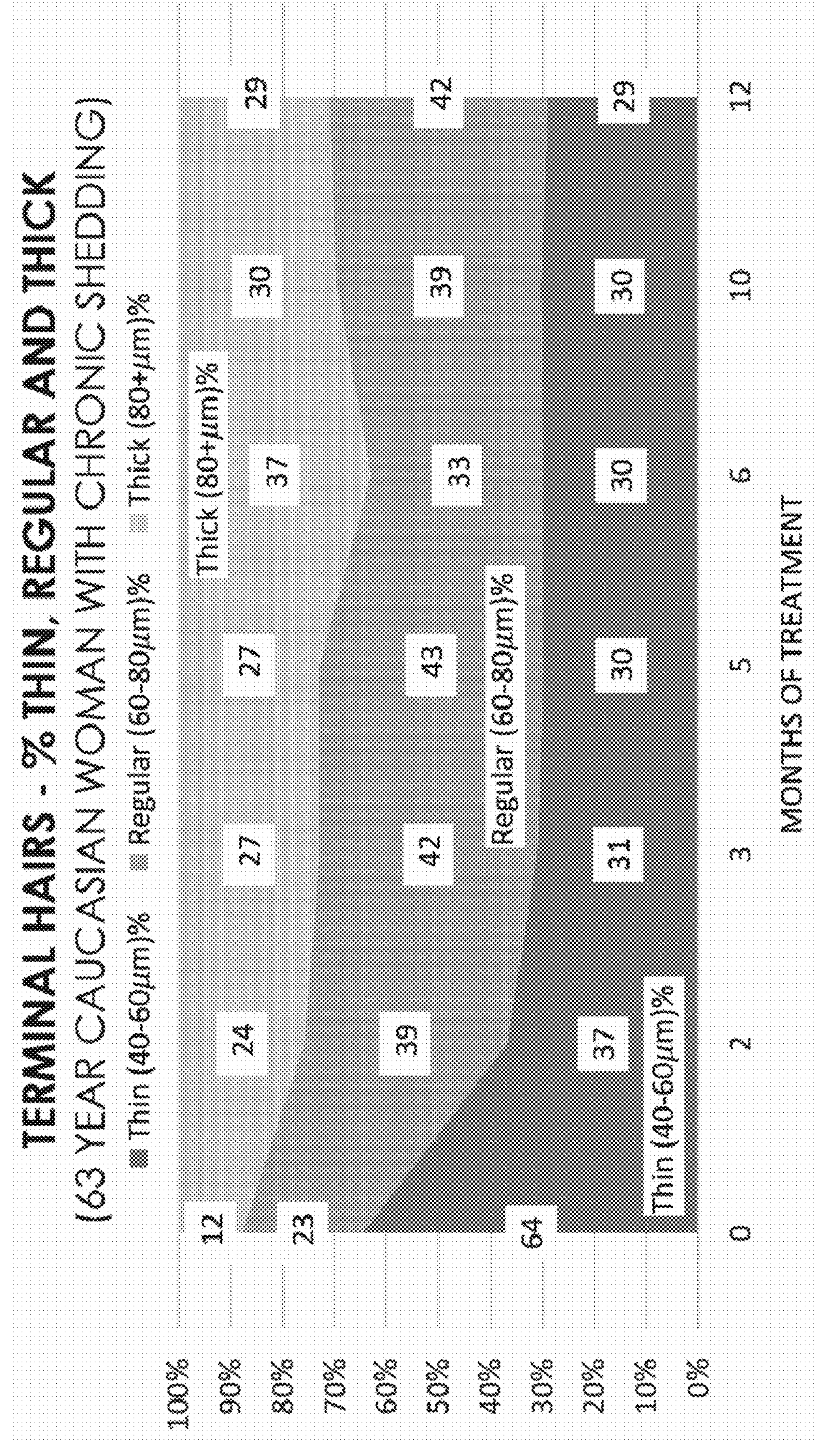
FIG. 18 is a graph showing change in Terminal Hair thickness ranges using the present invention.

The change in Terminal Hair thickness ranges is shown in FIG. 18.

A grouping of 1-5 Hairs emerging from the same hair pore in the scalp is known as a Follicular Unit (FU). Each Hair in the FU has its own follicle. The FU consists of a primary follicle and 1-4 secondary follicles. Re-activation of both follicles and FU's contributes to increase hair density. Table 46 below shows the improvement in FU.

TABLE 46

| Time (Months) | Total Hairs | Δ % | Total FU's | Δ % | Single FU's | Δ % | Double FU's | Δ % | Triple FU's | Δ % | Quadruple FU's | Δ % |
|---|---|---|---|---|---|---|---|---|---|---|---|---|
| 0 | 192 | — | 107 | — | 44 | — | 47 | — | 15 | — | 2 | — |
| 2 | 220 | 15% | 120 | 12% | 44 | 0% | 54 | 15% | 20 | 38% | 2 | 0% |
| 3 | 240 | 25% | 128 | 19% | 45 | 4% | 54 | 15% | 24 | 63% | 4 | 100% |
| 5 | 254 | 32% | 125 | 17% | 31 | −29% | 67 | 42% | 20 | 38% | 7 | 306% |
| 6 | 250 | 30% | 125 | 17% | 40 | −8% | 51 | 8% | 29 | 100% | 5 | 200% |
| 10 | 250 | 30% | 134 | 25% | 47 | 8% | 64 | 35% | 20 | 38% | 4 | 100% |
| 12 | 260 | 35% | 134 | 25% | 45 | 4% | 58 | 23% | 27 | 88% | 4 | 100% |

The patient reported being very happy with the results due to her hair being much thicker, having significantly less grey hair, the elimination of weeping eczema, an overall improvement in health, improvement in energy and more youthful looking skin.

Figure 19:
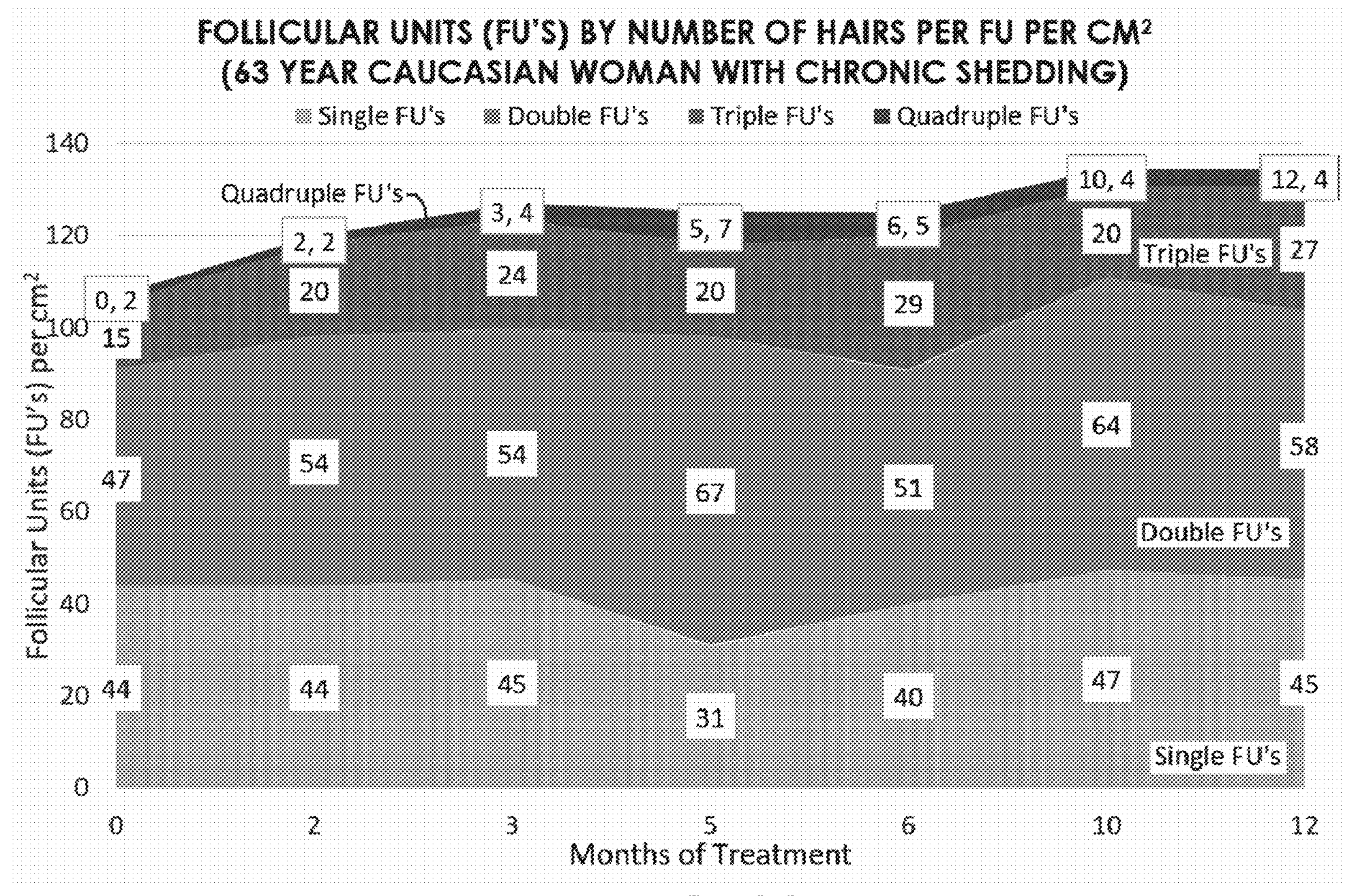
FIG. 19 is a graph showing change in Follicular Units using the present invention.

The change in Follicular Units is shown in FIG. 19.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Example 26 Single Subject

A female subject 58 years, caucasian, with grey hair. The hair condition was excessively thinning as persistent alopecia areata and androgentic alopecia. Overall health was normal with no medications. She was treated twice daily with Supplements in accordance with Formula XI for 12 months.

Figure 20B:
FIG. 20B is a black and white photograph showing change in hair density after treatment with the present invention.
Figure 20A:
FIG. 20A is a black and white photograph showing hair prior to treatment with the present invention.

FIG. 20A is a photograph showing her hair prior to treatment and FIG. 20 B shows change in hair density after using the present invention.

Figure 21B:
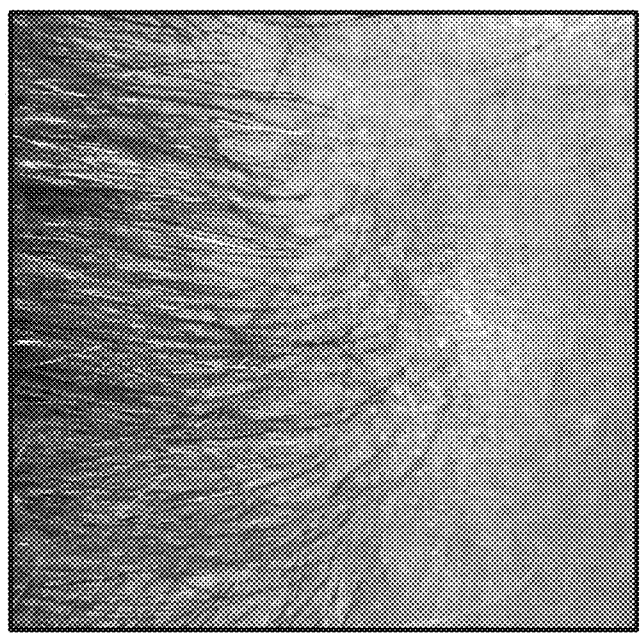
FIG. 21B is a black and white photograph showing change in hair color after using the present invention.
Figure 21A:
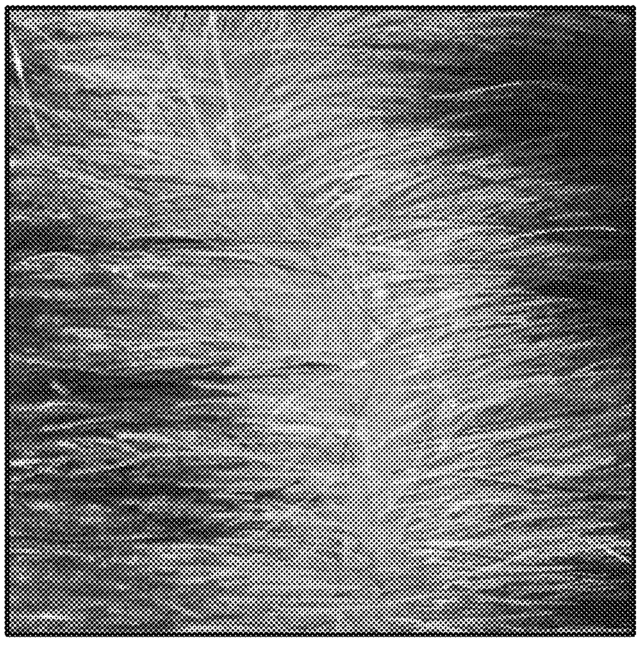
FIG. 21A is a black and white photograph showing hair prior to treatment with the present invention.

FIG. 21A is a photograph showing hair color before treatment. FIG. 21B shows the change in hair color after using the present invention.

Example 27 Single Subject

A female subject 52 years, caucasian, with psoriasis lesions on lower arms and legs. Overall health was normal with no medications except for prior use of TNF-alpha inhibiting medications which subject stopped due to side effects. She was treated twice daily with Cream in accordance with Formula X for 2 weeks.

Figure 22B:
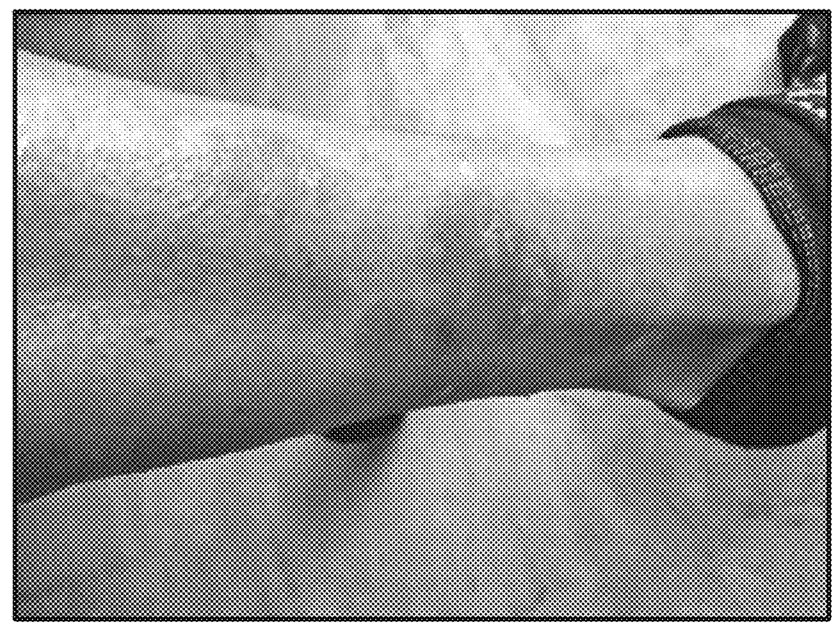
FIG. 22B is a black and white photograph showing change in psoriasis lesions after treatment with the present invention.
Figure 22A:
FIG. 22A is a black and white photograph showing psoriasis prior to treatment with the present invention.

FIG. 22A is a photograph showing the psoriasis lesions prior to treatment. FIG. 22B is a photograph showing the change in psoriasis lesions after using the present invention.

Example 28 Single Subject

A male subject 66 years, Caucasian, with thinning hair used Formula XI. Within 1 month of administering the ingestible formulation, the subject reported elimination of a multi-year, persistent presentation of *Malassezia Furfur*. The subject had been previously treated with itranol followed by cycloderm with success. The subject had given up on a treatment. The result was unexpected.

Example 29 Single Subject

A female subject 25 years, Caucasian, with thinning hair used Formula XI. Within 1 month of administering the ingestible formulation, the subject reported a elimination of the presentation of facial rosacea and acne.

One of skill in the art will appreciate that substantial departure from the examples disclosed herein is possible without departing from the spirit of the invention.

REFERENCES

[1] Xinhong Lim et al, Axin2 marks quiescent hair follicle bulge stem cells that are maintained by autocrine Wnt/β-catenin signaling, *Proceedings of the National Academy of Sciences* 2016; 113:E1498-E1505.

[2] Suda, T. and Arai, F. Wnt signaling in the niche. *Cell* 2008, 132:729-730.

[3] Clevers H., Nusse R. Wnt/β-catenin signaling and disease. *Cell* 2012; 149:1192-1205.

[4] Huelsken J., et al. O-Catenin controls hair follicle morphogenesis and stem cell differentiation in the skin. *Cell* 2001, 105:533-545.

[5] Wen-Hui Lien and Elaine Fuchs. Wnt some lose some: transcriptional governance of stem cells by Wnt/β-catenin signaling. *Genes & Dev.* 2014. 28:1517-1532.

[6] Kiichiro Yano, et al. Control of hair growth and follicle size by VEGF-mediated angiogenesis. *J Clin Invest* 2001; 107(4):409-417.

[7] Jean L., et al. Dermatology. Gulf Professional Publishing. pp. 1072.

[8] Jean L. Bolognia; et al. Dermatology. Gulf Professional Publishing. pp. 1072.

[9] Rittmaster R S. Fiasteride. *N Engl J Med* 1994; 330(2): 120-5.

[10] Shan-Chang Chueh, et al. Therapeutic strategy for hair regeneration: Hair cycle activation, niche environment modulation, wound-induced follicle neogenesis and stem cell engineering. *Expert Opin Biol Ther.* 2013 March; 13(3):377-391.

[11] Jean L. Bolognia; et al. Dermatology. Gulf Professional Publishing. pp. 1072.

[12] Rittmaster R S. Fiasteride. *N Engl J Med.* 1994; 330(2): 120-5.

[13] Goren A, et al. Clinical utility and validity of minoxidil response testing in androgenetic alopecia". *Dermatol Ther.* 2015, 28(1):13-6.

[14] Varothai, S; and Bergfeld, WF "Androgenetic alopecia: an evidence-based treatment update". *Am. J. Clin. Dermatol.* 2014, 15(3):217-30.

[15] Satish Patel, et al. Hair Growth: Focus on Herbal Therapeutic Agent. *Current Drug Discovery Technologies,* 2015, 12:21-42.

[16] Shan-Chang Chueh et al., Therapeutic strategy for hair regeneration: Hair cycle activation, niche environment modulation, wound-induced follicle neogenesis and stem cell engineering. *Expert Opin Biol Ther.* 2013 March; 13(3):377-391.

[17] Pisal Rishikaysh, et al. Signaling Involved in Hair Follicle Morphogenesis and Development. *Int. J. Mol. Sci.* 2014, 15:1647-1670.

[18] Paus, R., and Cotsarelis, G. The biology of hair follicles. *N. Engl. J. Med.* 1999, 341:491-497.

[19] Barsh, G. Of ancient tales and hairless tails. *Nat. Genet.* 1999, 22:315-316.

[20] Oshima, H., et al. Morphogenesis and renewal of hair follicles from adult multipotent stem cells. *Cell* 2001, 104:233-245.

[21] Sennett R, U and Rendl M: Mesenchymal-epithelial interactions during hair follicle morphogenesis and cycling. *Semin Cell* Dev Biol. 2012; 23(8):917-927.

[22] Alonso L, and Fuchs E: The hair cycle. *J Cell Sci.* 2006; 119(Pt 3):391-393.

[23] Alonso L, and Fuchs E: The hair cycle. *J Cell Sci.* 2006; 119(Pt 3):391-393.

[24] Alonso L, and Fuchs E: The hair cycle. *J Cell Sci.* 2006; 119(Pt 3): 391-393.

[25] Snippert, H. J.; et al. Lgr6 marks stem cells in the hair follicle that generate all cell lineages of the skin. *Science* 2010, 327:1385-1389.

[26] Goodell M A, and Rando T A. 2015. *Stem cells and healthy aging. Science* 350:1199-1204.

[27] Pisal Rishikaysh, et al. Signaling Involved in Hair Follicle Morphogenesis and Development. *Int. J. Mol. Sci.* 2014, 15:1647-1670.

[28] Lee J, and Tumbar T: Hairy tale of signaling in hair follicle development and cycling. *Semin Cell Dev Biol.* 2012; 23(8):906-916.

[29] Mahé Y F, et al.: Pro-inflammatory cytokine cascade in human plucked hair. *Skin Pharmacol.* 1996; 9(6):366-375.

[30] Billoni N, et al.: Thyroid hormone receptor beta1 is expressed in the human hair follicle. *Br J Dermatol.* 2000; 142(4):645-652.

[31] Inui S., and Itami S: Molecular basis of androgenetic alopecia: From androgen to paracrine mediators through dermal papilla. *J. Dermatol. Sci.* 2011; 61(1): 1-6.

[32] Khidhir K G., et al. The prostamide-related glaucoma therapy, bimatoprost, offers a novel approach for treating scalp alopecias. *FASEB J.* 2013; 27(2):557-567.

[33] Imamura T: Physiological functions and underlying mechanisms of fibroblast growth factor (FGF) family members: recent findings and implications for their pharmacological application. *Biol. Pharm. Bull.* 2014; 37(7): 1081-1089.

[34] Geyfman M., et al.: Resting no more: re-defining telogen, the maintenance stage of the hair growth cycle. *Biol. Rev. Camb. Philos. Soc.* 2015; 90(4):1179-1196.

[35] Yu B D., et al. Skin and hair: models for exploring organ regeneration. *Hum. Mol. Genet.* 2008 Apr. 15; 17(R1): R54-9.

[36] Purba T S., et al. Human epithelial hair follicle stem cells and their progeny: current state of knowledge, the widening gap in translational research and future challenges. *Bioessays* 2014 May; 36(5):513-25.

[37] Davis D S, and Callender V D. Review of quality of life studies in women with alopecia. *Int J Womens Dermatol* 2018; 4:18-22

[38] Lucy L Y. et al. Health-related quality of life (HRQoL) among patients with alopecia areata (AA): a systematic review. *J. Am. Acad. Dermatol.* 2016; 75:806-12.

[39] Thiedke C C. Alopecia in Women. *Am. Fam. Physician* 2003; 67:1007-14.

[40] Harvard Health Publishing—Harvard Medical School. Treating female pattern hair loss. available at: https://wwwhealthharvardedu/staying-healthy/treating-female-pattern-hair-loss 2018.

[41] Genetics Home Reference. Androgenetic alopecia. Available at: https://ghrnlmnihgov/condition/androgenetic-alopecia 2019.

[42] Cash T F. et al. Psychological effects on androgenetic alopecia on women: comparisons with balding and female control subjects. *J. Am. Acad. Dermatol.* 1993; 29:568-75.

[43] Williamson D. et al. The effect of hair loss on quality of life. *J. Eur. Acad. Dermatol. Venereol.* 2001; 15:137-9.

[44] Price V H. Treatment of hair loss. *N. Engl. J. Med.* 1999; 341:964-73.

[45] Mayo Clinic. Hair loss. available at: https://wwwmayoclinicorg/diseases-conditions/hair-loss/symptoms-causes/syc-20372926,2019.

[46] Krause K F, K., Biology of the Hair Follicle: The Basics. *Semin. Cutan. Med. Surg.* 2006; 25:2-10.

[47] Guo E L.; and Katta R. Diet and hair loss: effects of nutrient deficiency and supplement use. *Dermatol. Pract. Concept.* 2017; 7:1-10.

[48] Draelos Z D., et al. A pilot study evaluating the efficacy of topically applied niacin derivatives for treatment of female pattern alopecia. *J. Cosmet. Dermatol.* 2005; 4:258-61.

[49] Patel S. Sharma, et al. Hair Growth: Focus on Herbal Therapeutic Agent. *Curr. Drug Discov. Technol.* 2015; 12:21-42.

[50] Lourith N., and Kanlayavattanakul M. Hair loss and herbs for treatment. J. Cosmet. Dermatol. 2013; 12:210-22.

[51] Roh S S., et al. The hair growth promoting effect of *Sophora flavescens* extract and its molecular regulation. *J. Dermatol. Sci.* 2002; 30:43-49

[52] Fujita R., et al. Anti-androgenic activities of *Ganoderma lucidum. J. Ethnopharmacol.* 2005; 102:107-12.

[53] Takahashi T., et al. Proanthocyanidins from grape seeds promote proliferation of mouse hair follicle cells in vitro and convert hair cycle in vivo. *Acta Derm. Venereol.* 1998; 78:42-32.

[54] Shan-Chang Chueh et al. Therapeutic strategy for hair regeneration: Hair cycle activation, niche environment modulation, wound-induced follicle neogenesis and stem cell engineering. *Expert Opin. Biol. Ther.* 2013 March; 13(3):377-391.

[55] Pisal Rishikaysh, et al. Signaling Involved in Hair Follicle Morphogenesis and Development. *Int. J. Mol. Sci.* 2014, 15, 1647-1670.

[56] Paus, R., and Cotsarelis, G. The biology of hair follicles. *N. Engl. J. Med.* 1999, 341, 491-497.

[57] Barsh, G. Of ancient tales and hairless tails. *Nat. Genet.* 1999; 22:315-316.

[58] Oshima, H., et al. Morphogenesis and renewal of hair follicles from adult multipotent stem cells. *Cell* 104:233-245.

[59] Sennett R., and Rendl M.: Mesenchymal-epithelial interactions during hair follicle morphogenesis and cycling. *Semin. Cell. Dev. Biol.* 2012; 23(8):917-927.

[60] Alonso L., and Fuchs E.: The hair cycle. *J. Cell Sci.* 2006; 119(Pt 3):391-393.

[61] Alonso L., and Fuchs E.: The hair cycle. *J. Cell Sci.* 2006; 119(Pt 3):391-393.

[62] Alonso L., and Fuchs E.: The hair cycle. *J. Cell Sci.* 2006; 119(Pt 3):391-393.

[63] Snippert, H. J.; et al. Lgr6 marks stem cells in the hair follicle that generate all cell lineages of the skin. *Science* 2010, 327:1385-1389.

[64] Goodell M A., and Rando T A. . Stem cells and healthy aging. Science 2015; 350:1199-1204.

[65] Pisal Rishikaysh, et al. Signaling Involved in Hair Follicle Morphogenesis and Development. *Int. J. Mol. Sci.* 2014, 15:1647-1670.

[66] Lee J., and Tumbar T.: Hairy tale of signaling in hair follicle development and cycling. *Semin. Cell* Dev. Biol. 2012; 23(8):906-916.

[67] Mahé YF., et al.: Pro-inflammatory cytokine cascade in human plucked hair. *Skin Pharmacol.* 1996; 9(6):366-375.

[68] Billoni N., et al.: Thyroid hormone receptor beta1 is expressed in the human hair follicle. *Br. J. Dermatol.* 2000; 142(4):645-652.

[69] Inui S., and Itami S: Molecular basis of androgenetic alopecia: From androgen to paracrine mediators through dermal papilla. *J. Dermatol. Sci.* 2011; 61(1):1-6.

[70] Khidhir K G., et al.: The prostamide-related glaucoma therapy, bimatoprost, offers a novel approach for treating scalp alopecias. *FASEB J.* 2013; 27(2):557-567.

[71] Imamura T.: Physiological functions and underlying mechanisms of fibroblast growth factor (FGF) family members: recent findings and implications for their pharmacological application. *Biol. Pharm. Bull.* 2014; 37(7): 1081-1089.

[72] Geyfman M., et al.: Resting no more: re-defining telogen, the maintenance stage of the hair growth cycle. *Biol. Rev. Camb. Philos. Soc.* 2015; 90(4):1179-1196.

[73] Xinhong Lim et al. Auxin 2 marks quiescent hair follicle bulge stem cells that are maintained by autocrine Wnt/β-catenin signaling, *Proc. Natd. Acad. Sci USA* (2016), 113(11):E1498-1505.

[74] Suda, T.; and Arai, F. Wnt signaling in the niche. *Cell* 2008, 132:729-730.

[75] Clevers H., and Nusse R. Wnt/β-catenin signaling and disease. Cell 149 *Cell* 2012, 149:1192-1205.

[76] Huelsken J., et al. β-Catenin controls hair follicle morphogenesis and stem cell differentiation in the skin. *Cell* 2001, 105:533-545.

[77] Wen-Hui Lien and Elaine Fuchs. Wnt some lose some: transcriptional governance of stem cells by Wnt/β-catenin signaling. *Genes Dev.* 2014. 28:1517-1532.

[78] Kiichiro Yano, et al. Control of hair growth and follicle size by VEGF-mediated angiogenesis. *J. Clin. Invest* 2001 107(4):409-417.

[79] Jean L. et al. *Dermatology*. Gulf Professional Publishing. pp. 1072.

[80] Jean L. Bolognia; et al. *Dermatology*. Gulf Professional Publishing. pp. 1072.

[81] Rittmaster R S. Fiasteride. *N. Engl. J. Med.* 1994; 330 (2):120-5.

[82] Shan-Chang Chueh, et al. Therapeutic strategy for hair regeneration: Hair cycle activation, niche environment modulation, wound-induced follicle neogenesis and stem cell engineering. *Expert Opin. Biol. Ther.* 2013 March; 13(3):377-391.

[83] Jean L. Bolognia; et al. *Dermatology*. Gulf Professional Publishing. pp. 1072.

[84] Rittmaster R S. Fiasteride. *N. Engl. J. Med.* 1994; 330 (2):120-5.

[85] Goren, A. Clinical utility and validity of minoxidil response testing in androgenetic alopecia". *Dermatol Ther.* 28(1):13-6.

[86] Varothai, S.; and Bergfeld, WF. (July 2014). "Androgenetic alopecia: an evidence-based treatment update". *Am. J. Clin. Dermatol.* 2014; 15(3):217-30.

[87] Satish Patel, et al. Hair Growth: Focus on Herbal Therapeutic Agent. *Curr. Drug Discov. Technol.* 2015, 12:21-42.

[88] "Biotin—Fact Sheet for Health Professionals". Office of Dietary Supplements, National Institutes of Health. 8 Dec. 2017. Retrieved 25 Feb. 2018.

[89] "Biotin". Micronutrient Information Center, Linus Pauling Institute, Oregon State University, Corvallis, OR. 21 Oct. 2015. Retrieved 16 Jan. 2018.

[90] "Biotin". Micronutrient Information Center, Linus Pauling Institute, Oregon State University, Corvallis, OR. 21 Oct. 2015. Retrieved 16 Jan. 2018.

[91] "Biotin—Fact Sheet for Health Professionals". Office of Dietary Supplements, US-National Institutes of Health. 8 Dec. 2017. Retrieved 25 Feb. 2018.

[92] "Biotin". Micronutrient Information Center, Linus Pauling Institute, Oregon State University, Corvallis, OR. 21 Oct. 2015. Retrieved 16 Jan. 2018.

[93] "Biotin—Fact Sheet for Health Professionals". Office of Dietary Supplements, US Institutes of Health. 8 Dec. 2017. Retrieved 25 Feb. 2018.

[94] Food and Nutrition Board, Institute of Medicine. Biotin. Dietary Reference Intakes: Thiamin, Riboflavin, Niacin, Vitamin $B_6$, Vitamin $B_{12}$, Pantothenic Acid, Biotin, and Choline. Washington, D.C.: National Academy Press; 1998:374-389.

[95] Zempleno J., et al. Biotin requirements for DNA damage prevention. *Mutat. Res.* 2012; 733(1-2):58-60.

[96] Saggerson D. Malonyl-CoA, a key signaling molecule in mammalian cells. *Annu. Rev. Nutr.* 2008; 28:253-272.

[97] Saggerson D. Malonyl-CoA, a key signaling molecule in mammalian cells. *Annu. Rev. Nutr.* 2008; 28:253-272.

[98] Saggerson D. Malonyl-CoA, a key signaling molecule in mammalian cells. *Annu. Rev. Nutr.* 2008; 28:253-272.

[99] Saggerson D. Malonyl-CoA, a key signaling molecule in mammalian cells. *Annu. Rev. Nutr.* 2008; 28:253-272.

[100] Wong R W., et al. Antimicrobial activity of Chinese medicine herbs against common bacteria in oral biofilm. A pilot study. *Int. J. Oral Maxillofac. Surg.* 2010; 39:599-605.

[101] Leach F S. Anti-microbial properties of *Scutellaria baicalensis* and Coptis *chinensis*, two traditional Chinese medicines. *Biosci. Horiz.* 2011; 4:9.

[102] Beijing: People's Medical Publishing House; 2005. Pharmacopoeia of the People's Republic of China.

[103] Du P., et al. Antibacterial activity of 20 kinds of Chinese medicinal materials for *Helicobacter pylori* in vitro. Zhong Yao Cai. 2001; 24:188-9.

[104] Wang Q., et al. Naturally derived anti-inflammatory compounds from Chinese medicinal plants. *J. Ethnopharmacol.* 2013; 146:9-39.

[105] Zhou L., and Zhou B Y. Influence of baicalin on TNF-alpha and soluble intercellular adhesion molecule-1 in rats infected with *Pneumocystis carinii. Zhongguo Ji Sheng Chong Xue Yu Ji Sheng Chong Bing Za Zhi.* 2009; 27:144-7.

[106] Li, H. B.; et al. Separation methods used for *Scutellaria baicalensis* active components. *J. Chromatogr*. B2004, 812:277-290.

[107] Zhao S M., et al. Protective effect of scutellaria *baicalensis* stem-leaf total flavonoid on lipid peroxidation induced by myocardial ischemia reperfusion in rats. Chin. *J. Anat.* 2006; 29:450-452.

[108] Choi J., et al. Flavones from *Scutellaria baicalensis* Georgi attenuate apoptosis and protein oxidation in neuronal cell lines. *Biochim. Biophys. Acta.* 2002; 1571:201-210.

[109] Choi J., et al. Flavones from *Scutellaria baicalensis* Georgi attenuate apoptosis and protein oxidation in neuronal cell lines. *Biochim. Biophys. Acta.* 2002; 1571:201-210.

[110] Choi J., et al. Flavones from *Scutellaria baicalensis* Georgi attenuate apoptosis and protein oxidation in neuronal cell lines. *Biochim. Biophys. Acta.* 2002; 1571:201-210.

[111] Kim H., et al. The plant flavonoid wogonin suppresses death of activated C6 rat glial cells by inhibiting nitric oxide production. *Neurosci. Lett.* 2001; 309:67-71.

[112] Kim A R., et al. The inhibitory effect of *Scutellaria baicalensis* extract and its active compound, baicalin, on the translocation of the androgen receptor with implications for preventing androgenetic alopecia. *Planta* Med. 2014 February; 80(2-3):153-8.

[113] Nam K W., et al. The role of wogonin in controlling SOCS3 expression in neuronal cells. *Biochem. Biophys, Res. Commun.* 2014; 450:1518-1524.

[114] Lucas C D., et al. Wogonin induces eosinophil apoptosis and attenuates allergic airway inflammation. *Am. J. Resp. Crit. Care Med.* 2015; 191:626-636.

[115] Chirumbolo S. Anticancer properties of the flavone wogonin. *Toxicology.* 2013; 314:60-64.

[116] Chen F., et al. Wogonin protects rat dorsal root ganglion neurons against tunicamycin-induced ER stress through the PERKeIF2alpha-ATF4 signaling pathway. *J. Mol. Neurosci.* 2015; 55:995-1005.

[117] Chen S., et al. Wogonin inhibits LPS-induced inflammatory responses in rat dorsal root ganglion neurons via inhibiting TLR4-MyD88-TAK1-mediated NF-kappaB, MAPK signaling pathway. *Cell*. Mol. Neurobiol. 2015; 35:523-531.

[118] Qinmeng Shu, et al. Wogonin induces retinal neuron-like differentiation of bone marrow stem cells by inhibiting Notch-1 signaling. *Oncotarget,* 2017, Vol. 8, (No. 17), pp: 28431-28441.

[119] Hee Soon Shin, et al. Skullcap (*Scutellaria baicalensis*) Extract and Its Active Compound, Wogonin, Inhibit Ovalbumin-Induced Th2-Mediated Response. Molecules 2014, 19, pp: 2536-2545.

[120] Nantana Sittichai; Chayan Picheansoothon, eds. (2014). *Herbal Medicines Used in Primary Health Care in ASEAN. Department for Development of Thai Traditional and Alternative Medicine*. p. 148-149.

[121] Chung, I. M.; et al. (2017). "Ethnopharmacological uses, phytochemistry, biological activities, and biotechnological applications of *Eclipta prostrata". Applied Microbiology and Biotechnology.* 101(13): 5247-5257.

[122] K. Ma-Ma, et al. "The protective effect of *Eclipta alba* on carbon tetrachloride-induced acute liver damage," *Tox. App. Pharmacol.* 1978; 45(3):723-728.

[123] H. Wagner, et al. "Coumestans as the main active principles of the liver drugs *Eclipta alba* and Wedelia calendulacea," *Planta Medica,* 1986, 5:370-374.

[124] D. Manvar, et al. "Identification and evaluation of anti-hepatitis C virus phytochemicals from *Eclipta alba,*" *J. Ethnopharmacol.* 2012, 144(3):545-554.

[125] Navneet Kumar Yadav, et al., "Alcoholic Extract of *Eclipta alba* Shows In Vitro Antioxidant and Anticancer Activity without Exhibiting Toxicological Effects," *Medicine and Cell* Longevity 2017, Article ID 9094641.

[126] Navneet Kumar Yadav, et al. "Alcoholic Extract of *Eclipta alba* Shows In Vitro Antioxidant and Anticancer Activity without Exhibiting Toxicological Effects," *Oxidative Medicine and Cell* Longevity 2017; Article ID 9094641.

[127] K. Prabu, et al. "Hepatoprotective effect of *Eclipta alba* on paracetamol induced liver toxicity in rats," *J. Microbiol. Biotechnol. Res.* 2011; 1:75-79.

[128] J. Ananthi, et al. "Antihyperglycemic activity of *Eclipta alba* leaf on alloxan induced diabetic rats," *Yale J. Biol. Med.* 2003; 76(1-6):97-102.

[129] C.-F. Chan, et al. "Potent antioxidative and UVB protective effect of water extract of *Eclipta* prostrate L," *The Scientific World Journal,* 2014, vol. 2014, Article ID 759039, 8 pages.

[130] S. S. Kumar, et al. "Evaluation of anti-Inflammatory activity of *Eclipta alba* in rats," *Ancient Science of Life,* 2005, 112-118.

[131] O. Banji, et al. "Investigation on the effect of *Eclipta alba* on animal models of learning and memory," *Indian J. Physiol. Pharmacol.* 2007, 54(3):274-278.

[132] R. K. Roy, et al. "Hair growth promoting activity of *Eclipta alba* in male albino rats," *Arch. Dermatol. Res.* 2008, 300(7):357-364.

[133] K. Datta, et al. "alba extract with potential for hair growth promoting activity," *J. Ethnopharmacol.* 2009, 124(3):450-456.

[134] Xican Li, et al. "Effect and mechanism of wedelolactone as antioxidant-coumestan on OH-treated mesenchymal stem cells," *Arabian J. Chem.* 2020; 13(1):184-192.

[135] Vivier M A., and Pretorius I S. Genetically tailored grapevines for the wine industry.—*Trends Biotechnol.* 2002; 20:472-478.

[136] Ray S., al. Acute and long-term safety evaluation of a novel IH636 grape seed proanthocyanidin extract. —*Res. Commun. Mol. Pathol. Pharmacol.* 2001; 109:165-197.

[137] Renaud S., and de Lorgeril M. Wine, alcohol, platelets, and the French paradox for coronary heart disease. *Lancet.* 1992; 339:1523-1526.

[138] Gonzalez-Paramas A M., et al. Flavanol content and antioxidant activity in winery byproducts. *J. Agric. Food Chem.* 2004; 52:234-238.

[139] Da Silva J M R., et al. Oxygen free radical scavenger capacity in aqueous models of different procyanidins from grape seeds. *J. Agric. Food Chem.* 1991; 39:1549-1552.

[140] Felice F., et al. Delivery of natural polyphenols by polymeric nanoparticles improves the resistance of endothelial progenitor cells to oxidative stress. *Eur. J. Pharm. Sci.* 2013 Nov. 20; 50(3-4):393-9.

[141] Fazlul H. Sarkar, et al. "The role of nutraceuticals in the regulation of Wnt and Hedgehog signaling in cancer," *Cancer Metastasis Rev.* 2010 September; 29(3): 383-394.

[142] Po-Cheng Lin, et al. Botanical Drugs and Stem Cells. *Cell* Transplantation 2011; 20:71-83.

[143] Yu B D., et al. Skin and hair: models for exploring organ regeneration. *Hum. Mol. Genet.* 2008 Apr. 15; 17(R1): R54-9.

[144] Purba T S., et al. Human epithelial hair follicle stem cells and their progeny: current state of knowledge, the widening gap in translational research and future challenges. *Bioassays* 2014 May; 36(5):513-25.

[145] Blume-Peytavi, U., et al. Hair Growth and Disorders. Springer-Verlag Berlin Heidelberg. 2008.

[146] Paus, R., Cotsarelis, G. The biology of hair follicles. *N. Engl. J. Med.* 1999; 341:491-497.

[147] Stenn, K., et al. 1998. Growth of the hair follicle: a cycling and regenerating biological system. In: Molecular basis of epithelial appendage morphogenesis. C.-M. Chuong, editor. R. G. Landes Co. Austin, Texas, USA. 111-130.

[148] Alonso L., and Fuchs E: The hair cycle. *J. Cell Sci.* 2006; 119(Pt 3):391-393.

[149] Lee J., and Tumbar T: Hairy tale of signaling in hair follicle development and cycling. *Semin. Cell Dev. Biol.* 2012; 23(8):906-916.

[150] Mahé YF., et al.: Pro-inflammatory cytokine cascade in human plucked hair. *Skin Pharmacol.* 1996; 9(6):366-375.

[151] Inui S., and Itami S.: Molecular basis of androgenetic alopecia: From androgen to paracrine mediators through dermal papilla. *J. Dermatol. Sci.* 2011; 61(1):1-6.

[152] Gerst C., et al., Type-1 steroid 5 alpha-reductase is functionally active in the hair follicle as evidenced by new selective inhibitors of either type-1 or type-2 human steroid 5 alpha-reductase. *Exp. Dermatol.* 2002; 11(1):52-58.

[153] Khidhir K G., et al.: The prostamide-related glaucoma therapy, bimatoprost, offers a novel approach for treating scalp alopecias. *FASEB J.* 2013; 27(2):557-567.

[154] Imamura T.: Physiological functions and underlying mechanisms of fibroblast growth factor (FGF) family members: recent findings and implications for their pharmacological application. *Biol. Pharm. Bull.* 2014; 37(7): 1081-1089.

[155] Bernard B A. Advances in Understanding Hair Growth [version 1; referees: 2 approved] FI000Research 2016, 5 (F1000 Faculty Rev):147.

[156] Cranwell W., and Sinclair R. Male Androgenetic Alopecia. [Updated 2016 Feb. 29]. In: De Groot L J, Beck-Peccoz P, Chrousos G, et al., editors. Endotext [Internet]. South Dartmouth (MA): MDText.com, Inc.; 2000

[157] Ito T. Recent Advances in the Pathogenesis of Autoimmune Hair Loss Disease Alopecia Areata. Clin. Devel. *Immunol.* 2013; 2013:348546.

[158] Colombe L., et al.: Prostaglandin metabolism in human hair follicle. *Exp. Dermatol.* 2007; 16(9):762-769.

[159] Garza L A., et al.: Prostaglandin D 2 inhibits hair growth and is elevated in bald scalp of men with androgenetic alopecia. *Sci. Transl. Med.* 2012; 4(126):126ra34.

[160] Rishikaysh P., al. Signaling Involved in Hair Follicle Morphogenesis and Development. *Int. J. Mol. Sci.* 2014; 15(1):1647-1670.

[161] Imamura T. Physiological functions and underlying mechanisms of fibroblast growth factor (FGF) family members: recent findings and implications for their pharmacological application. *Biol. Pharm. Bull.* 2014; 37(7): 1081-9.

[162] Shin H S., et al. Efficacy of 5% minoxidil versus combined 5% minoxidil and 0.01% tretinoin for male pattern hair loss: a randomized, double-blind, comparative clinical trial. *Am. J. Clin. Dermatol.* 2007; 8(5):285-90.

[163] Mysore V., and Shashikumar B. M. Guidelines on the use of finasteride in androgenetic alopecia. Indian *J. Dermatol. Venereol.* Leprol. 2016; 82:128-34.

[164] Goldberg, L. J. et al., Nutrition and Hair. *Clin. Dermatol.* 2010 July-August; 28(4):412-9.

[165] Szyszkowska B., et al. The influence of selected ingredients of dietary supplements on skin condition. *Adv. Dermatol.* Allergol. 2014; 31(3):174-181.

[166] Bassino E., et al. Effects of flavonoid derivatives on human microvascular endothelial cells. *Nat. Prod. Res.* 2016 Mar. 2:1-4.

[167] Kim M H., et al. Beneficial Effects of Astragaloside IV for Hair Loss via Inhibition of Fas/Fas L-Mediated Apoptotic Signaling. *PLoS ONE* 2014 9(3):e92984.

[168] Takahashi T., et al. Procyanidin i oligomers selectively and intensively promote proliferation of mouse hair epithelial cells in vitro and activate hair follicle growth in vivo. *J. Invest. Dermatol.* 1999; 112:310-316.

[169] Takahashi T., et al. Investigation of the topical application of procyanidin oligomers from apples to identify their potential use as a hair-growing agent. *J. Cosmetic Dermatol.* 4:245-249

[170] Kim A., et al. The Inhibitory Effect of *Scutellaria baicalensis* Extract and Its Active Compound, Baicalin, on the Translocation of the Androgen Receptor with Implications for Preventing Androgenetic Alopecia. *Planta* Med. 2014; 80:153-158

[171] Datta K., et al. *Eclipta alba* extract with potential for hair growth promoting activity. *J Ethnopharmacol.* 2009 Jul. 30; 124(3):450-6.

[172] Li Y., et al. Hair Growth Promotion Activity and Its Mechanism of *Polygonum multiflorum*. Evid. Based Complement. Alternat. Med. 2015; 2015:517901.

[173] Schmid D., et al. The FGF7 and Noggin Genes are Key Targets to Treat Hair Loss. *SOFW-J.* 2013; 139:18-22

[174] Toru Imamura et al., 2009; Hair regrowth promoter EP 2127674 A1

[175] Zuo C., et al. *Astragalus* mongholicus ameliorates renal fibrosis by modulating HGF and TGF-beta in rats with unilateral ureteral obstruction *J. Zhejiang Univ. Sci. B.* 2009 May; 10(5):380-90.

[176] Ono T., et al. Induction of hepatocyte growth factor production in human dermal fibroblasts and their proliferation by the extract of bitter melon pulp. *Cytokine.* 2009 April; 46(1):119-26.

[177] Roh S S., et al. The hair growth promoting effect of *Sophora flavescens* extract and its molecular regulation. *J. Dermatol. Sci.* 2002 October; 30(1):43-9.

[178] Lam H W., et al. The angiogenic effects of *Angelica sinensis* extract on HUVEC in vitro and zebrafish in vivo. *Acta Biochim. Pol.* 2011; 58(4):449-6

[179] Suo Z., et al. Impact of matrine on inflammation related factors in rat intestinal microvascular endothelial cells. *J. Ethnopharmacol.* 2009 Sep. 25; 125(3):404-9.

[180] Noguchi K., et al. Effect of caffeine contained in a cup of coffee on microvascular function in healthy subjects. *J. Pharmacol. Sci.* 2015 February; 127(2):217-22. doi: 10.1016/j.jphs.2015.01.003. Epub 2015 Jan. 28.

[181] Jian J., et al. Calycosin-7-O-β-d-glucopyranoside stimulates osteoblast differentiation through regulating the BMP/WNT signaling pathways. *Acta Pharm Sin B.* 2015 September; 5(5):454-60.

[182] http://www.personalcaremagazine.com/print/11018

[183] Zhang L., et al. *Astragalus membranaceus* extract promotes neovascularisation by VEGF pathway in rat model of ischemic injury. Pharmazie 2011 February; 66(2):144-50.

[184] Kern M., et al. Apple polyphenols affect protein kinase C activity and the onset of apoptosis in human colon carcinoma cells. *J. Agric. Food Chem.* 2007 Jun. 27; 55(13):4999-5006.

[185] Liu H., et al. Effect of grape procyanidins on the protein kinase and proliferative cell nuclear antigen protein expression of mice hepatic cells. Wei Sheng Yan Jiu 2007 January; 36(1):31-3.

[186] Rau O., et al. Carnosic acid and carnosol, phenolic diterpene compounds of the labiate herbs rosemary and sage, are activators of the human peroxisome proliferator-activated receptor gamma. *Planta Med.* 2006 August; 72(10):881-7.

[187] Park H J., et al. Topical application of *Polygonum multiflorum* extract induces hair growth of resting hair follicles through upregulating Shh and β-catenin expression in C57BL6 mice. *J. Ethnopharmacol.* 2011 May 17; 135(2):369-75.

[188] Li Y., et al. Hair Growth Promotion Activity and Its Mechanism of *Polygonum multiflorum*. Evid. Based Complement. Alternat. Med. 2015:517901. doi: 10.1155/2015/517901. Epub 2015 Jul. 30.

[189] Shin S H., et al. Baicalin, a flavonoid, affects the activity of human dermal papilla cells and promotes anagen induction in mice. *Naunyn Schmiedebergs Arch Pharmacol.* 2015 May; 388(5):583-6.

[190] Takahashi T., et al. Improvement of androgenetic alopecia with topical *Sophora flavescens* Aiton extract, and identification of the two active compounds in the extract that stimulate proliferation of human hair keratinocytes. *Clin. Exp. Dermatol.* 2016 April; 41(3):302-7.

[191] Les F., et al. Bioactive properties of commercialised pomegranate (*Punica granatum*) juice: antioxidant, antiproliferative and enzyme inhibiting activities. *Food Funct.* 2015 June; 6(6):2049-57.

[192] Kim E H., et al. Anti-inflammatory effects of *Scutellaria baicalensis* extract via suppression of immune modulators and MAP kinase signaling molecules. *J. Ethnopharmacol.* 2009 Nov. 12; 126(2):320-31.

[193] Wun Z Y., et al. Anti-inflammatory effect of sophoraflavanone G isolated from *Sophora flavescens* in lipopolysaccharide-stimulated mouse macrophages. *Food Chem. Toxicol.* 2013 December; 62:255-61.

[194] Habijanic J., et al. Submerged cultivation of *Ganoderma lucidum* and the effects of its polysaccharides on the production of human cytokines TNF-α, IL-12, IFN-γ, IL-2, IL-4, IL-10 and IL-17. *Nat. Biotechnol.* 2015 Jan. 25; 32(1):85-95.

[195] Silva A M., et al. Aqueous extract of *Rosmarinus officinalis* L. inhibits neutrophil influx and cytokine secretion. *Phytother Res.* 2015 January; 29(1):125-33.

[196] Li B Q., et al. The flavonoid baicalin exhibits anti-inflammatory activity by binding to chemokines. Immunopharmacology 2000 September; 49(3):295-306.

[197] Ryu M., et al. Astragali Radix elicits anti-inflammation via activation of MKP-1, concomitant with attenuation of p38 and Erk. *J Ethnopharmacol.* 2008 Jan. 17; 115(2): 184-93.

[198] Dudhgaonkar S., et al. Suppression of the inflammatory response by triterpenes isolated from the mushroom *Ganoderma lucidum. Int. Immunopharmacol.* 2009 October; 9(11):1272-80.

[199] Denis M C., et al. Apple peel polyphenols and their beneficial actions on oxidative stress and inflammation. *PLoS One* 2013; 8(1):e53725.

[200] Kuo C F., et al. Anti-inflammatory effects of supercritical carbon dioxide extract and its isolated carnosic acid from *Rosmarinus officinalis* leaves. *J Agric Food Chem.* 2011 Apr. 27; 59(8):3674-85.

[201] Hong G E., et al. Flavonoids Identified from Korean *Scutellaria baicalensis* Georgi Inhibit Inflammatory Signaling by Suppressing Activation of NF-κB and MAPK in RAW 264.7 Cells. Evid Based Complement Alternat Med. 2013; 912031.

[202] Yu M H., et al. Suppression of LPS-induced inflammatory activities by *Rosmarinus officinalis* L. *Food Chem.* 2013 Jan. 15; 136(2):1047-54.

[203] Yang Y Z., et al. Wogonoside displays anti-inflammatory effects through modulating inflammatory mediator expression using RAW264.7 cells. *J. Ethnopharmacol.* 2013 Jun. 21; 148(1):271-6.

[204] Du X., et al. *Astragalus* polysaccharides enhance the humoral and cellular immune responses of hepatitis B surface antigen vaccination through inhibiting the expression of transforming growth factor β and the frequency of regulatory T cells. *FEMS Immunol. Med. Microbiol.* 2011 November; 63(2):228-35.

[205] Begum S., et al. Exogenous stimulation with *Eclipta alba* promotes hair matrix keratinocyte proliferation and downregulates TGF-β1 expression in nude mice. *Int. J. Mol.*

*Med.* 2015 February; 35(2):496-502.

[206] Georgiev V., et al. Recent advances and uses of grape flavonoids as nutraceuticals. *Nutrients* 2014 Jan. 21; 6(1): 391-415.

[207] Panahi Y., et al. Rosemary oil vs minoxidil 2% for the treatment of androgenetic alopecia: a randomized comparative trial. Skinmed. 2015 January-February; 13(1): 15-21.

[208] Kim A R., et al. The inhibitory effect of *Scutellaria baicalensis* extract and its active compound, baicalin, on the translocation of the androgen receptor with implications for preventing androgenetic alopecia. *Planta* Med. 2014 February; 80(2-3):153-8.

[209] Fischer T W., et al. Differential effects of caffeine on hair shaft elongation, matrix and outer root sheath keratinocyte proliferation, and transforming growth factor-β2/insulin-like growth factor-1-mediated regulation of the hair cycle in male and female human hair follicles in vitro. *Br. J. Dermatol.* 2014 November; 171(5):1031-43.

[210] Fu J., et al. Review of the botanical characteristics, phytochemistry, and pharmacology of *Astragalus membranaceus* (Huangqi). *Phytother. Res.* 2014 September; 28(9):1275-83.

[211] Sidra S., et al. Accentuating the prodigious significance of *Eclipta alba*—an inestimable medicinal plant. *Pak. J. Pharm. Sci.* 2013 November; 26(6):1259-66.

[212] Shi M., et al. Antioxidant and immunoregulatory activity of *Ganoderma lucidum* polysaccharide (GLP). *Carbohydr. Polym.* 2013 Jun. 5; 95(1):200-6.

[213] Hyson D A. A comprehensive review of apples and apple components and their relationship to human health. Adv Nutr. 2011 September; 2(5):408-20.

[214] Nabavi S F., et al. The cellular protective effects of rosmarinic acid: from bench to bedside. *Curr. Neurovasc. Res.* 2015; 12(1):98-105.

[215] Li C., et al. Pharmacological effects and pharmacokinetics properties of Radix Scutellariae and its bioactive flavones. *Biopharm Drug Dispos.* 2011 November; 32(8): 427-45.

[216] He X., et al. Local and traditional uses, phytochemistry, and pharmacology of *Sophora japonica* L.: A review. *J. Ethnopharmacol.* 2016 Apr. 13. pii: S0378-8741(16): 30205-7.

[217] Georgiev V., et al. Recent advances and uses of grape flavonoids as nutraceuticals. *Nutrients* 2014 Jan. 21; 6(1): 391-415.

[218] Abdull Razis A F., et al. Health benefits of Moringa oleifera. *Asian Pac. J. Cancer Prev.* 2014; 15(20):8571-6.

[219] Usta C., et al. The pharmacological use of ellagic acid-rich pomegranate fruit. *Int. J. Food Sci. Nutr.* 2013 November; 64(7):907-13.

[220] Kim M H., et al. *Angelica sinensis* induces hair regrowth via the inhibition of apoptosis signaling. *Am. J. Chin. Med.* 2014; 42(4):1021-34.

[221] Ren S., et al. Pharmacological effects of Astragaloside IV: a literature review. *J. Tradit. Chin. Med.* 2013 June; 33(3):413-6.

[222] Lin M., et al. The protective effect of baicalin against renal ischemia-reperfusion injury trough inhibition of inflammation and apoptosis. *BMC Complement Altern Med.* 2014 Jan. 13; 14:19.

[223] Xia E Q., et al. Biological activities of polyphenols from grapes. *Int J Mol Sci.* 2010 Feb. 4; 11(2):622-46.

[224] Jian J., et al. Calycosin-7-O-β-d-glucopyranoside stimulates osteoblast differentiation through regulating the BMP/WNT signaling pathways. *Acta Pharm.* Sin. B 2015 September; 5(5):454-60.

[225] Vega-Gálvez A., et al. Nutrition facts and functional potential of *quinoa* (*Chenopodium quinoa* wild.), an ancient Andean grain: a review. *J. Sci. Food Agric.* 2010 December; 90(15):2541-7.

[226] Bishop K S., et al. From 2000 years of *Ganoderma lucidum* to recent developments in nutraceuticals. Phytochemistry 2015 June; 114:56-65.

[227] Hyson D A. A Comprehensive Review Of Apples And Apple Components And Their Relationship To Human Health. Adv. Nutr. 2011 September; 2(5):408-20.

[228] Abdull Razis A F., et al. Health benefits of Moringa oleifera. *Asian Pac J Cancer Prev.* 2014; 15(20):8571-6.

[229] Belski R. Fiber, protein, and lupin-enriched foods: role for improving cardiovascular health. *Adv. Food Nutr. Res.* 2012; 66:147-215.

[230] Veeman et al., *Curr. Biol.* 2003 Apr. 15. 13(8):680-5.

We claim:

1. A method for maintaining or increasing proliferation of dermal papilla stem cells, follicular unit density, total hairs per follicular unit, terminal hairs per follicular unit, anagen hairs per follicular unit, hair diameter, hair growth rate, follicle productivity, or scalp coverage comprising administering a composition comprising:

| | |
|---|---|
| biotin | 0.005% to 1.00%; |
| caffeine | 0.0001% to 1.00%; |
| *Chenopodium quinoa* | 0.1% to 2.00%; |
| *Eclipta prostrata* | 0.01% to 4.00%; |
| *Lupinus* | 0.01% to 6.00%; |
| *Malus domestica* | 0.01% to 4.00%; |
| methylsulfonylmethane | 0.005% to 2.00%; |
| *Momordica charantia* | 0.01% to 6.00%; |
| *Moringa olifiera* | 0.01% to 6.00%; |
| *Ocimum basilicum* | 0.01% to 6.00%; |
| *Pisum sativum* | 0.01% to 6.00%; |
| *Rosmarinus officinalis* | 0.01% to 4.00%; |
| *Scutellaria baicalensis* | 0.01% to 4.00%; |
| Vitamin E (α tocopherol) | 0.005% to 2.00%; and |
| proanthocyanidin | 0.01% to 4.00%. |

2. The method according to claim 1, wherein the composition is a topical composition and further comprises a fragrance ingredient comprising one or more of *Cedrus deodora, Juniperus virginiana, Matricaria chamomilla, Anthemis nobilis, Helichrysium angustifolia, Jasmine grandiflorum, Lavandula angustifolia, Mentha piperita, Citrus sinensis, Achillea millefolium, Citrus bergamia, Calendula*, or Tea Tree.

3. The method according to claim 1, wherein the composition is a shampoo and comprises:

| | |
|---|---|
| biotin | 0.025%; |
| caffeine | 0.0010%; |
| *Chenopodium quinoa* | 0.50%; |
| *Eclipta prostrata* | 0.03%; |
| *Lupinus* | 1.00%; |
| *Malus domestica* | 0.06%; |
| methylsulfonylmethane | 0.8%; |
| *Momordica charantia* | 0.05%; |
| *Moringa olifiera* | 1.00%; |
| *Rosmarinus officinalis* | 0.03%; |
| *Scutellaria baicalensis* | 0.10%; |
| Vitamin E (α tocopherol) | 0.2%; and |
| *Ocimum basilicum* | 0.00%, and |
| *Pisum sativum* | 0.00% |
| proanthocyanidin | 0.19%. |

4. The method according to claim 1, wherein the composition is a conditioner and comprises:

| | |
|---|---|
| biotin | 0.025%; |
| caffeine | 0.0010%; |
| *Chenopodium quinoa* | 0.50%; |
| *Eclipta prostrata* | 0.15%; |
| *Lupinus* | 2.50%; |
| *Malus domestica* | 0.19%; |
| methylsulfonylmethane | 0.8%; |
| *Momordica charantia* | 0.10%; |
| *Moringa olifiera* | 2.00%; |
| *Rosmarinus officinalis* | 0.03%; |
| *Scutellaria baicalensis* | 0.10%; |
| Vitamin E (α tocopherol) | 0.4%; and |
| *Ocimum basilicum* | 0.00%, and |
| *Pisum sativum* | 0.00% |
| proanthocyanidin | 0.56%. |

5. The method according to claim 1, wherein the composition is a scalp or a skin cream and comprises:

| | |
|---|---|
| biotin | 0.025%; |
| caffeine | 0.0010%; |
| *Chenopodium quinoa* | 1.50%; |
| *Eclipta prostrata* | 0.30%; |
| *Lupinus* | 2.50%; |
| *Malus domestica* | 0.25%; |
| methylsulfonylmethane | 0.8%; |
| *Momordica charantia* | 0.20%; |
| *Moringa olifiera* | 2.00%; |
| *Ocimum basilicum* | 2.00%; |
| *Pisum sativum* | 4.00%; |
| *Rosmarinus officinalis* | 0.30%; |
| *Scutellaria baicalensis* | 0.17%; |
| Vitamin E (α tocopherol) | 0.50%; and |
| proanthocyanidin | 0.75%. |

* * * * *